United States Patent
Cheng et al.

(10) Patent No.: US 11,053,542 B2
(45) Date of Patent: Jul. 6, 2021

(54) COMPOSITIONS AND METHODS FOR SCREENING MUTATIONS IN THYROID CANCER

(71) Applicant: Quest Diagnostics Investments LLC, Madison, NJ (US)

(72) Inventors: Shih-Min Cheng, San Juan Capistrano, CA (US); Joseph J. Catanese, San Juan Capistrano, CA (US); Andrew Grupe, San Juan Capistrano, CA (US); Feras Hantash, Mission Viejo, CA (US); Frederic M. Waldman, San Juan Capistrano, CA (US); Kevin Qu, San Juan Capistrano, CA (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 149 days.

(21) Appl. No.: 16/067,189

(22) PCT Filed: Dec. 30, 2016

(86) PCT No.: PCT/US2016/069478
§ 371 (c)(1),
(2) Date: Jun. 29, 2018

(87) PCT Pub. No.: WO2017/117523
PCT Pub. Date: Jul. 6, 2017

(65) Prior Publication Data
US 2019/0112653 A1    Apr. 18, 2019

Related U.S. Application Data

(60) Provisional application No. 62/439,572, filed on Dec. 28, 2016, provisional application No. 62/273,783, filed on Dec. 31, 2015.

(51) Int. Cl.
*C12Q 1/6874* (2018.01)
*C12Q 1/6886* (2018.01)
*C12Q 1/6869* (2018.01)
*C12N 15/10* (2006.01)

(52) U.S. Cl.
CPC ....... *C12Q 1/6874* (2013.01); *C12N 15/1068* (2013.01); *C12Q 1/6869* (2013.01); *C12Q 1/6886* (2013.01); *C12Q 2600/106* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

| | | |
|---|---|---|
| 2013/0323727 A1 | 12/2013 | Huang et al. |
| 2015/0299808 A1 | 10/2015 | Gonzalez Diaz et al. |
| 2015/0315571 A1 | 11/2015 | Cogan et al. |

FOREIGN PATENT DOCUMENTS

| | | |
|---|---|---|
| EP | 2439531 A2 | 4/2012 |
| WO | WO 2012/018613 A2 | 2/2012 |
| WO | WO 2012/130909 A1 | 10/2012 |
| WO | WO 2013/063544 A1 | 5/2013 |
| WO | WO 2014/152822 A2 | 9/2014 |
| WO | WO 2015/038190 A1 | 3/2015 |
| WO | WO 2015/153808 A1 | 10/2015 |

OTHER PUBLICATIONS

Cheng et al., "Development of a clinical targeted next-generation sequencing test for indeterminate thyroid nodules," Thyroid 2014, vol. 24, No. S1 (Abstracts from "84th Annual Meeting of the American Thyroid Association"), pp. A-49 to A-50 (see "Oral 125"), published online Oct. 23, 2014. (Year: 2014).*
Hu et al., "A Common Polymorphism in the Caspase Recruitment Domain of RIG-I Modifies the Innate Immune Response of Human Dendritic Cells," J. Immunol. 2010, 185:424-432. (Year: 2010).*
Supplementary European Search Report dated Sep. 2, 2019, in EP 16882749.1.
Celestino et al., "Survey of 548 Oncogenic Fusion Transcripts in Thyroid Tumors Supports the Importance of the Already Established Thyroid Fusions Genes," Genes, Chromosomes & Cancer, Dec. 2012, 51(12):1154-1164.
Prasad et al., "Three-Gene Molecular Diagnostic Model for Thyroid Cancer," Thyroid, Mar. 1, 2012, 22(3):275-284.
International Search Report and Written Opinion dated May 26, 2017, in PCT/US2016/069478.
Chen et al., "PP22-4: Validation of a Targeted Next-Generation Sequencing Test for Indeterminate Thyroid Nodules in a Clinical Setting," Endocrine Society's 98$^{th}$ Annual Meeting and Expo, Apr. 2, 2016, p. 1-2.
Hsiao et al. "Molecular Approaches to Thyroid Cancer Diagnosis," Endocr. Relat. Cancer, Oct. 2014, 21(5):T301-T313.
Nikiforov et al. "Molecular Testing for Mutations in Improving the Fine-Needle Aspiration Diagnosis of Thyroid Nodules," J. Clin. Endocrinol. Metab., Jun. 2009, 94(6):2092-2098.
Nikoforova et al., "Targeted Next-Generation Sequencing Panel (ThyroSeq) for Detection of Mutations in Thyroid Cancer," J. Clin. Endocrinol. Metab., Nov. 2013, 98(11):E1852-E1860.
Office Action dated Nov. 2, 2020 in EP 16882749.1.

(Continued)

*Primary Examiner* — Kaijiang Zhang
(74) *Attorney, Agent, or Firm* — Foley & Lardner LLP

(57) ABSTRACT

The present technology relates to methods for determining whether a patient having thyroid nodules with indeterminate cytology will benefit from diagnostic surgery, e.g., lobectomy. These methods are based on screening a patient's thyroid nodules and detecting alterations in target nucleic acid sequences corresponding to a specific set of thyroid cancer-related genes. Kits for use in practicing the methods are also provided.

30 Claims, 20 Drawing Sheets
Specification includes a Sequence Listing.

(56) References Cited

OTHER PUBLICATIONS

Zahir et al., "Malignancy Risk Assessment in Patients with Thyroid Nodules Using Classification and Regression Trees," Journal of Thyroid Research, 2013, Article ID 983953, 1-9.
Zangenberg et al., "Multiplex PCR: Optimization Guidelines," PCR Applications. Protocols for Functional Genomics, May 1, 1999, Innis et al., Eds., Chapter 6, 73-94.

* cited by examiner

Figure 2A

| Primer Pairs | Final nM |
|---|---|
| AKT1_01B_FWD/REV_TAG | 250 |
| BRAF_01_FWD/REV_TAG | 250 |
| BRAF_02_FWD/REV_TAG | 250 |
| CTNNB1_04_FWD/REV_TAG | 750 |
| EIF1AX_01_FWD/REV_TAG | 500 |
| EIF1AX_02_FWD/REV_TAG | 750 |
| EIF1AX_03_FWD/REV_TAG | 1000 |
| GNAS_01_FWD/REV_TAG | 250 |
| GNAS_02_FWD/REV_TAG | 500 |
| HRAS_01_FWD/REV_TAG | 250 |
| HRAS_02A_FWD/REV_TAG | 250 |
| HRAS_03_FWD/REV_TAG | 500 |
| HRAS_04_FWD/REV_TAG | 500 |
| HRAS_05_FWD/REV_TAG | 500 |
| HRAS_06_FWD/REV_TAG | 500 |
| HRAS_07_FWD/REV_TAG | 500 |
| HRAS_08_FWD/REV_TAG | 500 |
| KRAS_03_FWD/REV_TAG | 1000 |
| KRAS_06_FWD/REV_TAG | 1000 |
| KRAS_07_FWD/REV_TAG | 1000 |
| KRAS_08_FWD/REV_TAG | 500 |
| KRAS_10_FWD/REV_TAG | 250 |
| KRAS_11_FWD/REV_TAG | 250 |
| NRAS_01_FWD/REV_TAG | 250 |
| NRAS_02_FWD/REV_TAG | 250 |
| NRAS_04_FWD/REV_TAG | 1000 |
| NRAS_05_FWD/REV_TAG | 250 |
| NRAS_06B_FWD/REV_TAG | 500 |
| NRAS_07_FWD/REV_TAG | 500 |
| PIK3CA_08A_FWD/REV_TAG | 250 |
| PIK3CA_09A_FWD/REV_TAG | 500 |
| PIK3CA_09B_FWD/REV_TAG | 250 |
| PIK3CA_10_FWD/REV_TAG | 250 |
| PIK3CA_14_FWD/REV_TAG | 500 |
| PTEN_06_FWD/REV_TAG | 500 |
| PTEN_08A_FWD/REV_TAG | 250 |
| PTEN_10B_FWD/REV_TAG | 250 |
| PTEN_13_FWD/REV_TAG | 500 |
| PTEN_16_FWD/REV_TAG | 1000 |
| RET_01_FWD/REV_TAG | 500 |
| RET_02_FWD/REV_TAG | 500 |
| RET_04_FWD/REV_TAG | 500 |

| | |
|---|---|
| RET_05_FWD/REV_TAG | 250 |
| RET_06A_FWD/REV_TAG | 1000 |
| RET_07_FWD/REV_TAG | 500 |
| RET_08_FWD/REV_TAG | 250 |
| TERT_02_FWD/REV_TAG | 250 |
| TP53_03_FWD/REV_TAG | 250 |
| TP53_05_FWD/REV_TAG | 1000 |
| TP53_06_FWD/REV_TAG | 1500 |
| TP53_07_FWD/REV_TAG | 500 |
| TP53_08B_FWD/REV_TAG | 500 |
| TP53_08C_FWD/REV_TAG | 1000 |
| TSHR_01_FWD/REV_TAG | 250 |
| TSHR_02_FWD/REV_TAG | 250 |
| TSHR_03_FWD/REV_TAG | 1000 |
| TSHR_04A_FWD/REV_TAG | 250 |
| TSHR_05_FWD/REV_TAG | 250 |
| TSHR_06_FWD/REV_TAG | 250 |

| Primer Pairs | Final nM |
|---|---|
| F_ABL1_Ex2_F_ABL1_Ex3_R_TAG | 150 |
| F_AGGF1_Ex5_F-RAF1_Ex8_R_TAG | 600 |
| F_AGK_Ex2_F-BRAF_Ex8_R_TAG | 600 |
| F_AKAP9_Ex8_F-BRAF_Ex9_R_TAG | 600 |
| F_BRAF_Ex8_F-MACF1_Ex15_R_TAG | 600 |
| F_CREB3L2_Ex2_F-PPARG_Ex5_R_TAG | 600 |
| F_EML4_Ex13_F-ALK_Ex20_R_TAG | 600 |
| F_EML4_Ex20_F-ALK_Ex20_R_TAG | 600 |
| F_EML4_Ex6_F-ALK_Ex20_R_TAG | 600 |
| F_ERC1_Ex11_F-RET_Ex12_R_TAG | 600 |
| F_ETV6_Ex4_F-NTRK3_Ex14_R_TAG | 600 |
| F_ETV6_Ex5_F-NTRK3_Ex14_R_TAG_B | 600 |
| F_FGFR2_OFD1_1 | 600 |
| F_GAPDHL_Ex1_F_GAPDH_Ex3_R_TAG | 75 |
| F_GOLGA5_Ex7_F-RET_Ex12_R_TAG | 600 |
| F_HOOK3_Ex11_F-RET_Ex12_R_TAG | 600 |
| F_KRT20L_Ex1_F_KRT20_Ex2_R_TAG | 150 |
| F_KRT7_Ex4_F-KRT7_Ex5_R_TAG | 150 |
| F_KTN1_Ex30_F-RET_Ex12_R_TAG | 600 |
| F_MACF1_Ex60_F-BRAF_Ex9_R_TAG | 600 |
| F_NCOA4_Ex10_F-RET_Ex12_R_TAG | 600 |
| F_NCOA4_Ex9_F-RET_Ex12_R_TAG | 600 |
| F_PAX8_Ex10_F-PPARG_Ex5_R_TAG | 600 |
| F_PAX8_Ex7_F-PPARG_Ex5_R_TAG | 600 |
| F_PAX8_Ex8_F-PPARG_Ex5_R_TAG | 600 |
| F_PAX8_Ex9_F-PPARG_Ex5_R_TAG | 600 |
| F_PCM1_Ex29_F-RET_Ex12_R_TAG | 600 |
| F_PRKAR1A_Ex8_F-RET_Ex12_R_TAG | 600 |
| F_PTH_1 | 150 |
| F_RET/PTC1_TAG | 600 |
| F_SND1_Ex10_F-BRAF_Ex9_R_TAG | 600 |
| F_STRN_Ex3_F-ALK_Ex20_R_TAG | 600 |
| F_TFG_Ex5_F-MET_Ex15_R_TAG | 600 |
| F_TFG_Ex5_F-NTRK1_Ex12_R_TAG | 600 |
| F_TFRC_1 | 150 |
| F_TG_Ex5_F-TG_Ex6_R_TAG | 75 |
| F_THADA_IGF2BP3_1 | 600 |
| F_THADA_PPARG_iso1+7p_1 | 600 |
| F_THADA_PPARG_iso2_1 | 600 |
| F_TPM3_Ex10_F-NTRK1_Ex12_R_TAG | 600 |
| F_TPR_Ex21_F-NTRK1_Ex12_R_TAG | 600 |
| F_TRA2A_THADA_1 | 600 |
| F_TRIM24_Ex9_F-RET_Ex12_R_TAG | 600 |

Figure 2B (contd.)

| | |
|---|---|
| F_TRIM27_Ex3_F-RET_Ex12_R_TAG | 600 |
| F_TRIM33_Ex16_F-RET_Ex12_R_TAG | 600 |
| F_UACA_Ex17_F-LTK_Ex10_R TAG | 600 |
| F_VCL_FGFR2_1 | 600 |
| R_ABL1_Ex2_F_ABL1_Ex3_R_TAG | 150 |
| R_AGGF1_Ex5_F-RAF1_Ex8_R_TAG | 600 |
| R_AGK_Ex2_F-BRAF_Ex8_R_TAG | 600 |
| R_AKAP9_Ex8_F-BRAF_Ex9_R_TAG | 600 |
| R_BRAF_Ex8_F-MACF1_Ex15_R TAG | 600 |
| R_CREB3L2_Ex2_F-PPARG_Ex5_R_TAG | 600 |
| R_ETV6_Ex4_F-NTRK3_Ex14_R_TAG | 600 |
| R_ETV6_Ex5_F-NTRK3_Ex14_R_TAG | 600 |
| R_FGFR2_OFD1_1 | 600 |
| R_GAPDHL_Ex1_F_GAPDH_Ex3_R_TAG | 75 |
| R_KRT20L_Ex1_F_KRT20_Ex2_R_TAG | 150 |
| R_KRT7_Ex4_F-KRT7_Ex5_R_TAG | 150 |
| R_NCOA4_Ex10_F-RET_Ex12_R_ TAG | 600 |
| R_NCOA4_Ex9_F-RET_Ex12_R_TAG | 600 |
| R_PTH_1 | 150 |
| R_RET/PTC1_ TAG | 600 |
| R_STRN_Ex3_F-ALK_Ex20_R_TAG | 600 |
| R_TFG_Ex5_F-MET_Ex15_R TAG | 600 |
| R_TFG_Ex5_F-NTRK1_Ex12_R_TAG | 600 |
| R_TFRC_1 | 150 |
| R_TG_Ex5_F-TG_Ex6_R_TAG | 75 |
| R_THADA_7p_1 | 600 |
| R_THADA_IGF2BP3_1 | 600 |
| R_THADA_PPARG_iso1_1 | 600 |
| R_THADA_PPARG_iso2_1 | 600 |
| R_TRA2A_THADA_1 | 600 |
| R_UACA_Ex17_F-LTK_Ex10_R TAG | 600 |
| R_VCL_FGFR2_1 | 600 |

Figure 3

| Sample ID | Specimen Type | Gene | Position | Expected Mutation (%) | SJC Result Mutation (%) | Matched? |
|---|---|---|---|---|---|---|
| Horizon Mix | Cell | AKT1 | 105246551 | E17K (5) | E17K (5) | Yes |
| | | BRAF | 140453136 | V600E (18) | V600E (20) | Yes |
| | | CTNNB1 | 41266101 | S33Y (20) | S33Y (19) | Yes |
| | | | 41266133 | S45del (10) | S45del (9) | Yes |
| | | KRAS | 25398281 | G12V (10) | G12V (14) | Yes |
| | | PIK3CA | 178936091 | G914R (5) | G914R (6) | Yes |
| | | | 178952085 | H1047R (25) | H1047R (27) | Yes |
| SJC-A05 | Cytolyt | AKT1 | 105246551 | N/A | E17K (2) | N/A |
| | | BRAF | 140453136 | V600E | V600E (5) | Yes |
| | | KRAS | 25398281 | None | G12V (5) | No |
| SJC-A08 | FFPE | BRAF | 140453136 | None | V600E (3) | No |
| | | NRAS | 115256529 | Q61R | Q61r (64) | Yes |
| | | TERT | 1295250 | N/A | -146 C>T (45) | N/A |
| SJC-A09 | Cytolyt | HRAS | 533874 | Q61R | Q61R (19) | Yes |
| SJC-D01 | Cytolyt | | | None | None | Yes |
| SJC-D02 | Cytolyt | | | None | None | Yes |
| SJC-D04 | FFPE | | | None | None | Yes |
| SJC-D05 | FFPE | NRAS | 115256530 | Q61K | Q61K (81) | Yes |
| R-9824 | Cytolyt | | | None | None | Yes |
| R-9955 | Cytolyt | NRAS | 115256529 | Q61R | Q61R (11) | Yes |
| R-10272 | FFPE | | | None | None | Yes |
| R-10373 | Cytolyt | | | None | None | Yes |
| R-10375 | Cytolyt | | | None | None | Yes |
| R-10536 | FFPE | AKT1 | 105246551 | N/A | E17K (3) | N/A |
| | | BRAF | 140453136 | None | V600E (3) | No |
| | | KRAS | 25398281 | None* | G12V (2) | No |

Figure 4

Intra-assay reproducibility - Mutation

| Sample | Gene | Mutation | | Intra-1 | Intra-2 | Intra-3 | Mean | SD |
|---|---|---|---|---|---|---|---|---|
| QC1 | AKT1 | E17K | Frequency (%) | 4.2 | 5.5 | 5.7 | 5.1 | 0.8 |
| | CTNNB1 | S33Y | Frequency (%) | 15.9 | 18.4 | 16.6 | 17.0 | 1.2 |
| | | S45del | Frequency (%) | 9.5 | 8.1 | 5.5 | 7.7 | 2.1 |
| | KRAS | G13D | Frequency (%) | 10.0 | 12.4 | 10.1 | 10.8 | 1.4 |
| | NRAS | Q61R | Frequency (%) | 5.8 | 7.5 | 3.9 | 5.8 | 1.8 |
| | PIK3CA | E545K | Frequency (%) | 10.5 | 6.7 | 3.2 | 6.8 | 3.6 |
| | | H1047R | Frequency (%) | 25.0 | 26.9 | 23.7 | 25.2 | 1.6 |
| | TSHR | R274W | Frequency (%) | 10.2 | 8.8 | 10.1 | 9.7 | 0.8 |
| | | A581S | Frequency (%) | 14.9 | 13.0 | 9.3 | 12.4 | 2.9 |
| | BRAF | V600E | Frequency (%) | 19.3 | 18.7 | 24.0 | 20.7 | 2.9 |
| QC2 | | | | NEG | NEG | NEG | | |
| QC3 | | | | NEG | NEG | NEG | | |
| QC4 | NRAS | Q61R | Frequency (%) | 37.9 | 34.7 | 31.9 | 34.8 | 3.0 |
| QC5 | BRAF | V600E | Frequency (%) | 18.1 | 26.9 | 16.0 | 20.3 | 5.8 |
| QC6 | BRAF | V600E | Frequency (%) | 43.3 | 43.1 | 43.4 | 43.3 | 0.1 |
| | TERT | 228 | Frequency (%) | 18.3 | 12.3 | 18.7 | 16.4 | 3.6 |
| QC7 | | | | NEG | NEG | NEG | | |
| QC8 | | | | NEG | NEG | NEG | | |

Figure 5

Intra-assay reproducibility - Translocation

| Sample | Targets | Result (Read count) | | |
|---|---|---|---|---|
| | | Intra-1 | Intra-2 | Intra-3 |
| QC1 | Fusion | Not detected (<50) | Not detected (<50) | Not detected (<50) |
| QC2 | EML4-ALK | *Detected (817) | Detected (1778) | *Detected (973) |
| | RET-PTC1 | *Not Detected (85) | Not detected (<50) | Not detected (<50) |
| QC3 | Fusion | Not detected (<50) | Not detected (<50) | Not detected (<50) |
| QC4 | Fusion | Not detected (<50) | Not detected (<50) | Not detected (<50) |
| QC5 | Fusion | Not detected (<50) | Not detected (<50) | Not detected (<50) |
| QC6 | Fusion | Not detected (<50) | Not detected (<50) | Not detected (<50) |
| QC7 | TPR-NTRK1 | Not detected (<50) | Not detected (<50) | *Not detected (134) |
| QC8 | RET-PTC1 | Detected (4236) | Detected (2994) | Detected (5074) |

Fusion: Detected (>1000), Not Detected (<50), Indeterminate/Repeat (50-1000); if repeat is still >50, result is "Detected"
ABL, GAPDH, KRT7: PASS (>500), QNS (<500)
TG: Thyroid enriched (>300), WIC (100-300), QNS (20-100), Non-thyroid enriched (<20)
*Original result was "Indeterminate/Repeat" based on read count (50-1000), Final result based on repeat.

Figure 6

Inter-assay reproducibility - Mutation

| Sample | Gene | Mutation | | Inter-1 | Inter-2 | Inter-3 | Inter-4 | Mean | SD |
|---|---|---|---|---|---|---|---|---|---|
| QC1 | AKT1 | E17K | Frequency (%) | 3.2 | 6.0 | 2.9 | 4.2 | 4.1 | 1.4 |
| | CTNNB1 | S33Y | Frequency (%) | 18.9 | 21.3 | 18.8 | 15.9 | 18.7 | 2.2 |
| | | S45del | Frequency (%) | 4.1 | 4.7 | 4.5 | 9.5 | 5.7 | 2.6 |
| | KRAS | G13D | Frequency (%) | 10.0 | 13.1 | 10.7 | 10.0 | 10.9 | 1.5 |
| | NRAS | Q61R | Frequency (%) | 6.2 | 5.9 | 5.3 | 5.8 | 5.8 | 0.4 |
| | PIK3CA | E545K | Frequency (%) | 5.7 | 3.5 | 5.7 | 10.5 | 6.3 | 3.0 |
| | | H1047R | Frequency (%) | 22.6 | 21.9 | 23.4 | 25.0 | 23.2 | 1.3 |
| | TSHR | R274W | Frequency (%) | 9.7 | 10.4 | 6.0 | 10.2 | 9.1 | 2.1 |
| | | A581S | Frequency (%) | 10.4 | 10.6 | 10.0 | 14.9 | 11.5 | 2.3 |
| | BRAF | V600E | Frequency (%) | 22.6 | 19.3 | 19.5 | 19.3 | 20.2 | 1.6 |
| QC2 | | | | NEG | NEG | NEG | NEG | | |
| QC3 | | | | NEG | NEG | NEG | NEG | | |
| QC4 | NRAS | Q61R | Frequency (%) | 37.4 | 34.1 | 40.9 | 37.9 | 37.6 | 2.8 |
| QC5 | BRAF | V600E | Frequency (%) | 19.6 | 23.7 | 25.5 | 18.1 | 21.7 | 3.5 |
| QC6 | BRAF | V600E | Frequency (%) | 45.7 | 40.9 | 41.7 | 43.3 | 42.9 | 2.1 |
| | TERT | 228 | Frequency (%) | 9.2 | 10.7 | 20.1 | 18.3 | 14.6 | 5.4 |
| QC7 | | | | NEG | NEG | NEG | NEG | | |
| QC8 | | | | NEG | NEG | NEG | NEG | | |

Figure 7

Inter-assay reproducibility - Translocation

| Sample | Targets | Result (Read count) | | |
|---|---|---|---|---|
| | | Inter-1 | Inter-2 | Inter-3 |
| QC1 | EML4-ALK | *Not Detected (113) | *Not Detected (146) | Not Detected (<50) |
| QC2 | EML4-ALK | Detected (6701) | Detected (7642) | Detected (4018) |
| | PAX8E8-PPARG | *Not Detected (774) | Not Detected (<50) | Not Detected (<50) |
| QC3 | Fusion | Not Detected (<50) | Not Detected (<50) | Not Detected (<50) |
| QC4 | Fusion | Not Detected (<50) | Not Detected (<50) | Not Detected (<50) |
| QC5 | Fusion | Not Detected (<50) | Not Detected (<50) | Not Detected (<50) |
| QC6 | Fusion | Not Detected (<50) | Not Detected (<50) | Not Detected (<50) |
| QC7 | Fusion | Not Detected (<50) | Not Detected (<50) | Not Detected (<50) |
| QC8 | RET-PTC1 | Detected (15168) | Detected (4318) | Detected (2974) |

Fusion: Detected (>1000), Not Detected (<50), Indeterminate/Repeat (50-1000); if repeat is still >50, result is "Detected"

*Original result was "Indeterminate/Repeat" based on read count (50-1000), Final result based on repeat.

(A) Analytical Sensitivity Study: DNA 1 (2 ng/uL, FFPE)

| Dilutions | Mutations Frequency | BRAF V600E Expected | Observed | TERT-228 Expected | Observed |
|---|---|---|---|---|---|
| Undiluted | | 47% | 47.2 | 7% | 6.9 |
| 1:2 | | 23% | 17.5 | 4% | 3.8 |
| 1:4 | | 11% | 5.0 | 2% | 2.1 |
| 1:8 | | 5% | 2.8 | 1% | ND |
| 1:16 | | 2% | 1.5 | | ND |
| 1:32 | | 1% | 0.6 | | ND |

(B) Analytical Sensitivity Study: DNA 2 (2 ng/uL FNA)

| Dilutions | Mutations Frequency | BRAF V600E Expected | Observed |
|---|---|---|---|
| Undiluted | | 21% | 20.8 |
| 1:2 | | 10% | 8.9 |
| 1:4 | | 5% | 4.7 |
| 1:8 | | 3% | 2.0 |
| 1:16 | | 2% | 1.4 |
| 1:32 | | 1% | 0.5 |

(C) Analytical Sensitivity Study: DNA 3 (2 ng/uL, FFPE)

| Dilutions | Mutations Frequency | KRAS G12D Expected | Observed | TP53 12nt DEL Expected | Observed |
|---|---|---|---|---|---|
| Undiluted | | 35% | 35.1 | 45% | 44.6 |
| 1:2 | | 18% | 9.7 | 23% | 11.8 |
| 1:5 | | 7% | 3.3 | 9% | 2.2 |
| 1:10 | | 3% | 1.6 | 4% | 1.3 |
| 1:20 | | 2% | 0.9 | 2% | ND |
| 1:40 | | 1% | ND | 1% | ND |

ND: Not Detected.

Figure 8

| (A) Analytical Sensitivity Study: RNA 1 (2 ng/uL, FFPE) | | |
| --- | --- | --- |
| Dilution | Analyte | Result (read count) |
| Undiluted | EML4-ALK | Detected (3339) |
| 1:2 | EML4-ALK | Detected (1780) |
| 1:4 | EML4-ALK | Detected (1400) |
| 1:8 | EML4-ALK | Repeat (308) |
| 1:16 | EML4-ALK | Repeat (560) |
| 1:32 | EML4-ALK | Repeat (276) |
| 1:64 | EML4-ALK | Not Deteceted (0) |

Detected (>1000), Not Detected (<50), Repeat (50-1000)

| (B) Analytical Sensitivity Study: RNA 2 (2 ng/uL, FNA) | | |
| --- | --- | --- |
| Dilution | Analyte | Result (read count) |
| Undiluted | RET-PTC1 | Detected (2493) |
| 1:2 | RET-PTC1 | Repeat (899) |
| 1:4 | RET-PTC1 | Repeat (530) |
| 1:8 | RET-PTC1 | Repeat (268) |
| 1:16 | RET-PTC1 | Repeat (162) |
| 1:32 | RET-PTC1 | Repeat (64) |
| 1:64 | RET-PTC1 | Not Deteceted (0) |

Detected (>1000), Not Detected (<50), Repeat (50-1000)

(A) Detection Limit Study: DNA 1 (FFPE)

| Concentration (ng/μL) | Frequency % | |
| --- | --- | --- |
| | NRAS Q61R | TERT 250 |
| 2.5 | 64 | 29 |
| 2.0 | 66 | 37 |
| 1.5 | 65 | 56 |
| 1.0 | 64 | 45 |
| 0.75 | 62 | 43 |
| 0.5 | 63 | 41 |
| 0.4 | 69 | 36 |
| 0.3 | 73 | 32 |
| 0.2 | 70 | 11 |
| 0.1 | 75 | 92 |

(B) Detection Limit Study: DNA 2 (FNA)

| Concentration (ng/μL) | Frequency % BRAF V600E |
| --- | --- |
| 2.0 | 21 |
| 1.5 | 23 |
| 1.0 | 25 |
| 0.75 | 17 |
| 0.5 | 24 |
| 0.4 | 16 |
| 0.3 | 22 |
| 0.2 | 15 |
| 0.1 | 13 |

| (A) Detection Limit Study: RNA 1 (FFPE) | | |
|---|---|---|
| Concentration (ng/uL) | Analyte | Result (read count) |
| 2.0 | PAX8-PPARG(E8) | Detected (14495) |
| 1.5 | PAX8-PPARG(E8) | Detected (31748) |
| 1.0 | PAX8-PPARG(E8) | Detected (16190) |
| 0.75 | PAX8-PPARG(E8) | Detected (34449) |
| 0.5 | PAX8-PPARG(E8) | Detected (20414) |
| 0.4 | PAX8-PPARG(E8) | Detected (38057) |
| 0.3 | PAX8-PPARG(E8) | Detected (17569) |
| 0.2 | PAX8-PPARG(E8) | Detected (105652) |
| 0.1 | PAX8-PPARG(E8) | Detected (21322) |

Detected (>1000), Not Detected (<50), Repeat (50-1000)

| (B) Detection Limit Study: RNA 2 (FNA) | | |
|---|---|---|
| Concentration (ng/uL) | Analyte | Result (read count) |
| 2.0 | RET-PTC1 | Detected (8960) |
| 1.5 | RET-PTC1 | Detected (3503) |
| 1.0 | RET-PTC1 | Detected (3270) |
| 0.75 | RET-PTC1 | Detected (2444) |
| 0.5 | RET-PTC1 | Detected (7138) |
| 0.4 | RET-PTC1 | Detected (4754) |
| 0.3 | RET-PTC1 | Detected (2812) |
| 0.2 | RET-PTC1 | Not detected (0) |
| 0.1 | RET-PTC1 | Not detected (0) |

Detected (>1000), Not Detected (<50), Repeat (50-1000)

(A) Recovery Study-Mutation: Horizon control (QC1) sample

| Gene | Chr. | Position | AA | Expected % | Inter-1 | Inter-2 | Inter-3 | Intra-1 | Intra-2 | Intra-3 | MS-1 | MD-2 | MC-1 | RP-1 | Mean | SD |
|---|---|---|---|---|---|---|---|---|---|---|---|---|---|---|---|---|
| AKT1 | 14 | 105246551 | E17K | 5 | 3.17 | 6.03 | 2.92 | 4.21 | 5.51 | 5.70 | 0.42 | 3.46 | 3.19 | 3.34 | 3.79 | 1.58 |
| BRAF | 7 | 140453136 | V600E | 18 | 22.58 | 19.27 | 19.50 | 19.30 | 18.69 | 24.03 | 17.59 | 22.10 | 19.31 | 22.30 | 20.47 | 1.99 |
| CTNNB1 | 3 | 41266101 | S33Y | 20 | 18.91 | 21.31 | 18.76 | 15.94 | 18.36 | 16.64 | 15.66 | 20.98 | 16.31 | 15.90 | 17.88 | 2.00 |
| | | 41266133 | S45del | 10 | 4.05 | 4.70 | 4.47 | 9.55 | 8.07 | 5.49 | 7.47 | 7.92 | 6.97 | 10.17 | 6.89 | 2.03 |
| KRAS | 12 | 25398281 | G13D | 10 | 10.03 | 13.07 | 10.70 | 10.00 | 12.43 | 10.06 | 10.60 | 6.05 | 10.10 | 12.41 | 10.54 | 1.86 |
| NRAS | 1 | 115256529 | Q61R | 5 | 6.23 | 5.89 | 5.34 | 5.84 | 7.51 | 3.92 | 3.10 | 3.69 | 5.81 | 6.06 | 5.34 | 1.28 |
| PIK3CA | 3 | 178936091 | E545K | 5 | 5.66 | 3.46 | 5.75 | 10.47 | 6.67 | 3.21 | 5.80 | 5.63 | 5.32 | 4.98 | 5.69 | 1.89 |
| | | 178952085 | H1047R | 25 | 22.65 | 21.92 | 23.41 | 25.02 | 26.87 | 23.75 | 22.15 | 28.74 | 24.65 | 33.65 | 25.28 | 3.45 |

Outside acceptable frequency range

(B) Horizon control (QC1) sample: Acceptable frequency range (%)

| Gene | Chr. | Position | AA | Acceptable range |
|---|---|---|---|---|
| AKT1 | 14 | 105246551 | E17K | 2.50 - 6.95 |
| BRAF | 7 | 140453136 | V600E | 16.49 - 24.45 |
| CTNNB1 | 3 | 41266101 | S33Y | 13.88 – 21.88 |
| | | 41266133 | S45del | 2.83 - 10.95 |
| KRAS | 12 | 25398281 | G13D | 6.82 – 14.26 |
| NRAS | 1 | 115256529 | Q61R | 2.78 - 7.90 |
| PIK3CA | 3 | 178936091 | E545K | 2.50 - 9.47 |
| | | 178952085 | H1047R | 18.38 – 32.18 |

Figure 13 (A)

Method Comparison: clinical samples.

| ID | Sample | | NGS DNA Result | | | | | NGS RNA Result | | | Concordance w/Previous Ops Results (Y/N)[1] | Additional alterations found (Y/N) |
|---|---|---|---|---|---|---|---|---|---|---|---|---|
| | Type | Result | DNA Var | Type | Freq | Var F/R | Ref F/R | Translocation | Cov | F/R | | |
| MC01 | FFPE | PAX8-PPARG | NEG | | | | | PAX8-PPARG (E8) | 25929 | 12648/13281 | Y | N |
| MC02 | FFPE | BRAF V600 | BRAF V600K | MNP | 40.3 | 8001/7909 | 11757/11774 | Non-thyroid enriched (TG<20) | | | Y | |
| | | | TERT 250 | SNP | 16.9 | 208/199 | 1038/966 | | | | | Y |
| MC03 | FNA | BRAF V600E | BRAF V600E | SNP | 33.8 | 2007/2001 | 3934/3929 | NEG | | | Y | N |
| MC04 | FNA | NEG | NEG | | | | | NEG | | | Y | N |
| MC05 | FFPE | BRAF K601E | BRAF K601E | SNP | 48.1 | 10255/10251 | 11090/11045 | NEG | | | Y | N |
| MC06 | FNA | NEG | NEG | | | | | Non-thyroid enriched (TG<20) | | | Y | |
| MC07 | FFPE | NEG | *RET M918T* | SNP | 33.0 | 9635/9620 | 19525/19495 | Non-thyroid enriched (TG<20) | | | Y | Y |
| MC08 | FNA | NEG | NEG | | | | | NEG, WIC | | | Y | N |
| MC09 | FNA | BRAF V600E | BRAF V600E | SNP | 24.9 | 2981/2983 | 8974/8968 | NEG | | | Y | |
| | | | TERT-228 | SNP | 13.9 | 272/126 | 1261/1210 | | | | | Y |
| MC10 | FNA | NEG | NEG | | | | | ETV6-NTRK3 | 6604 | 3288/3316 | Y | Y |
| MC11 | FFPE | NEG | PIK3CA E542K | SNP | 18.4 | 6832/6829 | 30379/30365 | Non-thyroid enriched (TG<20) | | | Y | Y |
| MC12 | FNA | NEG | NEG | | | | | NEG, WIC | | | Y | N |
| MC13 | FNA | NEG | GNAS Q227H | SNP | 22.7 | 1185/1183 | 4023/4020 | NEG | | | Y | Y |
| MC14 | FNA | NEG | NEG | | | | | NEG | | | Y | N |
| MC15 | FFPE | NEG | NEG | | | | | NEG | | | Y | N |
| MC16 | FNA | BRAF V600E | BRAF V600E | SNP | 14.9 | 1206/1202 | 6887/6878 | NEG | | | Y | N |
| MC17 | FFPE | NEG | PIK3CA E545K | SNP | 18.8 | 6298/6328 | 27364/27340 | Non-thyroid enriched (TG<20) | | | Y | Y |
| | | | TP53 Y220S | SNP | 22.3 | 550/549 | 1929/1908 | | | | | |
| MC18 | FNA | BRAF V600E | BRAF V600E | SNP | 23.8 | 2652/2651 | 8479/8476 | NEG | | | Y | N |
| MC19 | FFPE | NEG | NEG | | | | | NEG | | | Y | N |
| MC20 | FNA | NEG | NEG | | | | | QNS | | | QNS | N |
| MC21 | FNA | NEG | QNS | | | | | NEG, WIC | | | QNS | N |
| MC22 | FNA | NEG | NEG | | | | | NEG | | | Y | N |
| MC23 | FNA | NRAS Q61R | NRAS Q61R | SNP | 35.3 | 5846/5846 | 10719/10718 | NEG | | | Y | |
| | | | TSHR F631L | SNP | 28.2 | 17663/15402 | 42157/42102 | | | | | Y |
| MC24 | FNA | NEG | NEG | | | | | NEG | | | Y | N |
| MC25 | FNA | NEG | NEG | | | | | NEG | | | Y | N |
| MC26 | FFPE | NEG | *RET H745R* | | 15.4 | 882/881 | 4840/4839 | NEG, WIC | | | Y | Y |
| MC27 | FNA | NEG | NEG | | | | | NEG | | | Y | N |
| MC28 | FNA | NEG | GNAS R201H | | 23.9 | 2690/2688 | 8573/8569 | NEG | | | Y | Y |
| MC29 | FNA | NEG | NEG | | | | | NEG, WIC | | | Y | N |
| MC30 | FNA | NEG | NEG | | | | | NEG | | | Y | N |
| MC31 | FNA | NEG | NEG | | | | | NEG, WIC | | | Y | N |
| MC32 | FNA | BRAF V600E | BRAF V600E | SNP | 41.8 | 3774/3769 | 5265/5252 | NEG | | | Y | N |
| MC33 | FNA | KRAS G13D | KRAS G13D | SNP | 13.7 | 4767/4772 | 29958/29934 | NEG, WIC | | | Y | N |
| MC34 | FFPE | RET-PTC1 | *TERT 228* | SNP | 25.4 | 724/565 | 1855/1923 | RET-PTC1 | 3469 | 1734/1735 | Y | Y |
| MC35 | FNA | KRAS G12V | KRAS G12V | SNP | 6.7 | 875/878 | 12201/12198 | NEG | | | Y | N |
| MC36 | FNA | NRAS Q61K | NRAS Q61K | SNP | 38.4 | 5509/5504 | 8820/8828 | NEG, WIC | | | Y | |
| | | | TERT 228 | SNP | 35.2 | 3534/923 | 3825/4372 | | | | | Y |
| MC37 | FNA | RET-PTC3 | NEG | | | | | RET-PTC3 | 3260 | 1629/1631 | Y | N |
| MC38 | FNA | RET-PTC1 | NEG | | | | | RET-PTC1 | 2418 | 1209/1209 | Y | N |
| MC39 | FNA | NEG | NEG | | | | | NEG | | | Y | N |
| MC40 | FNA | NEG | NEG | | | | | NEG | | | Y | N |
| MC41 | FNA | NEG | NEG | | | | | NEG | | | Y | N |
| MC42 | FNA | NEG | NEG | | | | | NEG | | | Y | N |
| MC43 | FNA | NEG | NEG | | | | | NEG | | | Y | N |
| MC44 | FFPE | KRAS G12D | KRAS G12D | SNP | 33.6 | 5774/5765 | 11416/11419 | N/A (non-RNA sample) | | | Y | N |
| | | TP53 16nt DEL[2] | TP53 16nt DEL | DEL | 49.1 | 1279/1275 | 1324/1323 | | | | | |
| MC45 | FNA | NEG | TSHR T632I | SNP | 30.5 | 12251/12087 | 39871/39884 | NEG | | | Y | Y |
| MC46 | FFPE | NEG | NEG | | | | | NEG | | | Y | N |
| MC47 | FFPE | KRAS G12V | KRAS G12V | SNP | 17.9 | 4298/4289 | 19721/19703 | Non-thyroid enriched (TG<20) | | | Y | N |
| MC48 | FFPE | EML4-ALK | NEG | | | | | EML4-ALK | 3339 | 1669/1670 | Y | N |
| Total concordance | | | | | | | | | | | 100% (46/46) | Y=13 (27.1%) |

[1] Concordance is represents the 7-gene thyroid panel result (i.e. N-/K-/H-RAS, BRAF, RET-PTC, and PAX8-PPARG), unless otherwise specified. Italicized results indicate variants that were found in additional
[2] TP53 result was verified by OncoVantage PGM sequencing

Figure 13 (B)

|  |  | NGS test | |
|---|---|---|---|
|  |  | POS | NEG |
| 7-Gene test | POS | 15 | 0 |
|  | NEG | 5 | 20 |

Figure 15(A)

Recovery study: gBlock fusion fragments

| gBlock name | Copy No. | Reads |
|---|---|---|
| AGGF1_Ex5_F-RAF1_Ex8_R | 100 | 6326 |
| AGK_Ex2_F-BRAF_Ex8_R | 100 | 14346 |
| AKAP9_Ex8_F-BRAF_Ex9_R | 100 | 5170 |
| BRAF_Ex8_F-MACF1_Ex15_R | 100 | 3342 |
| CREB3L2_Ex2_F-PPARG_Ex5_R | 100 | 5272 |
| EML4_Ex13_F-ALK_Ex20_R | 100 | 5212 |
| EML4_Ex20_F-ALK_Ex20_R | 400 | 6493 |
| EML4_Ex6_F-ALK_Ex20_R | 100 | 7016 |
| ERC1_Ex11_F-RET_Ex12_R | 2000 | 9718 |
| ETV6_Ex4_F-NTRK3_Ex14_R | 400 | 16176 |
| ETV6_Ex5_F-NTRK3_Ex14_R | 100 | 1088 |
| GOLGA5_Ex7_F-RET_Ex12_R | 400 | 27089 |
| HOOK3_Ex11_F-RET_Ex12_R | 2000 | 7986 |
| KTN1_Ex30_F-RET_Ex12_R | 100 | 26071 |
| MACF1_Ex60_F-BRAF_Ex9_R | 100 | 2564 |
| NCOA4_Ex9_F-RET_Ex12_R | 400 | 6399 |
| PCM1_Ex29_F-RET_Ex12_R | 100 | 32712 |
| PRKAR1A_Ex8_F-RET_Ex12_R | 400 | 29690 |
| SND1_Ex10_F-BRAF_Ex9_R | 100 | 14706 |
| STRN_Ex3_F-ALK_Ex20_R | 100 | 2474 |
| TFG_Ex5_F-MET_Ex15_R | 100 | 4397 |
| TFG_Ex5_F-NTRK1_Ex12_R | 100 | 11489 |
| TPR_Ex21_F-NTRK1_Ex12_R | 400 | 54472 |
| TRIM27_Ex3_F-RET_Ex12_R | 100 | 49076 |
| TRIM33_Ex16_F-RET_Ex12_R | 100 | 4701 |
| UACA_Ex17_F-LTK_Ex10_R | 100 | 54951 |

Figure 15(B)

| G-Blocks | Copy Number | Reads |
|---|---|---|
| FGFR2_OFD1_1 | 400 | 30465 |
| THADA_7p_1 | 400 | 7206 |
| THADA_IGF2BP3_1 | 400 | 10088 |
| THADA_PPARG_iso1_1 | 400 | 33507 |
| THADA_PPARG_iso2_1 | 400 | 122478 |
| TRA2A_THADA_1 | 400 | 49442 |
| VCL_FGFR2_1 | 400 | 17127 |
| PTH_1 | 400 | 17710 |

```
                       SEQUENCE LISTING

<160> NUMBER OF SEQ ID NOS: 193

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cgacgctctt ccgatcttca cgttggtcca catc                                34

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agacgtgtgc tcttccgatc tggtctgacg ggtagagt                            38

<210> SEQ ID NO 3
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgacgctctt ccgatcttgg aaaaatagcc tcaattct                            38

<210> SEQ ID NO 4
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agacgtgtgc tcttccgatc ttgttttcct ttacttacta cacc                     44

<210> SEQ ID NO 5
<211> LENGTH: 37
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 5
cgacgctctt ccgatctaga caactgttca aactgat                                    37

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agacgtgtgc tcttccgatc tatgcttgct ctgatagga                                  39

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cgacgctctt ccgatctgcg gctgttagtc act                                        33

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agacgtgtgc tcttccgatc ttccctgttc ccactcata                                  39

<210> SEQ ID NO 9
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgacgctctt ccgatctctg accatcctct ttgaatac                                   38

<210> SEQ ID NO 10
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agacgtgtgc tcttccgatc tttcatttta tttcatactg ttttacaga                       49

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgacgctctt ccgatctgtg agcactaaag taaataagc          39

<210> SEQ ID NO 12
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
agacgtgtgc tcttccgatc tcagacgaag ctagaagtct          40

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cgacgctctt ccgatctaaa cacaaggtac atctacttac          40

<210> SEQ ID NO 14
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
agacgtgtgc tcttccgatc tttacagtgc tgacttatga gt          42

<210> SEQ ID NO 15
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cgacgctctt ccgatctcca gacctttgct ttagatt          37

<210> SEQ ID NO 16
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agacgtgtgc tcttccgatc tgcttactgg aagttgactt t          41

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cgacgctctt ccgatctcca gtccctctgg aataa         35

<210> SEQ ID NO 18
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
agacgtgtgc tcttccgatc tagaagcaaa gcgttcttta c         41

<210> SEQ ID NO 19
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cgacgctctt ccgatctaaa gacttggtgt tgttgat         37

<210> SEQ ID NO 20
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
agacgtgtgc tcttccgatc tggaagcagg tggtcatt         38

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cgacgctctt ccgatctctc tatagtgggg tcgtat         36

<210> SEQ ID NO 22
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
agacgtgtgc tcttccgatc tagaccctgt aggaggac         38

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

-continued cgacgctctt ccgatcttcc ctggctagct gt        32

<210> SEQ ID NO 24
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agacgtgtgc tcttccgatc tggactcgga tgacgtg        37

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cgacgctctt ccgatctagc ctgccgagat tc        32

<210> SEQ ID NO 26
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
agacgtgtgc tcttccgatc tgtcctggat gccgc        35

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cgacgctctt ccgatcttgc gcagagagga ca        32

<210> SEQ ID NO 28
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
agacgtgtgc tcttccgatc tcggggaggg cttcc        35

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cgacgctctt ccgatctccg gtgcgcatgt            30

<210> SEQ ID NO 30
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
agacgtgtgc tcttccgatc tccacggaag gtcctga            37

<210> SEQ ID NO 31
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cgacgctctt ccgatctcac catgcagggg ac            32

<210> SEQ ID NO 32
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
agacgtgtgc tcttccgatc tctgaccatc cagctgatc            39

<210> SEQ ID NO 33
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cgacgctctt ccgatctcca gcttatattc cgtcatc            37

<210> SEQ ID NO 34
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
agacgtgtgc tcttccgatc tgggtttgcc cttcagat            38

<210> SEQ ID NO 35
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cgacgctctt ccgatctgga tcatattcgt ccacaaa            37

<210> SEQ ID NO 36
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
agacgtgtgc tcttccgatc tgtgtgacat gttctaatat agtca            45

<210> SEQ ID NO 37
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cgacgctctt ccgatctcat aaacattatt taaaattttt tattaaatat tatatgc     57

<210> SEQ ID NO 38
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
agacgtgtgc tcttccgatc ttgtatttgc cataaataat actaaatca            49

<210> SEQ ID NO 39
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cgacgctctt ccgatctacc cacctataat ggtgaata                        38

<210> SEQ ID NO 40
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
agacgtgtgc tcttccgatc taacctgtct cttggatatt ct                   42

<210> SEQ ID NO 41
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cgacgctctt ccgatctggt cctgcaccag taatat                          36

<210> SEQ ID NO 42
<211> LENGTH: 47
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 42
agacgtgtgc tcttccgatc tgctgaaaat gactgaatat aaacttg            47

<210> SEQ ID NO 43
<211> LENGTH: 43
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 43
cgacgctctt ccgatctcag atctgtattt atttcagtgt tac                43

<210> SEQ ID NO 44
<211> LENGTH: 44
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 44
agacgtgtgc tcttccgatc tagttaagga ctctgaagat gtac               44

<210> SEQ ID NO 45
<211> LENGTH: 39
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 45
cgacgctctt ccgatctgga attccataac ttcttgcta                    39

<210> SEQ ID NO 46
<211> LENGTH: 45
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 46
agacgtgtgc tcttccgatc tgtgttacta atgactgtgc tataa              45

<210> SEQ ID NO 47
<211> LENGTH: 39
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 47
cgacgctctt ccgatctata atgctcctag tacctgtag                    39

-continued

```
<210> SEQ ID NO 48
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
agacgtgtgc tcttccgatc tacctgtttg ttggacatac t                           41

<210> SEQ ID NO 49
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
cgacgctctt ccgatctggt gggatcatat tcatctac                               38

<210> SEQ ID NO 50
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
agacgtgtgc tcttccgatc tcgccaatta accctgatta                             40

<210> SEQ ID NO 51
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cgacgctctt ccgatctgtg ggcttgtttt gtatca                                 36

<210> SEQ ID NO 52
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
agacgtgtgc tcttccgatc tgtacccagc ctaatcttgt                             40

<210> SEQ ID NO 53
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
cgacgctctt ccgatcttct tccctagtgt ggtaac                                 36

<210> SEQ ID NO 54
```

```
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
agacgtgtgc tcttccgatc tgaaggcttc ctctgtgtat t                          41

<210> SEQ ID NO 55
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cgacgctctt ccgatctcgc ctgtcctcat gtat                                  34

<210> SEQ ID NO 56
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
agacgtgtgc tcttccgatc ttccctgccc ccttac                                36

<210> SEQ ID NO 57
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cgacgctctt ccgatcttca gcgggctacc a                                     31

<210> SEQ ID NO 58
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
agacgtgtgc tcttccgatc ttgctggtgt gaaatgact                             39

<210> SEQ ID NO 59
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
cgacgctctt ccgatcttat tattttattt tacagagtaa cagactag                   48

<210> SEQ ID NO 60
<211> LENGTH: 41
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
agacgtgtgc tcttccgatc ttttagcact tacctgtgac t                          41

<210> SEQ ID NO 61
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
cgacgctctt ccgatctgat gtgttacaag gcttatcta                             39

<210> SEQ ID NO 62
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
agacgtgtgc tcttccgatc tgcctcttgc tcagttttat c                          41

<210> SEQ ID NO 63
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
cgacgctctt ccgatcttgg aatgccagaa ctaca                                 35

<210> SEQ ID NO 64
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
agacgtgtgc tcttccgatc tgtggaagat ccaatccatt tt                         42

<210> SEQ ID NO 65
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
cgacgctctt ccgatctgag gctttggagt atttca                                36

<210> SEQ ID NO 66
<211> LENGTH: 42
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 66
agacgtgtgc tcttccgatc tctgctgaga gttattaaca gt                42

<210> SEQ ID NO 67
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
cgacgctctt ccgatctgtc tacgaaagcc tctcta                36

<210> SEQ ID NO 68
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
agacgtgtgc tcttccgatc tggcatgctg tcgaatag                38

<210> SEQ ID NO 69
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
cgacgctctt ccgatctaca atcatgttgc agca                34

<210> SEQ ID NO 70
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
agacgtgtgc tcttccgatc taaaaacatc aaaaaataac ttaccttt                49

<210> SEQ ID NO 71
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
cgacgctctt ccgatctcaa tttagtgaaa taactataat ggaac                45

<210> SEQ ID NO 72
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
agacgtgtgc tcttccgatc tagtgccact ggtctataat          40

<210> SEQ ID NO 73
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
cgacgctctt ccgatctctg ccagctaaag gtgaagata           39

<210> SEQ ID NO 74
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
agacgtgtgc tcttccgatc tgcatcttgt tctgtttgtg gaa      43

<210> SEQ ID NO 75
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
cgacgctctt ccgatcttag agcgtgcaga taatga              36

<210> SEQ ID NO 76
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
agacgtgtgc tcttccgatc ttcaacaacc cccacaaa            38

<210> SEQ ID NO 77
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
cgacgctctt ccgatctgca caatatcctt ttgaagac            38

<210> SEQ ID NO 78
<211> LENGTH: 43
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 78
agacgtgtgc tcttccgatc tgcacatatc attacaccag ttc                    43

<210> SEQ ID NO 79
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
cgacgctctt ccgatctccc gggggattaa agc                               33

<210> SEQ ID NO 80
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
agacgtgtgc tcttccgatc ttcagatgtg ctgttgagac                        40

<210> SEQ ID NO 81
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
cgacgctctt ccgatctcca tgaggcagag cata                              34

<210> SEQ ID NO 82
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
agacgtgtgc tcttccgatc tgcaccgaga cgatgaa                           37

<210> SEQ ID NO 83
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
cgacgctctt ccgatctggc catggcctga c                                 31

<210> SEQ ID NO 84
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 84
agacgtgtgc tcttccgatc tgcacctggc tcctct                                    36

<210> SEQ ID NO 85
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
cgacgctctt ccgatctccc ctccttccta gaga                                      34

<210> SEQ ID NO 86
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
agacgtgtgc tcttccgatc tgagcaacac ccacactta                                 39

<210> SEQ ID NO 87
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
cgacgctctt ccgatcttat ggtcatggaa gggg                                      34

<210> SEQ ID NO 88
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
agacgtgtgc tcttccgatc tccccataca atttgatgac a                              41

<210> SEQ ID NO 89
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
cgacgctctt ccgatctgtg cgacgagctg t                                         31

<210> SEQ ID NO 90
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
agacgtgtgc tcttccgatc ttccggaagg tcatctca                                38

<210> SEQ ID NO 91
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
cgacgctctt ccgatctgga tccaaagtgg gaattc                                  36

<210> SEQ ID NO 92
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
agacgtgtgc tcttccgatc taggtacctt tcagcatctt c                            41

<210> SEQ ID NO 93
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
cgacgctctt ccgatctggg ccgcggaaag gaa                                     33

<210> SEQ ID NO 94
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
agacgtgtgc tcttccgatc ttggcggagg gactgg                                  36

<210> SEQ ID NO 95
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
cgacgctctt ccgatctgaa actttccact tgataagag                               39

<210> SEQ ID NO 96
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
agacgtgtgc tcttccgatc tccaagggtg cagttatg                    38

<210> SEQ ID NO 97
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
cgacgctctt ccgatcttta cctcgcttag tgct                        34

<210> SEQ ID NO 98
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
agacgtgtgc tcttccgatc ttgcctcttg cttctctt                    38

<210> SEQ ID NO 99
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
cgacgctctt ccgatcttgc agggtggcaa                             30

<210> SEQ ID NO 100
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
agacgtgtgc tcttccgatc tgcactggcc tcatcttg                    38

<210> SEQ ID NO 101
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
cgacgctctt ccgatctccc agagacccca gt                          32

<210> SEQ ID NO 102
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
agacgtgtgc tcttccgatc tcctcactga ttgctcttag g                          41

<210> SEQ ID NO 103
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
cgacgctctt ccgatctagc cctgtcgtct ct                                    32

<210> SEQ ID NO 104
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
agacgtgtgc tcttccgatc tgcagctgtg ggttgat                               37

<210> SEQ ID NO 105
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
cgacgctctt ccgatctcgt catgtgctgt gac                                   33

<210> SEQ ID NO 106
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
agacgtgtgc tcttccgatc tgccctgact ttcaactct                             39

<210> SEQ ID NO 107
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
cgacgctctt ccgatctaag gaactgatag caagaaac                              38

<210> SEQ ID NO 108
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
agacgtgtgc tcttccgatc tggtccctgc cacttac                     37

<210> SEQ ID NO 109
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
cgacgctctt ccgatctagt gaagacatgg tgtgta                      36

<210> SEQ ID NO 110
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
agacgtgtgc tcttccgatc ttggctggtg aggagaata                   39

<210> SEQ ID NO 111
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
cgacgctctt ccgatctgtc tttgtcctgc ttattct                     37

<210> SEQ ID NO 112
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
agacgtgtgc tcttccgatc tggcatggtt gtagtactca                  40

<210> SEQ ID NO 113
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
cgacgctctt ccgatcttga gtactacaac catgcca                     37

<210> SEQ ID NO 114
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
agacgtgtgc tcttccgatc tgaaggtgat ggcatacca                   39

<210> SEQ ID NO 115
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
cgacgctctt ccgatctgtt tgctgcttcc ttctc                            35

<210> SEQ ID NO 116
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
agacgtgtgc tcttccgatc ttgacgaagg caactatgt                        39

<210> SEQ ID NO 117
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
cgacgctctt ccgatctcga aatccgcagt acaa                             34

<210> SEQ ID NO 118
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
agacgtgtgc tcttccgatc ttggagttgc taacagtgat                       40

<210> SEQ ID NO 119
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
cgacgctctt ccgatcttgg agataacact ctaagcataa ctaaaggt              48

<210> SEQ ID NO 120
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
cgacgctctt ccgatctgca accttatccg acttcta                          37

<210> SEQ ID NO 121
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
cgacgctctt ccgatctgag gccattggct ctat                               34

<210> SEQ ID NO 122
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
cgacgctctt ccgatctcag ttgattttgg atcacttac                          39

<210> SEQ ID NO 123
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
cgacgctctt ccgatctgct cccaatgtgc atataa                             36

<210> SEQ ID NO 124
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
cgacgctctt ccgatctgcc cttcacccac atta                               34

<210> SEQ ID NO 125
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
cgacgctctt ccgatctctg ggaaaggacc taaag                              35

<210> SEQ ID NO 126
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
cgacgctctt ccgatctcgg gagactatga aatattgt                           38

```
<210> SEQ ID NO 127
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
cgacgctctt ccgatctaag gactcacggc ttaag                         35

<210> SEQ ID NO 128
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
cgacgctctt ccgatctcat ggtctctgtc tccc                          34

<210> SEQ ID NO 129
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
cgacgctctt ccgatcttcg aattctcact ctcacaacc                     39

<210> SEQ ID NO 130
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
cgacgctctt ccgatctagt cagccgcatc ttcttt                        36

<210> SEQ ID NO 131
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
cgacgctctt ccgatctcat ggagctggaa gaact                         35

<210> SEQ ID NO 132
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
cgacgctctt ccgatcttat gcagaatact gtcagtcta                     39

<210> SEQ ID NO 133
```

```
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
cgacgctctt ccgatctgaa gagctgcgaa gtcagatta                            39

<210> SEQ ID NO 134
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
cgacgctctt ccgatcttgg atgctgccta cat                                  33

<210> SEQ ID NO 135
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
cgacgctctt ccgatctgaa aaggaaaatg aattgaagag g                         41

<210> SEQ ID NO 136
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
cgacgctctt ccgatctaga agggctggat aaact                                35

<210> SEQ ID NO 137
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
cgacgctctt ccgatctccc caggactggc ttaccc                               36

<210> SEQ ID NO 138
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
cgacgctctt ccgatctcaa attcctgagc acttga                               36

<210> SEQ ID NO 139
<211> LENGTH: 33
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
cgacgctctt ccgatctcag ctatgcctcc tct                                33

<210> SEQ ID NO 140
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
cgacgctctt ccgatctagc ggcagcacta c                                  31

<210> SEQ ID NO 141
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
cgacgctctt ccgatctgca acctctcgac tca                                33

<210> SEQ ID NO 142
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
cgacgctctt ccgatctgtg tacgggcagt tca                                33

<210> SEQ ID NO 143
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
cgacgctctt ccgatcttag ttcacaacaa cctgtaag                           38

<210> SEQ ID NO 144
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
cgacgctctt ccgatctttt ggagaacttg ctttgat                            37

<210> SEQ ID NO 145
<211> LENGTH: 38
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 145
cgacgctctt ccgatctact cagcatcagc tactaaca                    38

<210> SEQ ID NO 146
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
cgacgctctt ccgatctcgc gacctgcgca aa                          32

<210> SEQ ID NO 147
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
cgacgctctt ccgatctatt gttgtgaagc tgaact                      36

<210> SEQ ID NO 148
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
cgacgctctt ccgatctcct ccaagctatg attctg                      36

<210> SEQ ID NO 149
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
cgacgctctt ccgatctagc gtttggctta acag                        34

<210> SEQ ID NO 150
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
cgacgctctt ccgatcttta tggcagcaag tatgtc                      36

<210> SEQ ID NO 151
<211> LENGTH: 39
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 151
cgacgctctt ccgatctata cctttcgtcc ctgcattta                              39

<210> SEQ ID NO 152
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
cgacgctctt ccgatctaca ccacagacat gatgat                                 36

<210> SEQ ID NO 153
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
cgacgctctt ccgatctcga actctgttgt ccacact                                37

<210> SEQ ID NO 154
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
cgacgctctt ccgatctccg atggatggta cttcttctg                              39

<210> SEQ ID NO 155
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
cgacgctctt ccgatctccg atggatggta cttcttctg                              39

<210> SEQ ID NO 156
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
cgacgctctt ccgatctgga agaaatcaag attcttactg                             40

<210> SEQ ID NO 157
<211> LENGTH: 40
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 157
cgacgctctt ccgatctcag agacaaatct tcatcttaac                              40

<210> SEQ ID NO 158
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
cgacgctctt ccgatctgaa gacgatcacc ttctccttat t                            41

<210> SEQ ID NO 159
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
cgacgctctt ccgatctcca ccaagtggtt tatcat                                  36

<210> SEQ ID NO 160
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
cgacgctctt ccgatctcag ttctcttgca acatct                                  36

<210> SEQ ID NO 161
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
cgacgctctt ccgatctgga aagccagaag ttgaata                                 37

<210> SEQ ID NO 162
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
cgacgctctt ccgatctcag caccaagtga aatctc                                  36

<210> SEQ ID NO 163
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 163
cgacgctctt ccgatctgat ctcccacctg gtgataatg                                    39

<210> SEQ ID NO 164
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
cgacgctctt ccgatctaaa actgcagaca agca                                         34

<210> SEQ ID NO 165
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
cgacgctctt ccgatctcag ccggaggtca ta                                           32

<210> SEQ ID NO 166
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
agacgtgtgc tcttccgatc tgatgtagtt gcttgggacc ca                                42

<210> SEQ ID NO 167
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
agacgtgtgc tcttccgatc tgctgattcg ctgtgact                                     38

<210> SEQ ID NO 168
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
agacgtgtgc tcttccgatc ttcgttgccc aaattgattt c                                 41

<210> SEQ ID NO 169
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
agacgtgtgc tcttccgatc tacgaaatcc ttggtctcta                                40

<210> SEQ ID NO 170
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
agacgtgtgc tcttccgatc tagcccagct cttctaca                                  38

<210> SEQ ID NO 171
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
agacgtgtgc tcttccgatc tgggagtggt cttccattac                                40

<210> SEQ ID NO 172
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
agacgtgtgc tcttccgatc ttgatgccgt ggttgat                                   37

<210> SEQ ID NO 173
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
agacgtgtgc tcttccgatc ttgatgccgt ggttgat                                   37

<210> SEQ ID NO 174
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
agacgtgtgc tcttccgatc tggagctccc ttctactgaa atg                            43

<210> SEQ ID NO 175
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
agacgtgtgc tcttccgatc tcaatacgac caaatccgtt gac        43

<210> SEQ ID NO 176
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
agacgtgtgc tcttccgatc tgtcctcagc agccagttta g        41

<210> SEQ ID NO 177
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
agacgtgtgc tcttccgatc tctgcagctc tgtcaact        38

<210> SEQ ID NO 178
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
cgacgctctt ccgatcttgg agataacact ctaagcataa ctaaaggt        48

<210> SEQ ID NO 179
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
agacgtgtgc tcttccgatc tcgagggaat tcccacttt        39

<210> SEQ ID NO 180
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
agacgtgtgc tcttccgatc ttgccaacat gacaatcata act        43

<210> SEQ ID NO 181
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
agacgtgtgc tcttccgatc tcaagttctt ccgagggaat tcc        43

<210> SEQ ID NO 182
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
agacgtgtgc tcttccgatc tcagtagttg gggttgtagt        40

<210> SEQ ID NO 183
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
agacgtgtgc tcttccgatc tccagatgtg ctgttagtgt        40

<210> SEQ ID NO 184
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
agacgtgtgc tcttccgatc tctggcagaa accttgaagt tg        42

<210> SEQ ID NO 185
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
agacgtgtgc tcttccgatc tagtggcaat acccagatac        40

<210> SEQ ID NO 186
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
agacgtgtgc tcttccgatc tcccattggc ctgagtttct        40

<210> SEQ ID NO 187
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
agacgtgtgc tcttccgatc tcagcacctc ccactgtaaa t                              41

<210> SEQ ID NO 188
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
agacgtgtgc tcttccgatc tagccaggtc actgagttac ta                             42

<210> SEQ ID NO 189
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
agacgtgtgc tcttccgatc ttctcttgaa cccaggaggt                                40

<210> SEQ ID NO 190
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
agacgtgtgc tcttccgatc tgctggagca gatcacacag                                40

<210> SEQ ID NO 191
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
agacgtgtgc tcttccgatc tgggtctgag cagagtaac                                 39

<210> SEQ ID NO 192
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
agacgtgtgc tcttccgatc tgttggctga ggtccaagta t    41

<210> SEQ ID NO 193
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 193
agacgtgtgc tcttccgatc ttcagagtcc ccactagtta    40

COMPOSITIONS AND METHODS FOR SCREENING MUTATIONS IN THYROID CANCER

CROSS-REFERENCE TO RELATED APPLICATIONS

This application is the U.S. National Stage of PCT/US2016/069478, filed Dec. 30, 2016, which claims the benefit of and priority to U.S. Application No. 62/273,783, filed Dec. 31, 2015, and to U.S. Application No. 62/439,572, filed Dec. 28, 2016, the contents of which are incorporated herein by reference in their entireties.

SEQUENCE LISTING

The instant application contains a Sequence Listing which has been filed electronically in ASCII format and is hereby incorporated by reference in its entirety. Said ASCII copy, created on Jun. 27, 2018, is named sequence.txt and is 44 KB in size.

TECHNICAL FIELD

The present technology relates to methods for determining whether a patient having thyroid nodules with indeterminate cytology will benefit from diagnostic surgery, e.g., lobectomy. These methods are based on screening a patient's thyroid nodules and detecting alterations in target nucleic acid sequences corresponding to a specific set of thyroid cancer-related genes. Kits for use in practicing the methods are also provided.

BACKGROUND

The following description of the background of the present technology is provided simply as an aid in understanding the present technology and is not admitted to describe or constitute prior art to the present technology.

Thyroid cancer is the most common malignancy of endocrine organs and its incidence is steadily growing in the U.S. and worldwide. Rahib L et al., *Cancer Res.* 74:2913-2921 (2014). Thyroid cancer typically occurs in thyroid nodules, which are prevalent in the general population, particularly with increased age. However, the vast majority of thyroid nodules are benign. Making an accurate distinction between benign nodules and cancer ensures that patients with cancer receive appropriately definitive treatment and unnecessary treatments, like diagnostic surgery, are avoided for patients with benign nodules. Ultrasound-guided fine-needle aspiration (FNA) of the thyroid nodule followed by cytological examination is a common diagnostic approach that allows detecting cancer or establishing a diagnosis of a benign nodule in most cases. However, 20% to 30% of FNA cytology samples yield 1 of 3 types of indeterminate cytologic diagnoses: atypia of undetermined significance/follicular lesion of undetermined significance (AUS/FLUS), follicular or oncocytic (Hurthle cell) neoplasm/suspicious for a follicular or oncocytic (Hurthle cell) neoplasm (FN/SFN), and suspicious for malignant cells (SUSP), thereby hampering clinical management of these patients. Gharib H. *Endocr Pract.* 10:31-39 (2004); Greaves T S et al., *Cancer* 90:335-341 (2000); Sclabas G M et al., *Am J Surg* 186:702-710 (2003); Cooper D S et al., *Thyroid* 16:109-142 (2006).

Molecular techniques, i.e., a 7-gene panel of the most common mutational markers in thyroid cancer (BRAF, RAS, RET/PTC, PAX8/PPARγ) and Affirma gene expression classifier offer significant diagnostic improvement to FNA cytology, although the overall accuracy of cancer detection by both approaches is not sufficiently high. Nikiforov Y E et al., *J Clin Endocrinol Metab.* 94:2092-2098 (2009); Cantara S et al., *J Clin Endocrinol Metab.* 95:1365-1369 (2010); Ohori N P et al., *Cancer Cytopathol* 0.118:17-23 (2010); Moses W et al., *World J Surg.* 34:2589-2594 (2010); Chudova et al., *J Clin Endocrinol Metab.* (2010); Alexander E K et al., *N Engl J Med.* 367:705-715 (2012).

The detection of genetic alterations in FNA specimens is further complicated by the fact that sclerotic or calcified nodules, as well as nodules with large areas of cystic degeneration or necrosis yield FNA specimens of inadequate quality. Further, the quality of tumor DNA isolated from formalin fixed paraffin-embedded (FFPE) thyroid tissues is often poor because the FFPE process frequently degrades DNA into small fragments and has the potential to damage the DNA base pairs themselves.

Thus, there is a substantial need for more robust and sensitive methods that effectively detect the presence of genetic alterations in thyroid nodule samples, particularly in FFPE tissues and FNA samples. Such methods would aid in predicting whether individual patients would benefit from diagnostic surgery, e.g., lobectomy as well as predicting the overall risk of malignancy within the patient.

SUMMARY OF THE PRESENT TECHNOLOGY

In one aspect, the methods and compositions of the present technology are useful in determining whether a patient having thyroid nodules with indeterminate cytology will benefit from diagnostic surgery (e.g., lobectomy). In some embodiments, the patient is at risk for, or is suspected of having thyroid cancer. It is contemplated that the methods disclosed herein allow for rapid and sensitive detection of mutations in the target nucleic acid sequences of BRAF, NRAS, HRAS, KRAS, PIK3CA, TP53, CTNNB1, PTEN, TSHR, AKT1, GNAS, RET, TERT, and EIF1AX. The present disclosure also provides methods that permit rapid and sensitive detection of translocations in the target nucleic acid sequences of RET, PPARγ, NTRK1, NTRK3, BRAF, MET, LTK, THADA, FGFR2 and ALK.

In one aspect, the present disclosure provides a method for detecting at least one mutation in a plurality of thyroid cancer-related genes in a subject comprising (a) extracting DNA from a FFPE thyroid sample or a FNA thyroid sample obtained from the subject; (b) generating a DNA library of a first plurality of amplicons using a hot start DNA polymerase that substantially lacks 5'-3' exonuclease activity, wherein at least one amplicon corresponds to each of the plurality of thyroid cancer-related genes, said plurality of thyroid cancer-related genes comprising BRAF, NRAS, HRAS, KRAS, PIK3CA, TP53, CTNNB1, PTEN, TSHR, AKT1, GNAS, RET, TERT, and EIF1AX; (c) incorporating an adapter sequence on to the ends of the first plurality of amplicons via polymerase chain reaction; and (d) detecting at least one mutation in at least one of the first plurality of amplicons using high throughput massive parallel sequencing.

In some embodiments of the method, the first plurality of amplicons is generated using at least two primer pairs disclosed in Table 1.

In some embodiments of the method, the at least one mutation detected is a mutation in BRAF, NRAS, HRAS, KRAS, PIK3CA, TP53, CTNNB1, PTEN, TSHR, AKT1, GNAS, RET, TERT, and EIF1AX In one embodiment, the at least one mutation detected is selected from the group consisting of AKT1 E17K, BRAF V600E, BRAF K601E, KRAS G13D, KRAS G12V, KRAS Q61R, KRAS G12D, NRAS Q61R, NRAS Q61K, PIK3CA E545K, PIK3CA H1047R, PIK3CA G914R, HRAS Q61R, RET M918T, TSHR R274W, TSHR A581S, TERT-124 C>T and TERT-146 C>T.

In some embodiments, the first plurality of amplicons is generated using no more than 1 ng of extracted DNA from the FFPE thyroid sample or the FNA thyroid sample. In some embodiments of the method, the first plurality of amplicons is generated using 1-5 ng, 5-10 ng, 10-15 ng, 15-20 ng, 20-25 ng, 1-10 ng, or 1-20 ng of extracted DNA from the FFPE thyroid sample or the FNA thyroid sample. In some embodiments of the method, the first plurality of amplicons is generated using 1-25 ng of extracted DNA from the FFPE thyroid sample or the FNA thyroid sample. In some embodiments of the method, the first plurality of amplicons is generated using at least 25 ng of extracted DNA from the FFPE thyroid sample or the FNA thyroid sample.

Additionally or alternatively, in some embodiments, the method comprises detecting a gene fusion product in one or more of RET, PPARγ, NTRK1, NTRK3, BRAF, MET, LTK, THADA, FGFR2 and ALK in a subject comprising (a) extracting RNA from a FFPE thyroid sample or a FNA thyroid sample obtained from a subject; (b) reverse-transcribing the extracted RNA into cDNA; (c) generating a cDNA library of a second plurality of amplicons using a hot start DNA polymerase with 5'-3' exonuclease activity, wherein at least one amplicon corresponds to each of RET, PPARγ, NTRK1, NTRK3, BRAF, MET, LTK, THADA, FGFR2 and ALK; (d) incorporating an adapter sequence on to the ends of the second plurality of amplicons via polymerase chain reaction; and (e) detecting at least one gene fusion product in at least one of the second plurality of amplicons using high throughput massive parallel sequencing.

In some embodiments of the method, the second plurality of amplicons is generated using at least two or more primers disclosed in Table 2.

In some embodiments of the method, the at least one gene fusion product detected is a translocation in RET, PPARγ, NTRK1, NTRK3, BRAF, MET, LTK, THADA, FGFR2 and ALK. In certain embodiments, the at least one gene fusion product detected is selected from the group consisting of CCDC6 (PTC1) Exon 1/RET Exon 12, PRKAR1A Exon 8/RET Exon 12, NCOA4 Exon 10/RET Exon 12, NCOA4 Exon 9/RET Exon 12, GOLGA5 Exon 7/RET Exon 12, TRIM24 Exon 9/RET Exon 12, TRIM33 (PTC7) Exon 16/RET Exon 12, ERC1 (ELKS) Exon 11/RET Exon 12, KTN1 Exon 30/RET Exon 12, PCM1 Exon 29/RET Exon 12, TRIM27 Exon 3/RET Exon 12, HOOK3 Exon 11/RET Exon 12, CREB3L2 Exon 2/PPARγ Exon 5, PAX8 Exon 7/PPARγ Exon 5, PAX8 Exon 8/PPARγ Exon 5, PAX8 Exon 9/PPARγ Exon 5, PAX8 Exon 10/PPARγ Exon 5, ETV6 Exon 4/NTRK3 Exon 14, BRAF Exon 8/MACF1 Exon 15, AKAP9 Exon 8/BRAF Exon 9, AGK Exon 2/BRAF Exon 8, TFG Exon 5/NTRK1 Exon 12, TPM3 Exon 10/NTRK1 Exon 12, TPR Exon 21/NTRK1 Exon 12, ETV6 Exon 5/NTRK3 Exon 14, STRN Exon 3/ALK Exon 20, EML4 Exon 13/ALK Exon 20, EML4 Exon 20/ALK Exon 20, EML4 Exon 6/ALK Exon 20, TFG Exon 5/MET Exon 15, UACA Exon/LTK Exon 10, AGGF1 Exon 5/RAF1 Exon 8, MACF1 Exon 60/BRAF Exon 9, THADA Exon 27/PPARG Intron 2a, THADA Exon 27/PPARG Intron 2b, THADA Exon 27/Chr 7p non-coding (FUS7p), THADA Exon 28/IGF2BP3 Exon 4, TRA2A Exon 7/THADA Exon 37, FGFR2 Exon 16/OFD1 Exon 3, VCL Exon 1/FGFR2 Exon 18, and SND1 Exon 10/BRAF Exon 9.

In any of the above embodiments, the high throughput massive parallel sequencing is performed using pyrosequencing, reversible dye-terminator sequencing, SOLiD sequencing, Ion semiconductor sequencing, Heliscope single molecule sequencing, sequencing by synthesis, sequencing by ligation, or SMRT™ sequencing.

In any of the above embodiments of the method, the adapter sequence is a P5 adapter, P7 adapter, P1 adapter, A adapter, or Ion Xpress™ barcode adapter.

Additionally or alternatively, in some embodiments, the first plurality of amplicons further comprises a unique index sequence. Additionally or alternatively, in some embodiments, the second plurality of amplicons further comprises a unique index sequence.

In some embodiments of the method, the FNA thyroid sample has been diagnosed as AUS/FLUS, FN/SFN or SUSP. In some embodiments of the method, the hot start DNA polymerase that substantially lacks 5'-3' exonuclease activity is ΔZ05-Gold polymerase or KAPA HiFi. In some embodiments of the method, the hot start DNA polymerase with 5'-3' exonuclease activity is AmpliTaq Gold®.

In another aspect, the present disclosure provides a method for selecting a subject having thyroid nodules with indeterminate cytology for diagnostic surgery comprising: (a) extracting DNA from a FNA thyroid sample obtained from the subject; (b) generating a DNA library of a first plurality of amplicons using a hot start DNA polymerase that substantially lacks 5'-3' exonuclease activity, wherein at least one amplicon corresponds to each of the plurality of thyroid cancer-related genes, said plurality of thyroid cancer-related genes comprising BRAF, NRAS, HRAS, KRAS, PIK3CA, TP53, CTNNB1, PTEN, TSHR, AKT1, GNAS, RET, TERT, and EIF1AX; (c) incorporating an adapter sequence on to the ends of the first plurality of amplicons via polymerase chain reaction; and (d) selecting the subject for diagnostic surgery, if a mutation in at least one of the first plurality of amplicons corresponding to BRAF, NRAS, HRAS, KRAS, PIK3CA, TP53, CTNNB1, PTEN, TSHR, AKT1, RET, TERT, and EIF1AX is detected.

In some embodiments of the method, the first plurality of amplicons is generated using at least two primer pairs disclosed in Table 1.

In some embodiments of the method, the mutation detected is selected from the group consisting of AKT1 E17K, BRAF V600E, BRAF K601E, KRAS G13D, KRAS G12V, KRAS Q61R, KRAS G12D, NRAS Q61R, NRAS Q61K, PIK3CA E545K, PIK3CA H1047R, PIK3CA G914R, HRAS Q61R, RET M918T, TSHR R274W, TSHR A581S, TERT-124 C>T and TERT-146 C>T.

In some embodiments, the first plurality of amplicons is generated using no more than 1 ng of extracted DNA from the FNA thyroid sample. In some embodiments of the method, the first plurality of amplicons is generated using 1-5 ng, 5-10 ng, 10-15 ng, 15-20 ng, 20-25 ng, 1-10 ng, or 1-20 ng of extracted DNA from the FFPE thyroid sample or the FNA thyroid sample. In some embodiments of the method, the first plurality of amplicons is generated using 1-25 ng of extracted DNA from the FNA thyroid sample. In some embodiments of the method, the first plurality of amplicons is generated using at least 25 ng of extracted DNA from the FNA thyroid sample.

Additionally or alternatively, in some embodiments, the method for selecting a subject having thyroid nodules with indeterminate cytology for diagnostic surgery comprises detecting a gene fusion product in one or more of RET, PPARγ, NTRK1, NTRK3, BRAF, MET, LTK, THADA, FGFR2 and ALK in the subject comprising (a) extracting RNA from a FNA thyroid sample obtained from the subject; (b) reverse-transcribing the extracted RNA into cDNA; (c) generating a cDNA library of a second plurality of amplicons using a hot start DNA polymerase with 5'-3' exonuclease activity, wherein at least one amplicon corresponds to each of RET, PPARγ, NTRK1, NTRK3, BRAF, MET, LTK, THADA, FGFR2 and ALK; (d) incorporating an adapter sequence on to the ends of the second plurality of amplicons via polymerase chain reaction; and (e) selecting the subject for diagnostic surgery, if a gene fusion product in at least one of the second plurality of amplicons corresponding to RET, PPARγ, NTRK1, NTRK3, BRAF, MET, LTK, THADA, FGFR2 and ALK is detected.

In some embodiments of the method, the second plurality of amplicons is generated using at least two primers disclosed in Table 2.

In some embodiments of the method, the gene fusion product detected is selected from the group consisting of CCDC6 (PTC1) Exon 1/RET Exon 12, PRKAR1A Exon 8/RET Exon 12, NCOA4 Exon 10/RET Exon 12, NCOA4 Exon 9/RET Exon 12, GOLGA5 Exon 7/RET Exon 12, TRIM24 Exon 9/RET Exon 12, TRIM33 (PTC7) Exon 16/RET Exon 12, ERC1 (ELKS) Exon 11/RET Exon 12, KTN1 Exon 30/RET Exon 12, PCM1 Exon 29/RET Exon 12, TRIM27 Exon 3/RET Exon 12, HOOK3 Exon 11/RET Exon 12, CREB3L2 Exon 2/PPARγ Exon 5, PAX8 Exon 7/PPARγ Exon 5, PAX8 Exon 8/PPARγ Exon 5, PAX8 Exon 9/PPARγ Exon 5, PAX8 Exon 10/PPARγ Exon 5, ETV6 Exon 4/NTRK3 Exon 14, BRAF Exon 8/MACF1 Exon 15, AKAP9 Exon 8/BRAF Exon 9, AGK Exon 2/BRAF Exon 8, TFG Exon 5/NTRK1 Exon 12, TPM3 Exon 10/NTRK1 Exon 12, TPR Exon 21/NTRK1 Exon 12, ETV6 Exon 5/NTRK3 Exon 14, STRN Exon 3/ALK Exon 20, EML4 Exon 13/ALK Exon 20, EML4 Exon 20/ALK Exon 20, EML4 Exon 6/ALK Exon 20, TFG Exon 5/MET Exon 15, UACA Exon 17/LTK Exon 10, AGGF1 Exon 5/RAF1 Exon 8, MACF1 Exon 60/BRAF Exon 9, THADA Exon 27/PPARG Intron 2a, THADA Exon 27/PPARG Intron 2b, THADA Exon 27/Chr 7p non-coding (FUS7p), THADA Exon 28/IGF2BP3 Exon 4, TRA2A Exon 7/THADA Exon 37, FGFR2 Exon 16/OFD1 Exon 3, VCL Exon 1/FGFR2 Exon 18, and SND1 Exon 10/BRAF Exon 9.

In some embodiments of the method, the adapter sequence is a P5 adapter, P7 adapter, P1 adapter, A adapter, or Ion Xpress™ barcode adapter.

Additionally or alternatively, in some embodiments, the first plurality of amplicons further comprises a unique index sequence. Additionally or alternatively, in some embodiments, the second plurality of amplicons further comprises a unique index sequence.

In some embodiments of the method, the FNA thyroid sample has been diagnosed as AUS/FLUS, FN/SFN or SUSP. In some embodiments of the method, the hot start DNA polymerase that substantially lacks 5'-3' exonuclease activity is ΔZ05-Gold polymerase or KAPA HiFi. In some embodiments of the method, the hot start DNA polymerase with 5'-3' exonuclease activity is AmpliTaq Gold®.

In some embodiments of the method, the diagnostic surgery is lobectomy.

In another aspect, the present disclosure provides a method for predicting the risk of malignancy in a subject with inconclusive thyroid FNA cytology results comprising: (a) extracting DNA from a FNA thyroid sample obtained from the subject; (b) generating a DNA library of a first plurality of amplicons using a hot start DNA polymerase that substantially lacks 5'-3' exonuclease activity, wherein at least one amplicon corresponds to each of the plurality of thyroid cancer-related genes, said plurality of thyroid cancer-related genes comprising BRAF, NRAS, HRAS, KRAS, PIK3CA, TP53, CTNNB1, PTEN, TSHR, AKT1, GNAS, RET, TERT, and EIF1AX, (c) incorporating an adapter sequence on to the ends of the first plurality of amplicons via polymerase chain reaction; and (d) identifying the subject as having a high risk of malignancy when a mutation in at least one of the first plurality of amplicons corresponding to BRAF, NRAS, HRAS, KRAS, PIK3CA, TP53, CTNNB1, PTEN, TSHR, AKT1, RET, TERT, and EIF1AX is detected.

Additionally or alternatively, in some embodiments, the method for predicting the risk of malignancy in a subject with inconclusive thyroid FNA cytology results comprises detecting a gene fusion product in one or more of RET, PPARγ, NTRK1, NTRK3, BRAF, MET, LTK, THADA, FGFR2 and ALK in the subject comprising (a) extracting RNA from a FNA thyroid sample obtained from the subject; (b) reverse-transcribing the extracted RNA into cDNA; (c) generating a cDNA library of a second plurality of amplicons using a hot start DNA polymerase with 5'-3' exonuclease activity, wherein at least one amplicon corresponds to each of RET, PPARγ, NTRK1, NTRK3, BRAF, MET, LTK, THADA, FGFR2 and ALK; (d) incorporating an adapter sequence on to the ends of the second plurality of amplicons via polymerase chain reaction; and (e) identifying the subject as having a high risk of malignancy when a gene fusion product in at least one of the second plurality of amplicons corresponding to RET, PPARγ, NTRK1, NTRK3, BRAF, MET, LTK, THADA, FGFR2 and ALK is detected.

In some embodiments of the method, the mutation detected is selected from the group consisting of AKT1 E17K, BRAF V600E, BRAF K601E, KRAS G13D, KRAS G12V, KRAS Q61R, KRAS G12D, NRAS Q61R, NRAS Q61K, PIK3CA E545K, PIK3CA H1047R, PIK3CA G914R, HRAS Q61R, RET M918T, TSHR R274W, TSHR A581S, TERT-124 C>T and TERT-146 C>T. In some embodiments of the method, the gene fusion product detected is selected from the group consisting of CCDC6 (PTC1) Exon 1/RET Exon 12, PRKAR1A Exon 8/RET Exon 12, NCOA4 Exon 10/RET Exon 12, NCOA4 Exon 9/RET Exon 12, GOLGA5 Exon 7/RET Exon 12, TRIM24 Exon 9/RET Exon 12, TRIM33 (PTC1) Exon 16/RET Exon 12, ERC1 (ELKS) Exon 11/RET Exon 12, KTN1 Exon 30/RET Exon 12, PCM1 Exon 29/RET Exon 12, TRIM27 Exon 3/RET Exon 12, HOOK3 Exon 11/RET Exon 12, CREB3L2 Exon 2/PPARγ Exon 5, PAX8 Exon 7/PPARγ Exon 5, PAX8 Exon 8/PPARγ Exon 5, PAX8 Exon 9/PPARγ Exon 5, PAX8 Exon 10/PPARγ Exon 5, ETV6 Exon 4/NTRK3 Exon 14, BRAF Exon 8/MACF1 Exon 15, AKAP9 Exon 8/BRAF Exon 9, AGK Exon 2/BRAF Exon 8, TFG Exon 5/NTRK1 Exon 12, TPM3 Exon 10/NTRK1 Exon 12, TPR Exon 21/NTRK1 Exon 12, ETV6 Exon 5/NTRK3 Exon 14, STRN Exon 3/ALK Exon 20, EML4 Exon 13/ALK Exon 20, EML4 Exon 20/ALK Exon 20, EML4 Exon 6/ALK Exon 20, TFG Exon 5/MET Exon 15, UACA Exon 17/LTK Exon 10, AGGF1 Exon 5/RAF1 Exon 8, MACF1 Exon 60/BRAF Exon 9, THADA Exon 27/PPARG Intron 2a, THADA Exon 27/PPARG Intron 2b, THADA Exon 27/Chr 7p non-coding (FUS7p), THADA Exon 28/IGF2BP3 Exon 4, TRA2A Exon 7/THADA Exon 37, FGFR2 Exon 16/OFD1 Exon 3, VCL Exon 1/FGFR2 Exon 18, and SND1 Exon 10/BRAF Exon 9.

BRIEF DESCRIPTION OF THE DRAWINGS

FIG. 2A shows the final concentration of primer pair sequences disclosed in Table 1. FIG. 2B shows the final concentration of primer pair sequences disclosed in Table 2.

FIG. 3 summarizes the results of a pilot validation study. Residual thyroid specimens, along with 5% Horizon standard mutation mix (Horizon Diagnostics, HDx™ Reference Standards, Cambridge UK) were assayed using the methods disclosed herein. The clinical specimens were previously analyzed via BRAF allele-specific PCR (ASO) and RAS pyrosequencing results.

FIG. 4 shows the intra-assay reproducibility of the thyroid cancer screening Next-Generation Sequencing (NGS) methods of the present technology while detecting single nucleotide variants and insertions/deletions.

FIG. 5 shows the intra-assay reproducibility of the thyroid cancer screening Next-Generation Sequencing (NGS) methods of the present technology while detecting gene fusion products.

FIG. 6 shows the inter-assay reproducibility of the thyroid cancer screening Next-Generation Sequencing (NGS) methods of the present technology while detecting single nucleotide variants and insertions/deletions.

FIG. 7 shows the inter-assay reproducibility of the thyroid cancer screening Next-Generation Sequencing (NGS) methods of the present technology while detecting gene fusion products.

FIG. 8 shows the analytic sensitivity of the thyroid cancer screening Next-Generation Sequencing (NGS) methods of the present technology while detecting single nucleotide variants in a FFPE sample (A) or a FNA sample (B), as well as insertions/deletions in a FFPE sample (C). The expected and observed frequencies (%) at which the different mutant alleles are present within an undiluted or mixed sample are also shown.

FIG. 9 shows the analytic sensitivity of the thyroid cancer screening Next-Generation Sequencing (NGS) methods of the present technology while detecting gene fusion products in a FFPE sample (A) or a FNA sample (B).

FIG. 10 shows the analyte detection limits (minimal DNA input requirement) of the thyroid cancer screening Next-Generation Sequencing (NGS) methods of the present technology while detecting single nucleotide variants in a FFPE sample (A) or a FNA sample (B).

FIG. 11 shows the analyte detection limits (minimal RNA input requirement) of the thyroid cancer screening Next-Generation Sequencing (NGS) methods of the present technology while detecting translocations in a FFPE sample (A) or a FNA sample (B).

FIG. 12 (A) shows the overall recovery of known variants in a Horizon mutation mix control sample (Horizon Diagnostics, HDx™ Reference Standards, Cambridge UK) using the screening methods disclosed herein. FIG. 12 (B) shows the acceptable frequency range (%) of known variants as determined by mean±2SD.

FIG. 13 (A) provides a comparison of the results obtained when employing the NGS-based thyroid cancer screening methods of the present technology and the 7-gene panel for thyroid cancer (BRAF, RAS, RET/PTC1/3, PAX8/PPARγ) for 40 thyroid clinical specimens and 8 non-thyroid FFPE specimens. FIG. 13 (B) summarizes the results for the 40 thyroid clinical specimens that were assayed via the NGS-based thyroid cancer screening methods of the present technology and the 7-gene panel for thyroid cancer. The 2-step PCR method screened for mutations in BRAF, NRAS, HRAS, KRAS, PIK3CA, TP53, CTNNB1, P TEN, TSHR, AKT1, GNAS, RET, TERT, and EIF1AX, and translocations in RET, PPARγ, NTRK1, NTRK3, BRAF, MET, LTK, and ALK.

FIG. 15(A) shows the recovery of select RET, PPARγ, NTRK1, NTRK3, BRAF, MET, LTK, and ALK translocation variants from gBlock fusion fragments having assay input copies ranging from 100-2000. FIG. 15(B) shows the recovery of THADA and FGFR2 translocation variants from gBlock fusion fragments (400 input copies).

DETAILED DESCRIPTION

Figure 1:
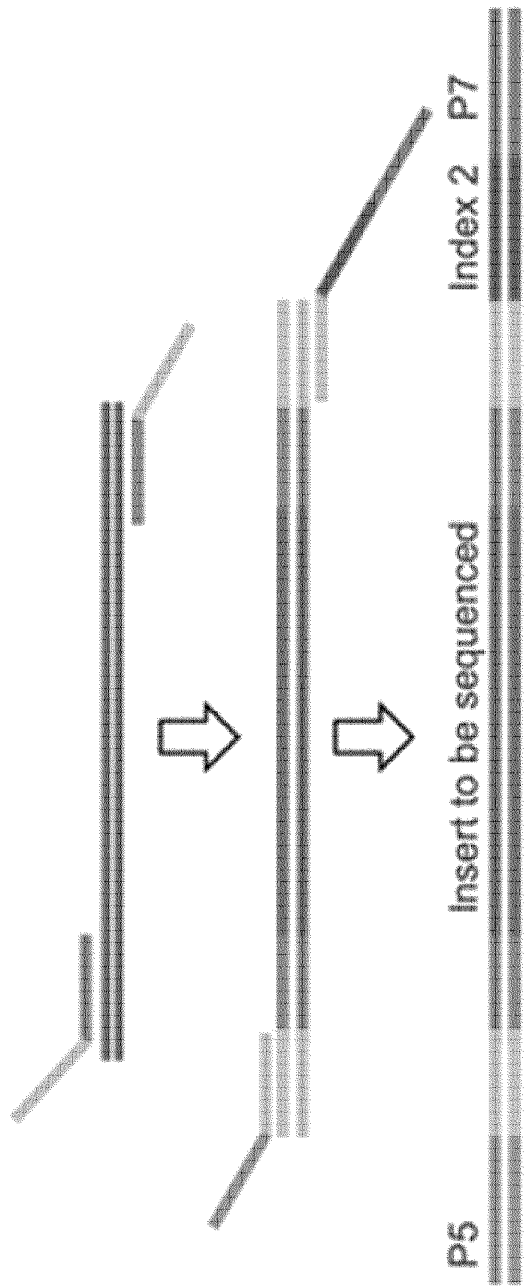
FIG. 1 shows the two-step PCR protocol for target-specific amplification and library preparation for the methods of the present technology.

The present disclosure provides methods for determining whether a patient having thyroid nodules with indeterminate cytology will benefit from diagnostic surgery, e.g., lobectomy. These methods are based on screening a patient's thyroid nodules and detecting alterations in target nucleic acid sequences corresponding to a specific set of thyroid cancer-related genes using a highly sensitive PCR-based NGS assay. Kits for use in practicing the methods are also provided.

FFPE specimens are integral to the diagnosis of virtually every suspected cancer case, and the estimated millions of archived samples can provide a wealth of molecular information about disease progression and treatment. While FFPE techniques are the standard for protecting tissues for downstream molecular analysis and ease of archiving, storage of tissues in formaldehyde solution results in extensive crosslinking of proteins to other proteins and to nucleic acids and in nucleic acid fragmentation. FFPE techniques can result in the partial denaturation of the DNA and may cause damage to the DNA base pairs themselves, thereby compromising the accuracy of NGS assays. Moreover, the amount of total nucleic acid material available in thyroid biopsy specimens is often limited (<10 ng DNA and RNA combined), thereby making the detection of genetic alterations in FFPE tissues or FNA samples extremely difficult. Traditional NGS protocols generally require at least 10-50 ng of nucleic acid input.

One objective of the present technology was to develop a highly sensitive PCR-based NGS screening assay that is economical in terms of its total nucleic acid input requirement from FFPE samples and FNA samples, and can simultaneously detect a broad range of mutations in specifically targeted exons, promoter regions, or other gene regions of a preselected set of thyroid cancer-related genes.

In one aspect, the methods disclosed herein require less DNA input from FFPE specimens or FNA samples, compared to other existing NGS PCR-based thyroid cancer screening assays.

The methods disclosed herein are useful in predicting whether a patient is at risk for having thyroid cancer, or predicting whether a patient risk for having suspected of having thyroid cancer will benefit from diagnostic surgery, e.g., lobectomy. Further, the methods of the present technology are useful in predicting the risk of malignancy in a subject having thyroid nodules with indeterminate cytology. Accordingly, DNA degradation/partial DNA denaturation during the FFPE process does not appear to influence the sensitivity of the screening assay of the present technology.

Definitions

As used herein, the term "about" in reference to a number is generally taken to include numbers that fall within a range of +/−1%-5% (greater than or less than 1%-5%) of the number unless otherwise stated or otherwise evident from the context.

As used herein, the terms "amplify" or "amplification" with respect to nucleic acid sequences, refer to methods that increase the representation of a population of nucleic acid sequences in a sample. Nucleic acid amplification methods, such as PCR, isothermal methods, rolling circle methods, etc., are well known to the skilled artisan. Copies of a particular nucleic acid sequence generated in vitro in an amplification reaction are called "amplicons" or "amplification products".

The term "adapter" refers to a short, chemically synthesized, nucleic acid sequence which can be used to ligate to the end of a nucleic acid sequence in order to facilitate attachment to another molecule. The adapter can be single-stranded or double-stranded. An adapter can incorporate a short (typically less than 50 base pairs) sequence useful for PCR amplification or sequencing.

As used herein, an "alteration" of a gene or gene product (e.g., a marker gene or gene product) refers to the presence of a mutation or mutations within the gene or gene product, e.g., a mutation, which affects the quantity or activity of the gene or gene product, as compared to the normal or wild-type gene. The genetic alteration can result in changes in the quantity, structure, and/or activity of the gene or gene product in a cancer tissue or cancer cell, as compared to its quantity, structure, and/or activity, in a normal or healthy tissue or cell (e.g., a control). For example, an alteration which is associated with thyroid cancer, can have an altered nucleotide sequence (e.g., a mutation), amino acid sequence, chromosomal translocation, intra-chromosomal inversion, copy number, expression level, protein level, protein activity, in a cancer tissue or cancer cell, as compared to a normal, healthy tissue or cell. Exemplary mutations include, but are not limited to, point mutations (e.g., silent, missense, or nonsense), deletions, insertions, inversions, linking mutations, duplications, translocations, inter- and intra-chromosomal rearrangements. Mutations can be present in the coding or non-coding region of the gene. In certain embodiments, the alterations are associated with a phenotype, e.g., a cancerous phenotype (e.g., one or more of thyroid cancer risk, progression, or responsiveness to treatment). In one embodiment, the alteration is associated with one or more of: a genetic risk factor for thyroid cancer, a positive treatment response predictor, a negative treatment response predictor, a positive prognostic factor, a negative prognostic factor, or a diagnostic factor.

The terms "cancer" or "tumor" are used interchangeably and refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells can exist alone within an animal, or can be a non-tumorigenic cancer cell. As used herein, the term "cancer" includes premalignant, as well as malignant cancers. In some embodiments, the cancer is thyroid cancer.

The terms "complementary" or "complementarity" as used herein with reference to polynucleotides (i.e., a sequence of nucleotides such as an oligonucleotide or a target nucleic acid) refer to the base-pairing rules. The complement of a nucleic acid sequence as used herein refers to an oligonucleotide which, when aligned with the nucleic acid sequence such that the 5' end of one sequence is paired with the 3' end of the other, is in "antiparallel association." For example, the sequence "5'-A-G-T-3'" is complementary to the sequence "3'-T-C-A-5.'" Certain bases not commonly found in naturally-occurring nucleic acids may be included in the nucleic acids described herein. These include, for example, inosine, 7-deazaguanine, Locked Nucleic Acids (LNA), and Peptide Nucleic Acids (PNA). Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complement sequence can also be an RNA sequence complementary to the DNA sequence or its complement sequence, and can also be a cDNA.

As used herein, a "control" is an alternative sample used in an experiment for comparison purpose. A control can be "positive" or "negative." A "control nucleic acid sample" or "reference nucleic acid sample" as used herein, refers to nucleic acid molecules from a control or reference sample. In certain embodiments, the reference or control nucleic acid sample is a wild type or a non-mutated DNA or RNA sequence. In certain embodiments, the reference nucleic acid sample is purified or isolated (e.g., it is removed from its natural state). In other embodiments, the reference nucleic acid sample is from a non-tumor sample, e.g., a normal adjacent tumor (NAT), or any other non-cancerous sample from the same or a different subject.

"Detecting" as used herein refers to determining the presence of a mutation or alteration in a nucleic acid of interest in a sample. Detection does not require the method to provide 100% sensitivity.

"Gene" as used herein refers to a DNA sequence that comprises regulatory and coding sequences necessary for the production of an RNA, which may have a non-coding function (e.g., a ribosomal or transfer RNA) or which may include a polypeptide or a polypeptide precursor. The RNA or polypeptide may be encoded by a full length coding sequence or by any portion of the coding sequence so long as the desired activity or function is retained. Although a sequence of the nucleic acids may be shown in the form of DNA, a person of ordinary skill in the art recognizes that the corresponding RNA sequence will have a similar sequence with the thymine being replaced by uracil, i.e., "T" is replaced with "U."

A "hot start", in the context of a nucleic acid amplification reaction, refers to a protocol, where at least one critical reagent is withheld from the reaction mixture (or, if present in the reaction mixture, the reagent remains inactive) until the temperature is raised sufficiently to provide the necessary hybridization specificity of the primer or primers. A "hot start enzyme" is an enzyme, typically a nucleic acid polymerase, capable of acting as the "withheld" or inactive reagent in a hot start protocol. For example, some hot start enzymes can be obtained by chemically modifying the enzyme. Examples of hot-start enzymes include ΔZ05-Gold polymerase, KAPA HiFi and AmpliTaq Gold®.

The term "5'-3' exonuclease activity" refers to an activity of a nucleic acid polymerase, typically associated with the nucleic acid strand synthesis, whereby nucleotides are removed from the 5' end of nucleic acid strand, e.g., *E. coli* DNA polymerase I has this activity, whereas the Klenow fragment does not.

A polymerase that "substantially lacks 5'-3' exonuclease activity" refers to a polymerase that has 50% or less (e.g., <25%, <20%, <15%, <10%) 5'-3' exonuclease activity than Taq DNA polymerase. Methods of measuring 5'-3' exonuclease activity and conditions for measurement are described in, for example, U.S. Pat. No. 5,466,591. Examples of DNA polymerases substantially lacking 5' to 3' exonuclease activity include the Klenow fragment of *E. coli* DNA polymerase I; a *Thermus aquaticus* DNA polymerase (Taq) lacking the N-terminal 235 amino acids (e.g., as described in U.S. Pat. No. 5,616,494 and commonly referred to in the art as the "Stoffel fragment"). Other examples include a thermostable DNA polymerase having sufficient deletions (e.g., N-terminal deletions), mutations, or modifications so as to eliminate or inactivate the domain responsible for the 5'-3' exonuclease activity, such as Δ705 polymerase, Δ705-Gold polymerase etc. See, e.g., U.S. Pat. No. 5,795,762.

The term "hybridize" as used herein refers to a process where two substantially complementary nucleic acid strands (at least about 65% complementary over a stretch of at least 14 to 25 nucleotides, at least about 75%, or at least about 90% complementary) anneal to each other under appropriately stringent conditions to form a duplex or heteroduplex through formation of hydrogen bonds between complementary base pairs. Hybridizations are typically and preferably conducted with probe-length nucleic acid molecules, preferably 15-100 nucleotides in length, more preferably 18-50 nucleotides in length. Nucleic acid hybridization techniques are described in Sambrook, et al., 1989, *Molecular Cloning: A Laboratory Manual*, Second Edition, Cold Spring Harbor Press, Plainview, N.Y. Hybridization and the strength of hybridization (i.e., the strength of the association between the nucleic acids) is influenced by such factors as the degree of complementarity between the nucleic acids, stringency of the conditions involved, and the thermal melting point ($T_m$) of the formed hybrid. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, *Molecular Cloning: A Laboratory Manual*, Second Edition, Cold Spring Harbor Press, Plainview, N.Y.; Ausubel, F. M. et al. 1994, *Current Protocols in Molecular Biology*, John Wiley & Sons, Secaucus, N.J. In some embodiments, specific hybridization occurs under stringent hybridization conditions. An oligonucleotide or polynucleotide (e.g., a probe or a primer) that is specific for a target nucleic acid will "hybridize" to the target nucleic acid under suitable conditions.

As used herein, the terms "individual", "patient", or "subject" are used interchangeably and refer to an individual organism, a vertebrate, a mammal, or a human. In a preferred embodiment, the individual, patient or subject is a human.

As used herein, the term "library" refers to a collection of nucleic acid sequences, e.g., a collection of nucleic acids derived from whole genomic, subgenomic fragments, cDNA, cDNA fragments, RNA, RNA fragments, or a combination thereof. In one embodiment, a portion or all of the library nucleic acid sequences comprises an adapter sequence. The adapter sequence can be located at one or both ends. The adapter sequence can be useful, e.g., for a sequencing method (e.g., an NGS method), for amplification, for reverse transcription, or for cloning into a vector.

The library can comprise a collection of nucleic acid sequences, e.g., a target nucleic acid sequence (e.g., a tumor nucleic acid sequence), a reference nucleic acid sequence, or a combination thereof). In some embodiments, the nucleic acid sequences of the library can be derived from a single subject. In other embodiments, a library can comprise nucleic acid sequences from more than one subject (e.g., 2, 3, 4, 5, 6, 7, 8, 9, 10, 20, 30 or more subjects). In some embodiments, two or more libraries from different subjects can be combined to form a library having nucleic acid sequences from more than one subject. In one embodiment, the subject is human having, or at risk of having, a cancer or tumor.

A "library nucleic acid sequence" refers to a nucleic acid molecule, e.g., a DNA, RNA, or a combination thereof, that is a member of a library. Typically, a library nucleic acid sequence is a DNA molecule, e.g., genomic DNA or cDNA. In some embodiments, a library nucleic acid sequence is fragmented, e.g., sheared or enzymatically prepared, genomic DNA. In certain embodiments, the library nucleic acid sequences comprise sequence from a subject and sequence not derived from the subject, e.g., adapter sequence, a primer sequence, or other sequences that allow for identification, e.g., "barcode" sequences.

The term "multiplex PCR" as used herein refers to amplification of two or more PCR products or amplicons which are each primed using a distinct primer pair.

"Next-generation sequencing or NGS" as used herein, refers to any sequencing method that determines the nucleotide sequence of either individual nucleic acid molecules (e.g., in single molecule sequencing) or clonally expanded proxies for individual nucleic acid molecules in a high throughput parallel fashion (e.g., greater than $10^3$, $10^4$, $10^5$ or more molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are described, e.g., in Metzker, M. *Nature Biotechnology Reviews* 11:31-46 (2010).

As used herein, "oligonucleotide" refers to a molecule that has a sequence of nucleic acid bases on a backbone comprised mainly of identical monomer units at defined intervals. The bases are arranged on the backbone in such a way that they can bind with a nucleic acid having a sequence of bases that are complementary to the bases of the oligonucleotide. The most common oligonucleotides have a backbone of sugar phosphate units. A distinction may be made between oligodeoxyribonucleotides that do not have a hydroxyl group at the 2' position and oligoribonucleotides that have a hydroxyl group at the 2' position. Oligonucleotides may also include derivatives, in which the hydrogen of the hydroxyl group is replaced with organic groups, e.g., an allyl group. Oligonucleotides of the method which function as primers or probes are generally at least about 10-15 nucleotides long and more preferably at least about 15 to 25 nucleotides long, although shorter or longer oligonucleotides may be used in the method. The exact size will depend on many factors, which in turn depend on the ultimate function or use of the oligonucleotide. The oligonucleotide may be generated in any manner, including, for example, chemical synthesis, DNA replication, restriction endonuclease digestion of plasmids or phage DNA, reverse transcription, PCR, or a combination thereof. The oligonucleotide may be modified e.g., by addition of a methyl group, a biotin or digoxigenin moiety, a fluorescent tag or by using radioactive nucleotides.

As used herein, the term "primer" refers to an oligonucleotide, which is capable of acting as a point of initiation of nucleic acid sequence synthesis when placed under conditions in which synthesis of a primer extension product which is complementary to a target nucleic acid strand is induced, i.e., in the presence of different nucleotide triphosphates and a polymerase in an appropriate buffer ("buffer" includes pH, ionic strength, cofactors etc.) and at a suitable temperature. One or more of the nucleotides of the primer can be modified for instance by addition of a methyl group, a biotin or digoxigenin moiety, a fluorescent tag or by using radioactive nucleotides. A primer sequence need not reflect the exact sequence of the template. For example, a non-complementary nucleotide fragment may be attached to the 5' end of the primer, with the remainder of the primer sequence being substantially complementary to the strand. The term primer as used herein includes all forms of primers that may be synthesized including peptide nucleic acid primers, locked nucleic acid primers, phosphorothioate modified primers, labeled primers, and the like. The term "forward primer" as used herein means a primer that anneals to the anti-sense strand of dsDNA. A "reverse primer" anneals to the sense-strand of dsDNA.

As used herein, "primer pair" refers to a forward and reverse primer pair (i.e., a left and right primer pair) that can be used together to amplify a given region of a nucleic acid of interest.

As used herein, a "sample" refers to a substance that is being assayed for the presence of a mutation in a nucleic acid of interest. Processing methods to release or otherwise make available a nucleic acid for detection may include steps of nucleic acid manipulation. A biological sample may be a body fluid or a tissue sample. In some cases, a biological sample may consist of or comprise blood, plasma, sera, urine, feces, epidermal sample, vaginal sample, skin sample, cheek swab, sperm, amniotic fluid, cultured cells, bone marrow sample, tumor biopsies, aspirate and/or chorionic villi, cultured cells, and the like. Fresh, fixed or frozen tissues may also be used. In one embodiment, the sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample. Whole blood samples of about 0.5 to 5 ml collected with EDTA, ACD or heparin as anti-coagulant are suitable. In some embodiments, the sample is a FNA sample.

The term "sensitivity," as used herein in reference to the methods of the present technology, is a measure of the ability of a method to detect a preselected sequence variant in a heterogeneous population of sequences. A method has a sensitivity of S % for variants of F % if, given a sample in which the preselected sequence variant is present as at least F % of the sequences in the sample, the method can detect the preselected sequence at a preselected confidence of C %, S % of the time. By way of example, a method has a sensitivity of 90% for variants of 5% if, given a sample in which the preselected variant sequence is present as at least 5% of the sequences in the sample, the method can detect the preselected sequence at a preselected confidence of 99%, 9 out of 10 times (F=5%; C=99%; S=90%).

The term "specific" as used herein in reference to an oligonucleotide primer means that the nucleotide sequence of the primer has at least 12 bases of sequence identity with a portion of the nucleic acid to be amplified when the oligonucleotide and the nucleic acid are aligned. An oligonucleotide primer that is specific for a nucleic acid is one that, under the stringent hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% sequence identity.

"Specificity," as used herein, is a measure of the ability of a method to distinguish a truly occurring preselected sequence variant from sequencing artifacts or other closely related sequences. It is the ability to avoid false positive detections. False positive detections can arise from errors introduced into the sequence of interest during sample preparation, sequencing error, or inadvertent sequencing of closely related sequences like pseudo-genes or members of a gene family. A method has a specificity of X % if, when applied to a sample set of $N_{Total}$ sequences, in which $X_{True}$ sequences are truly variant and $X_{Not\ true}$ are not truly variant, the method selects at least X % of the not truly variant as not variant. E.g., a method has a specificity of 90% if, when applied to a sample set of 1,000 sequences, in which 500 sequences are truly variant and 500 are not truly variant, the method selects 90% of the 500 not truly variant sequences as not variant. Exemplary specificities include 90, 95, 98, and 99%.

The term "stringent hybridization conditions" as used herein refers to hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5×Denhart's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids which differ over a stretch of 20 contiguous nucleotides by more than two bases.

As used herein, the terms "target sequence" and "target nucleic acid sequence" refer to a specific nucleic acid sequence to be detected and/or quantified in the sample to be analyzed.

As used herein, the terms "treat," "treating" or "treatment" refer, to an action to obtain a beneficial or desired clinical result including, but not limited to, alleviation or amelioration of one or more signs or symptoms of a disease or condition (e.g., regression, partial or complete), diminishing the extent of disease, stability (i.e., not worsening, achieving stable disease) state of disease, amelioration or palliation of the disease state, diminishing rate of or time to progression, and remission (whether partial or total).

Thyroid Cancer

The most common mutations that occur in papillary thyroid cancer (PTC) are point mutations in BRAF and RAS, and RET/PTC and NTRK1 rearrangements, all of which are capable of activating the mitogen-activated protein kinase (MAPK) pathway. These mutually exclusive mutations are found in more than 70% of PTC. Adeniran A J et al., *Am J Surg Pathol.* 30:216-222 (2006); Kimura E T et al., *Cancer Res.* 63:1454-1457 (2003); Soares P et al., *Oncogene* 22:4578-4580 (2003); Frattini M et al., *Oncogene* 23:7436-7440 (2004). The most common aberrations in follicular thyroid cancer are either RAS mutations or PAX8/PPARγ rearrangements. These mutations are also mutually exclusive and manifest in 70%-75% of follicular carcinomas. Nikiforova M N et al., *J Clin Endocrinol Metab.* 88:2318-2326 (2003).

Genetic alterations involving the PI3K/AKT signaling pathway also occur in thyroid tumors, particularly in advanced and dedifferentiating tumors. Garcia-Rostan G et al., *Cancer Res.* 65:10199-10207 (2005); Santarpia L et al., *J Clin Endocrinol Metab.* 93:278-284 (2008); Hou P et al., *Clin Cancer Res.* 13:1161-1170 (2007). Additional mutations known to occur in poorly differentiated and anaplastic carcinomas involve TP53, AKT1 and CTNNB1. Kondo T et al., *Nat Rev Cancer* 6:292-306 (2006). Medullary thyroid carcinomas, both familial and sporadic, frequently carry point mutations located in RET and RAS. de Groot J W et al., *Endocr Rev.* 27:535-560 (2006); Moura M M et al., *J Clin Endocrinol Metab.* 96:E863-868 (2011). Other somatic mutations, such as those in the TSHR gene, have been reported in some thyroid nodules, although their prevalence and diagnostic utility remain unclear. Garcia-Jimenez C & Santisteban P. *Arq Bras Endocrinol Metabol.* 51:654-671 (2007); Nishihara E et al., *Endocr J.* 56:791-798 (2009).

NGS Platforms

In some embodiments, high throughput, massively parallel sequencing employs sequencing-by-synthesis with reversible dye terminators. In other embodiments, sequencing is performed via sequencing-by-ligation. In yet other embodiments, sequencing is single molecule sequencing. Examples of Next Generation Sequencing techniques include, but are not limited to pyrosequencing, Reversible dye-terminator sequencing, SOLiD sequencing, Ion semiconductor sequencing, Helioscope single molecule sequencing etc.

The Ion Torrent™ (Life Technologies, Carlsbad, Calif.) amplicon sequencing system employs a flow-based approach that detects pH changes caused by the release of hydrogen ions during incorporation of unmodified nucleotides in DNA replication. For use with this system, a sequencing library is initially produced by generating DNA fragments flanked by sequencing adapters. In some embodiments, these fragments can be clonally amplified on particles by emulsion PCR. The particles with the amplified template are then placed in a silicon semiconductor sequencing chip. During replication, the chip is flooded with one nucleotide after another, and if a nucleotide complements the DNA molecule in a particular microwell of the chip, then it will be incorporated. A proton is naturally released when a nucleotide is incorporated by the polymerase in the DNA molecule, resulting in a detectable local change of pH. The pH of the solution then changes in that well and is detected by the ion sensor. If homopolymer repeats are present in the template sequence, multiple nucleotides will be incorporated in a single cycle. This leads to a corresponding number of released hydrogens and a proportionally higher electronic signal.

The 454™ GS FLX™ sequencing system (Roche, Germany), employs a light-based detection methodology in a large-scale parallel pyrosequencing system. Pyrosequencing uses DNA polymerization, adding one nucleotide species at a time and detecting and quantifying the number of nucleotides added to a given location through the light emitted by the release of attached pyrophosphates. For use with the 454™ system, adapter-ligated DNA fragments are fixed to small DNA-capture beads in a water-in-oil emulsion and amplified by PCR (emulsion PCR). Each DNA-bound bead is placed into a well on a picotiter plate and sequencing reagents are delivered across the wells of the plate. The four DNA nucleotides are added sequentially in a fixed order across the picotiter plate device during a sequencing run. During the nucleotide flow, millions of copies of DNA bound to each of the beads are sequenced in parallel. When a nucleotide complementary to the template strand is added to a well, the nucleotide is incorporated onto the existing DNA strand, generating a light signal that is recorded by a CCD camera in the instrument.

Sequencing technology based on reversible dye-terminators: DNA molecules are first attached to primers on a slide and amplified so that local clonal colonies are formed. Four types of reversible terminator bases (RT-bases) are added, and non-incorporated nucleotides are washed away. Unlike pyrosequencing, the DNA can only be extended one nucleotide at a time. A camera takes images of the fluorescently labeled nucleotides, then the dye along with the terminal 3' blocker is chemically removed from the DNA, allowing the next cycle.

Helicos's single-molecule sequencing uses DNA fragments with added polyA tail adapters, which are attached to the flow cell surface. At each cycle, DNA polymerase and a single species of fluorescently labeled nucleotide are added, resulting in template-dependent extension of the surface-immobilized primer-template duplexes. The reads are performed by the Helioscope sequencer. After acquisition of images tiling the full array, chemical cleavage and release of the fluorescent label permits the subsequent cycle of extension and imaging.

Sequencing by synthesis (SBS), like the "old style" dye-termination electrophoretic sequencing, relies on incorporation of nucleotides by a DNA polymerase to determine the base sequence. A DNA library with affixed adapters is denatured into single strands and grafted to a flow cell, followed by bridge amplification to form a high-density array of spots onto a glass chip. Reversible terminator methods use reversible versions of dye-terminators, adding one nucleotide at a time, detecting fluorescence at each position by repeated removal of the blocking group to allow polymerization of another nucleotide. The signal of nucleotide incorporation can vary with fluorescently labeled nucleotides, phosphate-driven light reactions and hydrogen ion sensing having all been used. Examples of SBS platforms include Illumina GA and HiSeq 2000. The MiSeq® personal sequencing system (Illumina, Inc.) also employs sequencing by synthesis with reversible terminator chemistry.

In contrast to the sequencing by synthesis method, the sequencing by ligation method uses a DNA ligase to determine the target sequence. This sequencing method relies on enzymatic ligation of oligonucleotides that are adjacent through local complementarity on a template DNA strand. This technology employs a partition of all possible oligonucleotides of a fixed length, labeled according to the sequenced position. Oligonucleotides are annealed and ligated and the preferential ligation by DNA ligase for matching sequences results in a dinucleotide encoded color space signal at that position (through the release of a fluorescently labeled probe that corresponds to a known nucleotide at a known position along the oligo). This method is primarily used by Life Technologies' SOLiD™ sequencers. Before sequencing, the DNA is amplified by emulsion PCR. The resulting beads, each containing only copies of the same DNA molecule, are deposited on a solid planar substrate.

SMRT™ sequencing is based on the sequencing by synthesis approach. The DNA is synthesized in zero-mode wave-guides (ZMWs)-small well-like containers with the capturing tools located at the bottom of the well. The sequencing is performed with use of unmodified polymerase (attached to the ZMW bottom) and fluorescently labeled nucleotides flowing freely in the solution. The wells are constructed in a way that only the fluorescence occurring at the bottom of the well is detected. The fluorescent label is detached from the nucleotide at its incorporation into the DNA strand, leaving an unmodified DNA strand.

Thyroid Cancer Screening Methods of the Present Technology

Disclosed herein are methods and assays that are based, at least in part, on a pre-selected set of genes that are associated with thyroid cancer. Such pre-selected genes enable the application of sequencing methods, particularly methods that rely on massively parallel sequencing of a large number of diverse genes, e.g., from thyroid tumor samples or control samples.

In one embodiment, the methods featured in the present technology are used in a multiplex, multi-gene assay format, e.g., assays that incorporate multiple signals from a large number of diverse genetic alterations in a large number of genes.

The methods of the present technology are based on the principle that screening a patient's thyroid nodules for the presence of one or more alterations in a preselected set of thyroid cancer-related genes is useful in determining whether a patient will benefit from diagnostic surgery (e.g., lobectomy), wherein the preselected set of thyroid cancer-related genes corresponds to BRAF, NRAS, HRAS, KRAS, PIK3CA, TP53, CTNNB1, PTEN, TSHR, AKT1, GNAS, RET, TERT, and EIF1AX. In some embodiments of the method, the presence of one or more mutations in BRAF, NRAS, HRAS, KRAS, PIK3CA, TP53, CTNNB1, PTEN, TSHR, AKT1, GNAS, RET, TERT, and EIF1AX is detected by assaying a plurality of amplicons, wherein at least one amplicon corresponds to each of BRAF, NRAS, HRAS, KRAS, PIK3CA, TP53, CTNNB1, PTEN, TSHR, AKT1, GNAS, RET, TERT, and EIF1AX. Additionally or alternatively, in some embodiments, the method comprises screening a patient's thyroid nodules for the presence of translocations in one or more genes selected from the group consisting of RET, PPARγ, NTRK1, NTRK3, BRAF, MET, LTK, THADA, FGFR2 and ALK.

A significant advantage of the methods of the present technology over other comparable PCR-based NGS screening panels is that the minimal DNA input required for the screening assays disclosed herein is about five to ten times lower than other comparable thyroid cancer screening panels. For example, the minimal DNA input for the methods disclosed herein is 1 ng, whereas other NGS protocols require at least 10 ng (e.g., ThyroSeq panel). The 2-step PCR approach employed in the methods of the present technology permits improved enrichment of the limited genetic material (DNA and RNA) that can be isolated from FFPE or FNA thyroid samples, and is highly sensitive in detecting clinically relevant genetic alterations that are implicated in thyroid cancer. The methods of the present technology also forego the need to perform nick translation and adapter ligation steps during DNA or cDNA library generation, thereby making the disclosed methods less time consuming and more cost-effective.

In one aspect, the present disclosure provides methods for detecting at least one mutation in a plurality of thyroid cancer-related genes in a subject comprising (a) extracting DNA from a FFPE thyroid sample or a FNA thyroid sample obtained from the subject; (b) generating a DNA library of a first plurality of amplicons using a hot start DNA polymerase that substantially lacks 5'-3' exonuclease activity, wherein at least one amplicon corresponds to each of the plurality of thyroid cancer-related genes, said plurality of thyroid cancer-related genes comprising BRAF, NRAS, HRAS, KRAS, PIK3CA, TP53, CTNNB1, PTEN, TSHR, AKT1, GNAS, RET, TERT, and EIF1AX; (c) incorporating an adapter sequence on to the ends of the first plurality of amplicons via polymerase chain reaction; and (d) detecting at least one mutation in at least one of the first plurality of amplicons using high throughput massive parallel sequencing.

In some embodiments of the method, the at least one mutation detected is a mutation in BRAF, NRAS, HRAS, KRAS, PIK3CA, TP53, CTNNB1, PTEN, TSHR, AKT1, GNAS, RET, TERT, and EIF1AX In one embodiment, the at least one mutation detected is selected from the group consisting of AKT1 E17K, BRAF V600E, BRAF K601E, KRAS G13D, KRAS G12V, KRAS Q61R, KRAS G12D, NRAS Q61R, NRAS Q61K, PIK3CA E545K, PIK3CA H1047R, PIK3CA G914R, HRAS Q61R, RET M918T, TSHR R274W, TSHR A581S, TERT-124 C>T and TERT-146 C>T.

In some embodiments, the first plurality of amplicons is generated using no more than 1 ng of extracted DNA from the FFPE thyroid sample or the FNA thyroid sample. In some embodiments of the method, the first plurality of amplicons is generated using 1-5 ng, 5-10 ng, 10-15 ng, 15-20 ng, 20-25 ng, 1-10 ng, or 1-20 ng of extracted DNA from the FFPE thyroid sample or the FNA thyroid sample. In some embodiments of the method, the first plurality of amplicons is generated using 1-25 ng of extracted DNA from the FFPE thyroid sample or the FNA thyroid sample. In some embodiments of the method, the first plurality of amplicons is generated using at least 25 ng of extracted DNA from the FFPE thyroid sample or the FNA thyroid sample.

In some embodiments of the method, the FNA thyroid sample has been diagnosed as AUS/FLUS, FN/SFN or SUSP. In some embodiments of the method, the hot start DNA polymerase that substantially lacks 5'-3' exonuclease activity is ΔZ05-Gold polymerase or KAPA HiFi.

In some embodiments of the method, the first plurality of amplicons is generated using primer pairs that recognize and specifically hybridize to one or more of exon 15 of BRAF, exon 2, 3 or 4 of NRAS, exon 2, 3 or 4 of HRAS, exon 2, 3 or 4 of KRAS, exon 10 or 21 of PIK3CA, exon 5, 6, 7, 8 or 9 of TP53, exon 3 of CTNNB1, exon 5, 6, 7, or 8 of PTEN, exon 9 or 10 of TSHR, exon 3 of AKT1, exon 8 or 9 of GNAS, exon 10, 11, 12, 13 or 15 of RET, the promoter of TERT, and exon 2, 5 or 6 of EIF1AX.

In some embodiments of the method, the first plurality of amplicons is generated using at least two, at least three, at least four, at least five, at least ten, at least fifteen, at least twenty, or at least twenty-five or more pairs of primers disclosed in Table 1.

TABLE 1

Primer Pairs for DNA Library

| Primer Name | Sequence (5'→3') (SEQ ID NOS 1-118, respectively, in order of appearance) |
|---|---|
| AKT1_01B_FWD_TAG | CGACGCTCTTCCGATCTTCACGTTGGTCCACATC |
| AKT1_01B_REV_TAG | AGACGTGTGCTCTTCCGATCTGGTCTGACGGGTAGAGT |

TABLE 1-continued

Primer Pairs for DNA Library

| Primer Name | Sequence (5'→3') (SEQ ID NOS 1-118, respectively, in order of appearance) |
|---|---|
| BRAF_01_FWD_TAG | CGACGCTCTTCCGATCTTGGAAAAATAGCCTCAATTCT |
| BRAF_01_REV_TAG | AGACGTGTGCTCTTCCGATCTTGTTTTCCTTTACTTACTACACC |
| BRAF_02_FWD_TAG | CGACGCTCTTCCGATCTAGACAACTGTTCAAACTGAT |
| BRAF_02_REV_TAG | AGACGTGTGCTCTTCCGATCTATGCTTGCTCTGATAGGA |
| CTNNB1_04_FWD_TAG | CGACGCTCTTCCGATCTGCGGCTGTTAGTCACT |
| CTNNB1_04_REV_TAG | AGACGTGTGCTCTTCCGATCTTCCCTGTTCCCACTCATA |
| EIF1AX_01_FWD_TAG | CGACGCTCTTCCGATCTCTGACCATCCTCTTTGAATAC |
| EIF1AX_01_REV_TAG | AGACGTGTGCTCTTCCGATCTTTCATTTTATTTCATACTGTTTTACAGA |
| EIF1AX_02_FWD_TAG | CGACGCTCTTCCGATCTGTGAGCACTAAAGTAAATAAGC |
| EIF1AX_02_REV_TAG | AGACGTGTGCTCTTCCGATCTCAGACGAAGCTAGAAGTCT |
| EIF1AX_03_FWD_TAG | CGACGCTCTTCCGATCTAAACACAAGGTACATCTACTTAC |
| EIF1AX_03_REV_TAG | AGACGTGTGCTCTTCCGATCTTTACAGTGCTGACTTATGAGT |
| GNAS_01_FWD_TAG | CGACGCTCTTCCGATCTCCAGACCTTTGCTTTAGATT |
| GNAS_01_REV_TAG | AGACGTGTGCTCTTCCGATCTGCTTACTGGAAGTTGACTTT |
| GNAS_02_FWD_TAG | CGACGCTCTTCCGATCTCCAGTCCCTCTGGAATAA |
| GNAS_02_REV_TAG | AGACGTGTGCTCTTCCGATCTAGAAGCAAAGCGTTCTTTAC |
| HRAS_01_FWD_TAG | CGACGCTCTTCCGATCTAAAGACTTGGTGTTGTTGAT |
| HRAS_01_REV_TAG | AGACGTGTGCTCTTCCGATCTGGAAGCAGGTGGTCATT |
| HRAS_02A_FWD_TAG | CGACGCTCTTCCGATCTCTATAGTGGGGTCGTAT |
| HRAS_02A_REV_TAG | AGACGTGTGCTCTTCCGATCTAGACCCTGTAGGAGGAC |
| HRAS_03_FWD_THY_TAG | CGACGCTCTTCCGATCTTCCCTGGCTAGCTGT |
| HRAS_03_REV_THY_TAG | AGACGTGTGCTCTTCCGATCTGGACTCGGATGACGTG |
| HRAS_04_FWD_THY_TAG | CGACGCTCTTCCGATCTAGCCTGCCAGATTC |
| HRAS_04_REV_THY_TAG | AGACGTGTGCTCTTCCGATCTGTCCTGGATGCCGC |
| HRAS_05_FWD_THY_TAG | CGACGCTCTTCCGATCTTGCGCAGAGAGGACA |
| HRAS_05_REV_THY_TAG | AGACGTGTGCTCTTCCGATCTCGGGGAGGGCTTCC |
| HRAS_06_FWD_THY_TAG | CGACGCTCTTCCGATCTCCGGTGCGCATGT |
| HRAS_06_REV_THY_TAG | AGACGTGTGCTCTTCCGATCTCCACGGAAGGTCCTGA |
| HRAS_07_FWD_THY_TAG | CGACGCTCTTCCGATCTCACCATGCAGGGGAC |
| HRAS_07_REV_THY_TAG | AGACGTGTGCTCTTCCGATCTCTGACCATCCAGCTGATC |
| HRAS_08_FWD_THY_TAG | CGACGCTCTTCCGATCTCCAGCTTATATTCCGTCATC |
| HRAS_08_REV_THY_TAG | AGACGTGTGCTCTTCCGATCTGGGTTTGCCCTTCAGAT |
| KRAS_03_FWD_TAG | CGACGCTCTTCCGATCTGGATCATATTCGTCCACAAA |
| KRAS_03_REV_TAG | AGACGTGTGCTCTTCCGATCTGTGTGACATGTTCTAATATAGTCA |
| KRAS_06_FWD_THY_TAG | CGACGCTCTTCCGATCTCATAAACATTATTTAAAAATTTTTATTAAATAT-TATATGC |
| KRAS_06_REV_THY_TAG | AGACGTGTGCTCTTCCGATCTTGTATTTGCCATAAATAATACTAAATCA |
| KRAS_07_FWD_THY_TAG | CGACGCTCTTCCGATCTACCCACCTATAATGGTGAATA |

TABLE 1-continued

Primer Pairs for DNA Library

| Primer Name | Sequence (5'→3') (SEQ ID NOS 1-118, respectively, in order of appearance) |
|---|---|
| KRAS_07_REV_THY_TAG | AGACGTGTGCTCTTCCGATCTAACCTGTCTCTTGGATATTCT |
| KRAS_08_FWD_THY_TAG | CGACGCTCTTCCGATCTGGTCCTGCACCAGTAATAT |
| KRAS_08_REV_THY_TAG | AGACGTGTGCTCTTCCGATCTGCTGAAAATGACTGAATATAAACTTG |
| KRAS_10_FWD_THY_TAG | CGACGCTCTTCCGATCTCAGATCTGTATTTATTTCAGTGTTAC |
| KRAS_10_REV_THY_TAG | AGACGTGTGCTCTTCCGATCTAGTTAAGGACTCTGAAGATGTAC |
| KRAS_11_FWD_THY_TAG | CGACGCTCTTCCGATCTGGAATTCCATAACTTCTTGCTA |
| KRAS_11_REV_THY_TAG | AGACGTGTGCTCTTCCGATCTGTGTTACTAATGACTGTGCTATAA |
| NRAS_01_FWD_TAG | CGACGCTCTTCCGATCTATAATGCTCCTAGTACCTGTAG |
| NRAS_01_REV_TAG | AGACGTGTGCTCTTCCGATCTACCTGTTTGTTGGACATACT |
| NRAS_02_FWD_TAG | CGACGCTCTTCCGATCTGGTGGGATCATATTCATCTAC |
| NRAS_02_REV_TAG | AGACGTGTGCTCTTCCGATCTCGCCAATTAACCCTGATTA |
| NRAS_04_FWD_THY_TAG | CGACGCTCTTCCGATCTGTGGGCTTGTTTTGTATCA |
| NRAS_04_REV_THY_TAG | AGACGTGTGCTCTTCCGATCTGTACCCAGCCTAATCTTGT |
| NRAS_05_FWD_THY_TAG | CGACGCTCTTCCGATCTTCTTCCCTAGTGTGGTAAC |
| NRAS_05_REV_THY_TAG | AGACGTGTGCTCTTCCGATCTGAAGGCTTCCTCTGTGTATT |
| NRAS_06B_FWD_THY_TAG | CGACGCTCTTCCGATCTCGCCTGTCCTCATGTAT |
| NRAS_06B_REV_THY_TAG | AGACGTGTGCTCTTCCGATCTTCCCTGCCCCCTTAC |
| NRAS_07_FWD_THY_TAG | CGACGCTCTTCCGATCTTCAGCGGGCTACCA |
| NRAS_07_REV_THY_TAG | AGACGTGTGCTCTTCCGATCTTGCTGGTGTGAAATGACT |
| PIK3CA_08A_FWD_TAG | CGACGCTCTTCCGATCTTATTATTTTATTTTACAGAGTAACAGACTAG |
| PIK3CA_08A_REV_TAG | AGACGTGTGCTCTTCCGATCTTTTAGCACTTACCTGTGACT |
| PIK3CA_09A_FWD_TAG | CGACGCTCTTCCGATCTGATGTGTTACAAGGCTTATCTA |
| PIK3CA_09A_REV_TAG | AGACGTGTGCTCTTCCGATCTGCCTCTTGCTCAGTTTTATC |
| PIK3CA_09BFWD_TAG | CGACGCTCTTCCGATCTTGGAATGCCAGAACTACA |
| PIK3CA_09BREV_TAG | AGACGTGTGCTCTTCCGATCTGTGGAAGATCCAATCCATTTT |
| PIK3CA_10_FWD_TAG | CGACGCTCTTCCGATCTGAGGCTTTGGAGTATTTCA |
| PIK3CA_10_REV_TAG | AGACGTGTGCTCTTCCGATCTCTGCTGAGAGTTATTAACAGT |
| PIK3CA_14_FWD_TAG | CGACGCTCTTCCGATCTGTCTACGAAAGCCTCTCTA |
| PIK3CA_14_REV_TAG | AGACGTGTGCTCTTCCGATCTGGCATGCTGTCGAATAG |
| PTEN_06_FWD_TAG | CGACGCTCTTCCGATCTACAATCATGTTGCAGCA |
| PTEN_06_REV_TAG | AGACGTGTGCTCTTCCGATCTAAAAACATCAAAAAATAACTTACCTTTT |
| PTEN_08A_FWD_TAG | CGACGCTCTTCCGATCTCAATTTAGTGAAATAACTATAATGGAAC |
| PTEN_08A_REV_TAG | AGACGTGTGCTCTTCCGATCTAGTGCCACTGGTCTATAAT |
| PTEN_10B_FWD_TAG | CGACGCTCTTCCGATCTCTGCCAGCTAAAGGTGAAGATA |
| PTEN_10B_REV_TAG | AGACGTGTGCTCTTCCGATCTGCATCTTGTTCTGTTTGTGGAA |
| PTEN_13_FWD_TAG | CGACGCTCTTCCGATCTTAGAGCGTGCAGATAATGA |
| PTEN_13_REV_TAG | AGACGTGTGCTCTTCCGATCTTCAACAACCCCCACAAA |

TABLE 1-continued

Primer Pairs for DNA Library

| Primer Name | Sequence (5'→3') (SEQ ID NOS 1-118, respectively, in order of appearance) |
|---|---|
| PTEN_16_FWD_TAG | CGACGCTCTTCCGATCTGCACAATATCCTTTTGAAGAC |
| PTEN_16_REV_TAG | AGACGTGTGCTCTTCCGATCTGCACATATCATTACACCAGTTC |
| RET_01_FWD_TAG | CGACGCTCTTCCGATCTCCCGGGGATTAAAGC |
| RET_01_REV_TAG | AGACGTGTGCTCTTCCGATCTTCAGATGTGCTGTTGAGAC |
| RET_02_FWD_TAG | CGACGCTCTTCCGATCTCCATGAGGCAGAGCATA |
| RET_02_REV_TAG | AGACGTGTGCTCTTCCGATCTGCACCGAGACGATGAA |
| RET_04_FWD_TAG | CGACGCTCTTCCGATCTGGCCATGGCCTGAC |
| RET_04_REV_TAG | AGACGTGTGCTCTTCCGATCTGCACCTGGCTCCTCT |
| RET_05_FWD_TAG | CGACGCTCTTCCGATCTCCCCTCCTTCCTAGAGA |
| RET_05_REV_TAG | AGACGTGTGCTCTTCCGATCTGAGCAACACCCACACTTA |
| RET_06A_FWD_TAG | CGACGCTCTTCCGATCTTATGGTCATGGAAGGGG |
| RET_06A_REV_TAG | AGACGTGTGCTCTTCCGATCTCCCCATACAATTTGATGACA |
| RET_07_FWD_TAG | CGACGCTCTTCCGATCTGTGCGACGAGCTGT |
| RET_07_REV_TAG | AGACGTGTGCTCTTCCGATCTTCCGGAAGGTCATCTCA |
| RET_08_FWD_TAG | CGACGCTCTTCCGATCTGGATCCAAAGTGGGAATTC |
| RET_08_REV_TAG | AGACGTGTGCTCTTCCGATCTAGGTACCTTTCAGCATCTTC |
| TERT_02_FWD_TAG: | CGACGCTCTTCCGATCTGGGCCGCGGAAAGGAA |
| TERT_02_REV_TAG: | AGACGTGTGCTCTTCCGATCTTGGCGGAGGGACTGG |
| TP53_03_FWD_TAG | CGACGCTCTTCCGATCTGAAACTTTCCACTTGATAAGAG |
| TP53_03_REV_TAG | AGACGTGTGCTCTTCCGATCTCCAAGGGTGCAGTTATG |
| TP53_05_FWD_TAG | CGACGCTCTTCCGATCTTTACCTCGCTTAGTGCT |
| TP53_05_REV_TAG | AGACGTGTGCTCTTCCGATCTTGCCTCTTGCTTCTCTT |
| TP53_06_FWD_TAG | CGACGCTCTTCCGATCTTGCAGGGTGGCAA |
| TP53_06_REV_TAG | AGACGTGTGCTCTTCCGATCTGCACTGGCCTCATCTTG |
| TP53_07_FWD_TAG | CGACGCTCTTCCGATCTCCCAGAGACCCCAGT |
| TP53_07_REV_TAG | AGACGTGTGCTCTTCCGATCTCCTCACTGATTGCTCTTAGG |
| TP53_08B_FWD_TAG | CGACGCTCTTCCGATCTAGCCCTGTCGTCTCT |
| TP53_08B_REV_TAG | AGACGTGTGCTCTTCCGATCTGCAGCTGTGGGTTGAT |
| TP53_08C_FWD_TAG | CGACGCTCTTCCGATCTCGTCATGTGCTGTGAC |
| TP53_08C_REV_TAG | AGACGTGTGCTCTTCCGATCTGCCCTGACTTTCAACTCT |
| TSHR_01_FWD_TAG | CGACGCTCTTCCGATCTAAGGAACTGATAGCAAGAAAC |
| TSHR_01_REV_TAG | AGACGTGTGCTCTTCCGATCTGGTCCCTGCCACTTAC |
| TSHR_02_FWD_TAG | CGACGCTCTTCCGATCTAGTGAAGACATGGTGTGTA |
| TSHR_02_REV_TAG | AGACGTGTGCTCTTCCGATCTTGGCTGGTGAGGAGAATA |
| TSHR_03_FWD_TAG | CGACGCTCTTCCGATCTGTCTTTGTCCTGCTTATTCT |
| TSHR_03_REV_TAG | AGACGTGTGCTCTTCCGATCTGGCATGGTTGTAGTACTCA |
| TSHR_04A_FWD_TAG | CGACGCTCTTCCGATCTTGAGTACTACAACCATGCCA |
| TSHR_04A_REV_TAG | AGACGTGTGCTCTTCCGATCTGAAGGTGATGGCATACCA |

TABLE 1-continued

Primer Pairs for DNA Library

| Primer Name | Sequence (5'→3') (SEQ ID NOS 1-118, respectively, in order of appearance) |
|---|---|
| TSHR_05_FWD_TAG | CGACGCTCTTCCGATCTGTTTGCTGCTTCCTTCTC |
| TSHR_05_REV_TAG | AGACGTGTGCTCTTCCGATCTTGACGAAGGCAACTATGT |
| TSHR_06_FWD_TAG | CGACGCTCTTCCGATCTCGAAATCCGCAGTACAA |
| TSHR_06_REV_TAG | AGACGTGTGCTCTTCCGATCTTGGAGTTGCTAACAGTGAT |

FWD = forward primer; REV = reverse primer

Additionally or alternatively, the methods disclosed herein are useful in detecting a gene fusion product in one or more of RET, PPARγ, NTRK1, NTRK3, BRAF, MET, LTK, THADA, FGFR2 and ALK in a subject comprising (a) extracting RNA from a FFPE thyroid sample or a FNA thyroid sample obtained from a subject; (b) reverse-transcribing the extracted RNA into cDNA; (c) generating a cDNA library of a second plurality of amplicons using a hot start DNA polymerase with 5'-3' exonuclease activity, wherein at least one amplicon corresponds to each of RET, PPARγ, NTRK1, NTRK3, BRAF, MET, LTK, THADA, FGFR2 and ALK; (d) incorporating an adapter sequence on to the ends of the second plurality of amplicons via polymerase chain reaction; and (e) detecting at least one gene fusion product in at least one of the second plurality of amplicons using high throughput massive parallel sequencing.

Additionally or alternatively, in some embodiments of the method, the at least one gene fusion product detected is a translocation in RET, PPARγ, NTRK1, NTRK3, BRAF, MET, LTK, THADA, FGFR2 and ALK. In certain embodiments, the at least one gene fusion product detected is selected from the group consisting of CCDC6 (PTC1) Exon 1/RET Exon 12, PRKAR1A Exon 8/RET Exon 12, NCOA4 Exon 10/RET Exon 12, NCOA4 Exon 9/RET Exon 12, GOLGA5 Exon 7/RET Exon 12, TRIM24 Exon 9/RET Exon 12, TRIM33 (PTC7) Exon 16/RET Exon 12, ERC1 (ELKS) Exon 11/RET Exon 12, KTN1 Exon 30/RET Exon 12, PCM1 Exon 29/RET Exon 12, TRIM27 Exon 3/RET Exon 12, HOOK3 Exon 11/RET Exon 12, CREB3L2 Exon 2/PPARγ Exon 5, PAX8 Exon 7/PPARγ Exon 5, PAX8 Exon 8/PPARγ Exon 5, PAX8 Exon 9/PPARγ Exon 5, PAX8 Exon 10/PPARγ Exon 5, ETV6 Exon 4/NTRK3 Exon 14, BRAF Exon 8/MACF1 Exon 15, AKAP9 Exon 8/BRAF Exon 9, AGK Exon 2/BRAF Exon 8, TFG Exon 5/NTRK1 Exon 12, TPM3 Exon 10/NTRK1 Exon 12, TPR Exon 21/NTRK1 Exon 12, ETV6 Exon 5/NTRK3 Exon 14, STRN Exon 3/ALK Exon 20, EML4 Exon 13/ALK Exon 20, EML4 Exon 20/ALK Exon 20, EML4 Exon 6/ALK Exon 20, TFG Exon 5/MET Exon 15, UACA Exon 17/LTK Exon 10, AGGF1 Exon 5/RAF1 Exon 8, MACF1 Exon 60/BRAF Exon 9, THADA Exon 27/PPARG Intron 2a, THADA Exon 27/PPARG Intron 2b, THADA Exon 27/Chr 7p non-coding (FUS7p), THADA Exon 28/IGF2BP3 Exon 4, TRA2A Exon 7/THADA Exon 37, FGFR2 Exon 16/OFD1 Exon 3, VCL Exon 1/FGFR2 Exon 18, and SND1 Exon 10/BRAF Exon 9.

In some embodiments of the method, the FNA thyroid sample has been diagnosed as AUS/FLUS, FN/SFN or SUSP. In some embodiments of the method, the hot start DNA polymerase with 5'-3' exonuclease activity is AmpliTaq Gold®.

Additionally or alternatively, in some embodiments of the method, the second plurality of amplicons is generated using at least two, at least three, at least four, at least five, at least six, at least eight, at least ten, or at least twelve or more primers disclosed in Table 2.

TABLE 2

Primer Pairs for RNA Library

| Primer Name | Sequence (5'→3') (SEQ ID NOS 119-193, respectively, in order of appearance) |
|---|---|
| Fwd_ABL1_Exon2_F_ABL1_Exon3_R_TAG | CGACGCTCTTCCGATCTTGGAGATAACACTCTAAGCATAACTAAAGGT |
| Fwd_AGGF1_Exon5_F-RAF1_Exon8_R_TAG | CGACGCTCTTCCGATCTGCAACCTTATCCGACTTCTA |
| Fwd_AGK_Exon2_F-BRAF_Exon8_R_TAG | CGACGCTCTTCCGATCTGAGGCCATTGGCTCTAT |
| Fwd_AKAP9_Exon8_F-BRAF_Exon9_R_TAG | CGACGCTCTTCCGATCTCAGTTGATTTTGGATCACTTAC |
| Fwd_BRAF_Exon8_F-MACF1_Exon15_R_TAG | CGACGCTCTTCCGATCTGCTCCCAATGTGCATATAA |
| Fwd_CREB3L2_Exon2_F-PPARG_Exon5_R_TAG | CGACGCTCTTCCGATCTGCCCTTCACCCACATTA |
| Fwd_EML4_Exon13_F-ALK_Exon20_R_TAG | CGACGCTCTTCCGATCTCTGGGAAAGGACCTAAAG |
| Fwd_EML4_Exon20_F-ALK_Exon20_R_TAG | CGACGCTCTTCCGATCTCGGGAGACTATGAAATATTGT |
| Fwd_ERC1_Exon11_F-RET_Exon12_R_TAG | CGACGCTCTTCCGATCTAAGGACTCACGGCTTAAG |
| Fwd_ETV6_Exon5_F-NTRK3_Exon14_R_TAG_B | CGACGCTCTTCCGATCTCATGGTCTCTGTCTCCC |

TABLE 2-continued

Primer Pairs for RNA Library

| Primer Name | Sequence (5'→3') (SEQ ID NOS 119-193, respectively, in order of appearance) |
|---|---|
| Fwd_FGFR2_OFD1_1 | CGACGCTCTTCCGATCTTCGAATTCTCACTCTCACAACC |
| Fwd_GAPDHL_Exon1_F_GAPDH_Exon3_R_TAG | CGACGCTCTTCCGATCTAGTCAGCCGCATCTTCTTT |
| Fwd_GOLGA5_Exon7_F-RET_Exon12_R_TAG | CGACGCTCTTCCGATCTCATGGAGCTGGAAGAACT |
| Fwd_HOOK3_Exon11_F-RET_Exon12_R_TAG | CGACGCTCTTCCGATCTTATGCAGAATACTGTCAGTCTA |
| Fwd_KRT20L_Exon1_F_KRT20_Exon2_R_TAG | CGACGCTCTTCCGATCTGAAGAGCTGCGAAGTCAGATTA |
| Fwd_KRT7_Exon4_F-KRT7_Exon5_R_TAG | CGACGCTCTTCCGATCTTGGATGCTGCCTACAT |
| Fwd_KTN1_Exon30_F-RET_Exon12_R_TAG | CGACGCTCTTCCGATCTGAAAAGGAAAATGAATTGAAGAGG |
| Fwd_MACF1_Exon60_F-BRAF_Exon9_R_TAG | CGACGCTCTTCCGATCTAGAAGGGCTGGATAAACT |
| Fwd_NCOA4_Exon10_F-RET_Exon12_R_TAG | CGACGCTCTTCCGATCTCCCCAGGACTGGCTTACCC |
| Fwd_NCOA4_Exon9_F-RET_Exon12_R_TAG | CGACGCTCTTCCGATCTCAAATTCCTGAGCACTTGA |
| Fwd_PAX8_Exon10_F-PPARG_Exon5_R_TAG | CGACGCTCTTCCGATCTCAGCTATGCCTCCTCT |
| Fwd_PAX8_Exon7_F-PPARG_Exon5_R_TAG | CGACGCTCTTCCGATCTAGCGGCAGCACTAC |
| Fwd_PAX8_Exon8_F-PPARG_Exon5_R_TAG | CGACGCTCTTCCGATCTGCAACCTCTCGACTCA |
| Fwd_PAX8_Exon9_F-PPARG_Exon5_R_TAG | CGACGCTCTTCCGATCTGTGTACGGGCAGTTCA |
| Fwd_PCM1_Exon29_F-RET_Exon12_R_TAG | CGACGCTCTTCCGATCTTAGTTCACAACAACCTGTAAG |
| Fwd_PRKAR1A_Exon8_F-RET_Exon12_R_TAG | CGACGCTCTTCCGATCTTTTGGAGAACTTGCTTTGAT |
| Fwd_PTH_1 | CGACGCTCTTCCGATCTACTCAGCATCAGCTACTAACA |
| Fwd_RET/PTC1_TAG | CGACGCTCTTCCGATCTCGCGACCTGCGCAAA |
| Fwd_SND1_Exon10_F-BRAF_Exon9_R_TAG | CGACGCTCTTCCGATCTATTGTTGTGAAGCTGAACT |
| Fwd_STRN_Exon3_F-ALK_Exon20_R_TAG | CGACGCTCTTCCGATCTCCTCCAAGCTATGATTCTG |
| Fwd_TFG_Exon5_F-MET_Exon15_R_TAG | CGACGCTCTTCCGATCTAGCGTTTGGCTTAACAG |
| Fwd_TFG_Exon5_F-NTRK1_Exon12_R_TAG | CGACGCTCTTCCGATCTTTATGGCAGCAAGTATGTC |
| Fwd_TFRC_1 | CGACGCTCTTCCGATCTATACCTTTCGTCCCTGCATTTA |
| Fwd_TG_Exon5_F-TG_Exon6_R_TAG | CGACGCTCTTCCGATCTACACCACAGACATGATGAT |
| Fwd_THADA_IGF2BP3_1 | CGACGCTCTTCCGATCTCGAACTCTGTTGTCCACACT |
| Fwd_THADA_PPARG_iso1 + 7p_1 | CGACGCTCTTCCGATCTCCGATGGATGGTACTTCTTCTG |
| Fwd_THADA_PPARG_iso2_1 | CGACGCTCTTCCGATCTCCGATGGATGGTACTTCTTCTG |
| Fwd_TPM3_Exon10_F-NTRK1_Exon12_R_TAG | CGACGCTCTTCCGATCTGGAAGAAATCAAGATTCTTACTG |
| Fwd_TPR_Exon21_F-NTRK1_Exon12_R_TAG | CGACGCTCTTCCGATCTCAGAGACAAATCTTCATCTTAAC |
| Fwd_TRA2A_THADA_1 | CGACGCTCTTCCGATCTGAAGACGATCACCTTCTCCTTATT |
| Fwd_TRIM24_Exon9_F-RET_Exon12_R_TAG | CGACGCTCTTCCGATCTCCACCAAGTGGTTTATCAT |
| Fwd_TRIM27_Exon3_F-RET_Exon12_R_TAG | CGACGCTCTTCCGATCTCAGTTCTCTTGCAACATCT |
| Fwd_TRIM33_Exon16_F-RET_Exon12_R_TAG | CGACGCTCTTCCGATCTGGAAAGCCAGAAGTTGAATA |
| Fwd_UACA_Exon17_F-LTK_Exon10_R_TAG | CGACGCTCTTCCGATCTCAGCACCAAGTGAAATCTC |
| Fwd_VCL_FGFR2_1 | CGACGCTCTTCCGATCTGATCTCCCACCTGGTGATAATG |
| Fwd_EML4_Exon6_F-ALK_Exon20_R_TAG | CGACGCTCTTCCGATCTAAAACTGCAGACAAGCA |
| Fwd_ETV6_Exon4_F-NTRK3_Exon14_R_TAG | CGACGCTCTTCCGATCTCAGCCGGAGGTCATA |

TABLE 2-continued

Primer Pairs for RNA Library

| Primer Name | Sequence (5'→3') (SEQ ID NOS 119-193, respectively, in order of appearance) |
|---|---|
| Rev_ABL1_Exon2_F_ABL1_Exon3_R_TAG | AGACGTGTGCTCTTCCGATCTGATGTAGTTGCTTGGGACCCA |
| Rev_AGGF1_Exon5_F-RAF1_Exon8_R_TAG | AGACGTGTGCTCTTCCGATCTGCTGATTCGCTGTGACT |
| Rev_AGK_Exon2_F-BRAF_Exon8_R_TAG | AGACGTGTGCTCTTCCGATCTTCGTTGCCCAAATTGATTTC |
| Rev_AKAP9_Exon8_F-BRAF_Exon9_R_TAG | AGACGTGTGCTCTTCCGATCTACGAAATCCTTGGTCTCTA |
| Rev_BRAF_Exon8_F-MACF1_Exon15_R_TAG | AGACGTGTGCTCTTCCGATCTAGCCCAGCTCTTCTACA |
| Rev_CREB3L2_Exon2_F-PPARG_Exon5_R_TAG | AGACGTGTGCTCTTCCGATCTGGGAGTGGTCTTCCATTAC |
| Rev_ETV6_Exon4_F-NTRK3_Exon14_R_TAG | AGACGTGTGCTCTTCCGATCTTGATGCCGTGGTTGAT |
| Rev_ETV6_Exon5_F-NTRK3_Exon14_R_TAG | AGACGTGTGCTCTTCCGATCTTGATGCCGTGGTTGAT |
| Rev_FGFR2_OFD1_1 | AGACGTGTGCTCTTCCGATCTGGAGCTCCCTTCTACTGAAATG |
| Rev_GAPDHL_Exon1_F_GAPDH_Exon3_R_TAG | AGACGTGTGCTCTTCCGATCTCAATACGACCAAATCCGTTGAC |
| Rev_KRT20L_Exon1_F_KRT20_Exon2_R_TAG | AGACGTGTGCTCTTCCGATCTGTCCTCAGCAGCCAGTTTAG |
| Rev_KRT7_Exon4_F-KRT7_Exon5_R_TAG | AGACGTGTGCTCTTCCGATCTGCAGCTCTGTCAACT |
| Rev_NCOA4_Exon10_F-RET_Exon12_R_TAG | CGACGCTCTTCCGATCTTGGAGATAACACTCTAAGCATAACTAAAGGT |
| Rev_NCOA4_Exon9_F-RET_Exon12_R_TAG | AGACGTGTGCTCTTCCGATCTGAGGGAATTCCCACTTT |
| Rev_PTH_1 | AGACGTGTGCTCTTCCGATCTTGCCAACATGACAATCATAACT |
| Rev_RET/PTC1_TAG | AGACGTGTGCTCTTCCGATCTCAAGTTCTTCCGAGGGAATTCC |
| Rev_STRN_Exon3_F-ALK_Exon20_R_TAG | AGACGTGTGCTCTTCCGATCTCAGTAGTTGGGGTTGTAGT |
| Rev_TFG_Exon5_F-NTRK1_Exon12_R_TAG | AGACGTGTGCTCTTCCGATCTCCAGATGTGCTGTTAGTGT |
| Rev_TFRC_1 | AGACGTGTGCTCTTCCGATCTCTGGCAGAAACCTTGAAGTTG |
| Rev_TG_Exon5_F-TG_Exon6_R_TAG | AGACGTGTGCTCTTCCGATCTAGTGGCAATACCCAGATAC |
| Rev_THADA_7p_1 | AGACGTGTGCTCTTCCGATCTCCCATTGGCCTGAGTTTCT |
| Rev_THADA_IGF2BP3_1 | AGACGTGTGCTCTTCCGATCTCAGCACCTCCCACTGTAAAT |
| Rev_THADA_PPARG_iso1_1 | AGACGTGTGCTCTTCCGATCTAGCCAGGTCACTGAGTTACTA |
| Rev_THADA_PPARG_iso2_1 | AGACGTGTGCTCTTCCGATCTTCTCTTGAACCCAGGAGGT |
| Rev_TRA2A_THADA_1 | AGACGTGTGCTCTTCCGATCTGCTGGAGCAGATCACACAG |
| Rev_UACA_Exon17_F-LTK_Exon10_R_TAG | AGACGTGTGCTCTTCCGATCTGGGTCTGAGCAGAGTAAC |
| Rev_VCL_FGFR2_1 | AGACGTGTGCTCTTCCGATCTGTTGGCTGAGGTCCAAGTAT |
| Rev_TFG_Exon5_F-MET_Exon15_R_TAG | AGACGTGTGCTCTTCCGATCTTCAGAGTCCCCACTAGTTA | where
Fwd = forward primer; Rev = reverse primer;
"THADA_PPARG_iso1_1" refers to THADA_Exon27_F-PPARG_Intron 2a_R_TAG;
"THADA_PPARG_iso2_1" refers to THADA_Exon27_F-PPARG_Intron 2b_R_TAG;
"THADA_7p_1" refers to THADA_Exon27_F-Chr7p_non-coding_R_TAG;
"THADA_IGF2BP3_1" refers to THADA_Exon28_F-IGF2BP3_Exon4__R_TAG;
"TRA2A_THADA_1" refers to TRA2A_Exon7_F-THADA_Exon37_R_TAG;
"FGFR2_OFD1_1" refers to FGFR2_Exon16_F-OFD1_Exon3_R_TAG; and
"VCL_FGFR2_1" refers to VCL_Exon1_F-FGFR2_Exon18_R_TAG In any of the above embodiments, a single primer or one or both primers of a primer pair comprise a sequence tag ligated to the 5' end of the target specific sequence portion of the primer. This sequence tag is a short oligonucleotide of known sequence that can provide a priming site for a subsequent PCR reaction. In certain embodiments, amplicons corresponding to specific regions of BRAF, NRAS, HRAS, KRAS, PIK3CA, TP53, CTNNB1, PTEN, TSHR, AKT1, GNAS, RET, TERT, and EIF1AX are amplified using primers that contain sequence tags to produce sequence tagged amplicons. In other embodiments, amplicons corresponding to specific regions of RET, PPARγ, NTRK1, NTRK3, BRAF, MET, LTK, THADA, FGFR2 and ALK are amplified using primers that contain sequence tags to produce sequence tagged amplicons.

In any of the above embodiments, the sequences tags are used as a mechanism to incorporate a specific adapter sequence (also referred to as a sequencing adapter) on to one or both ends of the amplicons via a subsequent PCR reaction.

In any of the above embodiments, the employed primers do not contain adapter sequences (but contain sequence tags) and an oligonucleotide sequencing adapter is subsequently incorporated on to one or both ends of the resulting sequence tagged amplicons in a subsequent PCR reaction. As shown in FIG. 1, the first PCR reaction utilizes primer pairs containing target-specific sequences and sequence tags, which are used as primer sites for a second PCR reaction. The second PCR reaction incorporates barcode sequences and library adaptors that enable the amplicons to bind to a flow cell.

Sequencing adapters are short oligonucleotides of known sequence that can provide a priming site for both amplification and sequencing of the adjoining, unknown target nucleic acid. As such, adapters allow binding of a fragment to a flow cell for next generation sequencing. Any adapter sequence may be incorporated on to one or both ends of the sequence tagged amplicons in a subsequent PCR reaction.

In some embodiments, all forward amplicons generated during the subsequent PCR reaction contain the same adapter sequence. In some embodiments when double stranded sequencing is performed, all forward amplicons generated during the subsequent PCR reaction contain the same adapter sequence and all reverse amplicons generated during the subsequent PCR reaction contain an adapter sequence that is different from the adapter sequence of the forward amplicons. In some embodiments, the adapter sequences further comprise an index sequence (also referred to as an index tag, a "barcode" or a multiplex identifier (MID)).

In any of the above embodiments, the adapter sequences are P5 and/or P7 adapter sequences that are recommended for Illumina sequencers (MiSeq and HiSeq). See, e.g., Williams-Carrier et al., *Plant J.*, 63(1):167-77 (2010). In some embodiments, the adapter sequences are P1, A, or Ion Xpress™ barcode adapter sequences that are recommended for Life Technologies sequencers. Other adapter sequences are known in the art. Some manufacturers recommend specific adapter sequences for use with the particular sequencing technology and machinery that they offer.

Additionally or alternatively, in any of the above embodiments, amplicons corresponding to specific regions of BRAF, NRAS, HRAS, KRAS, PIK3CA, TP53, CTNNB1, PTEN, TSHR, AKT1, GNAS, RET, TERT, and EIF1AX from more than one sample are sequenced. In any of the above embodiments, amplicons corresponding to specific regions of RET, PPARγ, NTRK1, NTRK3, BRAF, MET, LTK, THADA, FGFR2 and ALK from more than one sample are sequenced. In some embodiments, all samples are sequenced simultaneously in parallel.

In any of the above embodiments, amplicons corresponding to specific regions of BRAF, NRAS, HRAS, KRAS, PIK3CA, TP53, CTNNB1, PTEN, TSHR, AKT1, GNAS, RET, TERT, and EIF1AX from at least 1, 5, 8, 10, 16, 20, 24, 30, 32, 35, 40, 45, 48, 50, 56, 64, 72, 80, 88, 96, 104, 112, 120, 128, 136, 144, 152, 160, 168, 176, 184, 192, 200, 208, 216, 224, 232, 240, 248, 256, 264, 272, 280, 288, 296, 304, 312, 320, 328, 336, 344, 352, 360, 368, 376, or up to 384 different samples are amplified and sequenced using the methods described herein. In any of the above embodiments, amplicons corresponding to specific regions of RET, PPARγ, NTRK1, NTRK3, BRAF, MET, LTK, THADA, FGFR2 and ALK from at least 1, 5, 8, 10, 16, 20, 24, 30, 32, 35, 40, 45, 48, 50, 56, 64, 72, 80, 88, 96, 104, 112, 120, 128, 136, 144, 152, 160, 168, 176, 184, 192, 200, 208, 216, 224, 232, 240, 248, 256, 264, 272, 280, 288, 296, 304, 312, 320, 328, 336, 344, 352, 360, 368, 376, or up to 384 different samples are amplified and sequenced using the methods disclosed herein.

Additionally or alternatively, in any of the above embodiments, adapter tagged amplicons derived from a single sample may further comprise an identical index sequence that indicates the source from which the amplicon is generated, the index sequence for each sample being different from the index sequences from all other samples. As such, the use of index sequences permits multiple samples to be pooled per sequencing run and the sample source subsequently ascertained based on the index sequence. In some embodiments, the Access Array™ System (Fluidigm Corp., San Francisco, Calif.) or the Apollo 324 System (Wafergen Biosystems, Fremont, Calif.) is used to generate a barcoded (indexed) amplicon library by simultaneously amplifying the nucleic acids from the samples in one set up.

In any of the above embodiments, indexed amplicons are generated using primers (for example, forward primers and/or reverse primers) containing the index sequence. Such indexed primers may be included during library preparation as a "barcoding" tool to identify specific amplicons as originating from a particular sample source. When adapter-ligated and/or indexed primers are employed, the adapter sequence and/or index sequence gets incorporated into the amplicon (along with the sequence tag and the target-specific primer sequence) during amplification. Therefore, the resulting amplicons are sequencing-competent and do not require the traditional library preparation protocol. Moreover, the presence of the index tag permits the differentiation of sequences from multiple sample sources.

In any of the above embodiments, the amplicons may be amplified with non-adapter-ligated and/or non-indexed primers and a sequencing adapter and/or an index sequence may be subsequently incorporated on to one or both ends of each of the resulting amplicons in a subsequent PCR reaction. In some embodiments, the amplicon library is generated using a multiplexed PCR approach.

Indexed amplicons from more than one sample source are quantified individually and then pooled prior to high throughput sequencing. As such, the use of index sequences permits multiple samples (i.e., samples from more than one sample source) to be pooled per sequencing run and the sample source subsequently ascertained based on the index sequence. "Multiplexing" is the pooling of multiple adapter-tagged and indexed libraries into a single sequencing run. When indexed primer sets are used, this capability can be exploited for comparative studies. In some embodiments, amplicon libraries from up to 48 separate sources are pooled prior to sequencing.

Following the production of an adapter tagged and, optionally indexed, amplicon library, the amplicons are sequenced using high throughput, massively parallel sequencing (i.e., next generation sequencing). In some embodiments of the method, the high throughput massive parallel sequencing is performed using 454™ GS FLX™ pyrosequencing, reversible dye-terminator sequencing, SOLiD sequencing, Ion semiconductor sequencing, Helioscope single molecule sequencing, sequencing by synthesis, sequencing by ligation, or SMRT™ sequencing. In some embodiments, high throughput massively parallel sequencing may be performed using a read depth approach.

Diagnostic and Prognostic Methods of the Present Technology

In another aspect, the present disclosure provides a method for selecting a subject having thyroid nodules with indeterminate cytology for diagnostic surgery comprising: (a) extracting DNA from a FNA thyroid sample obtained from the subject; (b) generating a DNA library of a first plurality of amplicons using a hot start DNA polymerase that substantially lacks 5'-3' exonuclease activity, wherein at least one amplicon corresponds to each of the plurality of thyroid cancer-related genes, said plurality of thyroid cancer-related genes comprising BRAF, NRAS, HRAS, KRAS, PIK3CA, TP53, CTNNB1, PTEN, TSHR, AKT1, GNAS, RET, TERT, and EIF1AX; (c) incorporating an adapter sequence on to the ends of the first plurality of amplicons via polymerase chain reaction; and (d) selecting the subject for diagnostic surgery, if a mutation in at least one of the first plurality of amplicons corresponding to BRAF, NRAS, HRAS, KRAS, PIK3CA, TP53, CTNNB1, PTEN, TSHR, AKT1, RET, TERT, and EIF1AX is detected.

Additionally or alternatively, in some embodiments, the method for selecting a subject having thyroid nodules with indeterminate cytology for diagnostic surgery comprises detecting a gene fusion product in one or more of RET, PPARγ, NTRK1, NTRK3, BRAF, MET, LTK, THADA, FGFR2 and ALK in the subject comprising (a) extracting RNA from a FNA thyroid sample obtained from the subject; (b) reverse-transcribing the extracted RNA into cDNA; (c) generating a cDNA library of a second plurality of amplicons using a hot start DNA polymerase with 5'-3' exonuclease activity, wherein at least one amplicon corresponds to each of RET, PPARγ, NTRK1, NTRK3, BRAF, MET, LTK, THADA, FGFR2 and ALK; (d) incorporating an adapter sequence on to the ends of the second plurality of amplicons via polymerase chain reaction; and (e) selecting the subject for diagnostic surgery, if a gene fusion product in at least one of the second plurality of amplicons corresponding to RET, PPARγ, NTRK1, NTRK3, BRAF, MET, LTK, THADA, FGFR2 and ALK is detected.

In another aspect, the present disclosure provides a method for predicting the risk of malignancy in a subject with inconclusive thyroid FNA cytology results comprising: (a) extracting DNA from a FNA thyroid sample obtained from the subject; (b) generating a DNA library of a first plurality of amplicons using a hot start DNA polymerase that substantially lacks 5'-3' exonuclease activity, wherein at least one amplicon corresponds to each of the plurality of thyroid cancer-related genes, said plurality of thyroid cancer-related genes comprising BRAF, NRAS, HRAS, KRAS, PIK3CA, TP53, CTNNB1, PTEN, TSHR, AKT1, GNAS, RET, TERT, and EIF1AX; (c) incorporating an adapter sequence on to the ends of the first plurality of amplicons via polymerase chain reaction; and (d) identifying the subject as having a high risk of malignancy when a mutation in at least one of the first plurality of amplicons corresponding to BRAF, NRAS, HRAS, KRAS, PIK3CA, TP53, CTNNB1, PTEN, TSHR, AKT1, RET, TERT, and EIF1AX is detected.

Additionally or alternatively, in some embodiments, the method for predicting the risk of malignancy in a subject with inconclusive thyroid FNA cytology results comprises detecting a gene fusion product in one or more of RET, PPARγ, NTRK1, NTRK3, BRAF, MET, LTK, THADA, FGFR2 and ALK in the subject comprising (a) extracting RNA from a FNA thyroid sample obtained from the subject; (b) reverse-transcribing the extracted RNA into cDNA; (c) generating a cDNA library of a second plurality of amplicons using a hot start DNA polymerase with 5'-3' exonuclease activity, wherein at least one amplicon corresponds to each of RET, PPARγ, NTRK1, NTRK3, BRAF, MET, LTK, THADA, FGFR2 and ALK; (d) incorporating an adapter sequence on to the ends of the second plurality of amplicons via polymerase chain reaction; and (e) identifying the subject as having a high risk of malignancy when a gene fusion product in at least one of the second plurality of amplicons corresponding to RET, PPARγ, NTRK1, NTRK3, BRAF, MET, LTK, THADA, FGFR2 and ALK is detected.

In any of the above embodiments, the mutation detected is selected from the group consisting of AKT1 E17K, BRAF V600E, BRAF K601E, KRAS G13D, KRAS G12V, KRAS Q61R, KRAS G12D, NRAS Q61R, NRAS Q61K, PIK3CA E545K, PIK3CA H1047R, PIK3CA G914R, HRAS Q61R, RET M918T, TSHR R274W, TSHR A581S, TERT-124 C>T and TERT-146 C>T. In any of the above embodiments, the gene fusion product detected is selected from the group consisting of CCDC6 (PTC1) Exon 1/RET Exon 12, PRKAR1A Exon 8/RET Exon 12, NCOA4 Exon 10/RET Exon 12, NCOA4 Exon 9/RET Exon 12, GOLGA5 Exon 7/RET Exon 12, TRIM24 Exon 9/RET Exon 12, TRIM33 (PTC7) Exon 16/RET Exon 12, ERC1 (ELKS) Exon 11/RET Exon 12, KTN1 Exon 30/RET Exon 12, PCM1 Exon 29/RET Exon 12, TRIM27 Exon 3/RET Exon 12, HOOK3 Exon 11/RET Exon 12, CREB3L2 Exon 2/PPARγ Exon 5, PAX8 Exon 7/PPARγ Exon 5, PAX8 Exon 8/PPARγ Exon 5, PAX8 Exon 9/PPARγ Exon 5, PAX8 Exon 10/PPARγ Exon 5, ETV6 Exon 4/NTRK3 Exon 14, BRAF Exon 8/MACF1 Exon 15, AKAP9 Exon 8/BRAF Exon 9, AGK Exon 2/BRAF Exon 8, TFG Exon 5/NTRK1 Exon 12, TPM3 Exon 10/NTRK1 Exon 12, TPR Exon 21/NTRK1 Exon 12, ETV6 Exon 5/NTRK3 Exon 14, STRN Exon 3/ALK Exon 20, EML4 Exon 13/ALK Exon 20, EML4 Exon 20/ALK Exon 20, EML4 Exon 6/ALK Exon 20, TFG Exon 5/MET Exon 15, UACA Exon 17/LTK Exon 10, AGGF1 Exon 5/RAF1 Exon 8, MACF1 Exon 60/BRAF Exon 9, THADA Exon 27/PPARG Intron 2a, THADA Exon 27/PPARG Intron 2b, THADA Exon 27/Chr 7p non-coding (FUS7p), THADA Exon 28/IGF2BP3 Exon 4, TRA2A Exon 7/THADA Exon 37, FGFR2 Exon 16/OFD1 Exon 3, VCL Exon 1/FGFR2 Exon 18, and SND1 Exon 10/BRAF Exon 9.

Kits

The present disclosure also provides kits for detecting alterations in target nucleic acid sequences corresponding to the preselected set of thyroid cancer-related genes described herein.

Kits of the present technology comprise one or more primer pairs that selectively hybridize and are useful in amplifying one or more genes selected from the group consisting of BRAF, NRAS, HRAS, KRAS, PIK3CA, TP53, CTNNB1, PTEN, TSHR, AKT1, GNAS, RET, TERI, and EIF1AX. Additionally or alternatively, the kits of the present technology comprise one or more primer pairs that are useful in amplifying and detecting translocations in one or more genes selected from the group consisting of RET, PPARγ, NTRK1, NTRK3, BRAF, MET, LTK, THADA, FGFR2 and ALK.

In some embodiments, the kits of the present technology comprise a single primer pair that hybridizes to a region or exon of a single gene selected from the group consisting of BRAF, NRAS, HRAS, KRAS, PIK3CA, TP53, CTNNB1, PTEN, TSHR, AKT1, GNAS, RET, TERT, and EIF1AX, in other embodiments, the kits of the present technology comprise multiple primer pairs that hybridize to one or more regions or exons of a single gene selected from the group consisting of BRAF, NRAS, HRAS, KRAS, PIK3CA, TP53, CTNNB1, PTEN, TSHR, AKT1, GNAS, RET, TERT, and EIF1AX, In certain embodiments, the kits of the present technology comprise multiple primer pairs comprising a single primer pair that specifically hybridizes to a region or exon of a single gene for each of BRAF, NRAS, HRAS, KRAS, PIK3CA, TP53, CTNNB1, PTEN TSHR, AKT1, GNAS, RET, TERT, and EIF1AX In certain embodiments, the kits of the present technology comprise multiple primer pairs comprising more than one primer pair that hybridizes to one or more regions or exons for each of BRAF, NRAS, HRAS, KRAS, PIK3CA, TP53, CTNNB1, PTEN, TSHR, AKT1, GNAS, RET, TERT, and EIF1AX.

Thus, it is contemplated herein that the kits of the present technology can comprise primer pairs that recognize and specifically hybridize to one or more regions or exons of one or more genes selected from the group consisting BRAF, NRAS, HRAS, KRAS, PIK3CA, TP53, CTNNB1, PTEN, TSHR, AKT1, GNAS, RET, TERT, and EIF1AX. In some embodiments, the kits of the present technology can comprise primer pairs that recognize and specifically hybridize to one or more of exon 15 of BRAF, exon 2, 3 or 4 of NRAS, exon 2, 3 or 4 of HRAS, exon 2, 3 or 4 of KRAS, exon 10 or 21 of PIK3CA, exon 5, 6, 7, 8 or 9 of TP53, exon 3 of CTNNB1, exon 5, 6, 7, or 8 of PTEN, exon 9 or 10 of TSHR, exon 3 of AKT1, exon 8 or 9 of GNAS, exon 10, 11, 12, 13 or 15 of RET, the promoter of TERT, and exon 2, 5 or 6 of EIF1AX Alternatively, the kit can comprise primer pairs that will detect one or more mutations selected from the group consisting of AKT1 E17K, BRAF V600E, BRAF K601E, KRAS G13D, KRAS G12V, KRAS Q61R, KRAS G12D, NRAS Q61R, NRAS Q61K, PIK3CA E545K, PIK3CA H1047R, PIK3CA G914R, HRAS Q61R, RET M918T, TSHR R274W, TSHR A581S, TERT-124 C>T and TERT-146 C>T.

Additionally or alternatively, the kits of the present technology may comprise primer pairs that can detect translocations in one or more genes selected from the group consisting of RET, PPARγ, NTRK1, NTRK3, BRAF, MET, LTK, THADA, FGFR2 and ALK. Alternatively, the kit may comprise primer pairs that will detect one or more gene fusion products selected from the group consisting of CCDC6 (PTC1) Exon 1/RET Exon 12, PRKAR1A Exon 8/RET Exon 12, NCOA4 Exon 10/RET Exon 12, NCOA4 Exon 9/RET Exon 12, GOLGA5 Exon 7/RET Exon 12, TRIM24 Exon 9/RET Exon 12, TRIM33 (PTC7) Exon 16/RET Exon 12, ERC1 (ELKS) Exon 11/RET Exon 12, KTN1 Exon 30/RET Exon 12, PCM1 Exon 29/RET Exon 12, TRIM27 Exon 3/RET Exon 12, HOOK3 Exon 11/RET Exon 12, CREB3L2 Exon 2/PPARγ Exon 5, PAX8 Exon 7/PPARγ Exon 5, PAX8 Exon 8/PPARγ Exon 5, PAX8 Exon 9/PPARγ Exon 5, PAX8 Exon 10/PPARγ Exon 5, ETV6 Exon 4/NTRK3 Exon 14, BRAF Exon 8/MACF1 Exon 15, AKAP9 Exon 8/BRAF Exon 9, AGK Exon 2/BRAF Exon 8, TFG Exon 5/NTRK1 Exon 12, TPM3 Exon 10/NTRK1 Exon 12, TPR Exon 21/NTRK1 Exon 12, ETV6 Exon 5/NTRK3 Exon 14, STRN Exon 3/ALK Exon 20, EML4 Exon 13/ALK Exon 20, EML4 Exon 20/ALK Exon 20, EML4 Exon 6/ALK Exon 20, TFG Exon 5/MET Exon 15, UACA Exon 17/LTK Exon 10, AGGF1 Exon 5/RAF1 Exon 8, MACF1 Exon 60/BRAF Exon 9, THADA Exon 27/PPARG Intron 2a, THADA Exon 27/PPARG Intron 2b, THADA Exon 27/Chr 7p non-coding (FUS7p), THADA Exon 28/IGF2BP3 Exon 4, TRA2A Exon 7/THADA Exon 37, FGFR2 Exon 16/OFD1 Exon 3, VCL Exon 1/FGFR2 Exon 18, and SND1 Exon 10/BRAF Exon 9.

In some embodiments, the kits comprise one or more primer pairs disclosed in Table 1. In certain embodiments, the kits comprise one or more primer pairs disclosed in Table 2. In some embodiments, the kits comprise two or more primer pairs disclosed in Table 1 and/or Table 2.

In some embodiments, the kits further comprise buffers, enzymes having polymerase activity, enzymes having polymerase activity and lacking 5'→3' exonuclease activity or both 5'→3' and 3'→5' exonuclease activity, enzyme cofactors such as magnesium or manganese, salts, chain extension nucleotides such as deoxynucleoside triphosphates (dNTPs), modified dNTPs, nuclease-resistant dNTPs or labeled dNTPs, necessary to carry out an assay or reaction, such as amplification and/or detection of alterations in target nucleic acid sequences corresponding to the specific set of thyroid cancer-related genes disclosed herein.

In one embodiment, the kits of the present technology further comprise a positive control nucleic acid sequence and a negative control nucleic acid sequence to ensure the integrity of the assay during experimental runs, A kit may further contain a means for comparing the levels and/or activity of one or more of the preselected set of thyroid cancer-related genes described herein in a tumor sample with a reference nucleic acid sample (e.g., a non-tumor sample). The kit may also comprise instructions for use, software for automated analysis, containers, packages such as packaging intended for commercial sale and the like.

The kits of the present technology can also include other necessary reagents to perform any of the NGS techniques disclosed herein. For example, the kit may further comprise one or more of: adapter sequences, barcode sequences, reaction tubes, ligases, ligase buffers, wash buffers and/or reagents, hybridization buffers and/or reagents, labeling buffers and/or reagents, and detection means. The buffers and/or reagents are usually optimized for the particular amplification/detection technique for which the kit is intended. Protocols for using these buffers and reagents for performing different steps of the procedure may also be included in the kit.

The kits of the present technology may include components that are used to prepare nucleic acids from a solid tumor test sample for the subsequent amplification and/or detection of alterations in target nucleic acid sequences corresponding to the specific set of thyroid cancer-related genes disclosed herein. Such sample preparation components can be used to produce nucleic acid extracts from tissue samples. The test samples used in the above-described methods will vary based on factors such as the assay format, nature of the detection method, and the specific tissues, cells or extracts used as the test sample to be assayed. Methods of extracting nucleic acids from samples are well known in the art and can be readily adapted to obtain a sample that is compatible with the system utilized. Automated sample preparation systems for extracting nucleic acids from a test sample are commercially available, e.g., Roche Molecular Systems' COBAS AmpliPrep System, Qiagen's BioRobot 9600, and Applied Biosystems' PRISM™ 6700 sample preparation system.

EXAMPLES

Example 1: Design of the Thyroid Cancer Screening NGS Assay of the Present Technology Experimentation efforts were directed towards designing a highly sensitive PCR-based NGS assay that could provide a more accurate diagnosis of cancer in thyroid nodules with indeterminate cytology, while using extremely small amounts of DNA derived from FFPE samples or FNA samples (~1 ng).

The methods of the present technology detect somatic mutations in 14 target genes and 41 gene fusion products (translocations) in 10 target genes. See Table 3.

TABLE 3

Thyroid Cancer Screening Panel

Somatic Gene Mutations

| | |
|---|---|
| BRAF | PTEN |
| NRAS | TSHR |
| HRAS | AKT1 |
| KRAS | GNAS |
| PIK3CA | RET |
| TP53 | TERT |
| CTNNB1 | EIF1AX |

The thyroid cancer screening panel was designed to assay for mutations in target nucleic acid sequences corresponding to specific regions of the 14 genes listed in Table 3 (instead of every exon of the entire gene) and specific gene translocations in one or more of RET, PPARγ, NTRK1, NTRK3, BRAF, MET, LTK, THADA, FGFR2 and ALK. The selection of these particular target nucleic acid sequences (or amplicons) was based in part on data from TCGA and COSMIC databases, reported mutation frequency, known hot spots etc.

Figure 14:
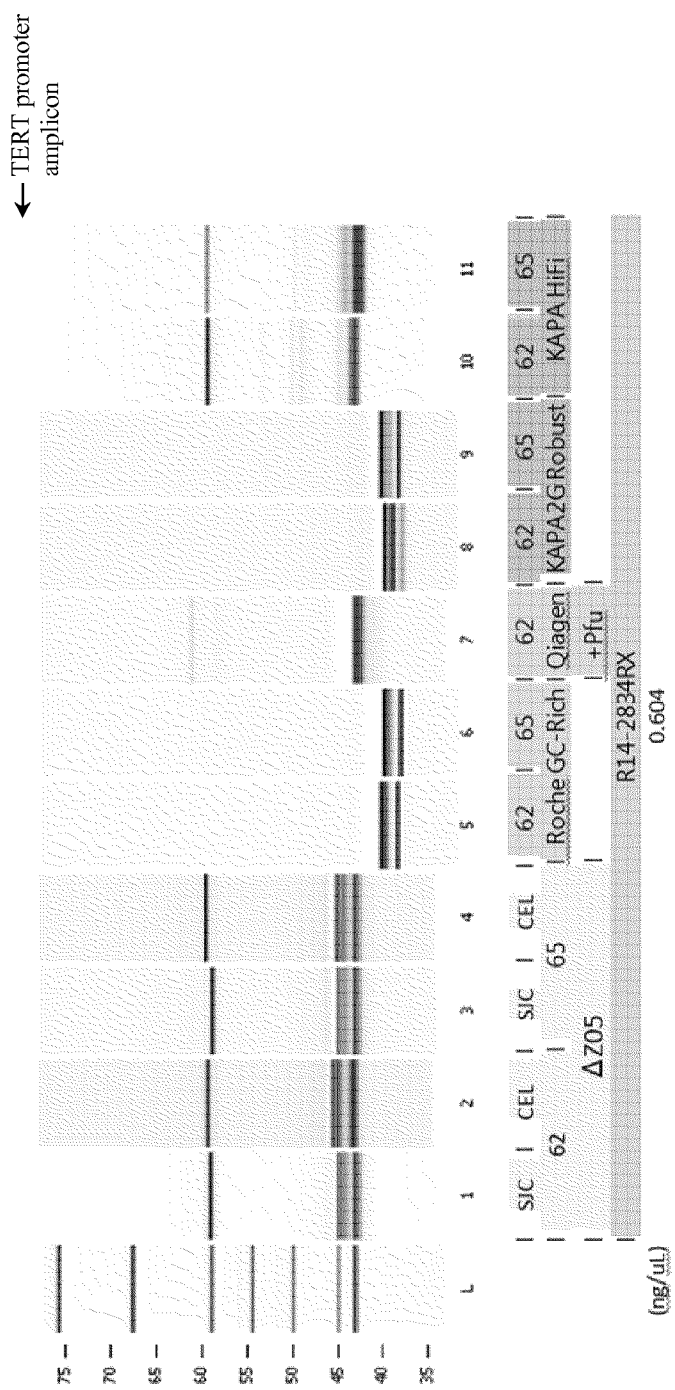
FIG. 14 shows the comparative performance of different DNA polymerases with respect to amplification of the GC rich TERT promoter.

Experiments focused on the development of an NGS screening assay that was wholly based on PCR (i.e., amplicon-based library preparation followed by NGS) in order to detect genetic alterations in amplicons corresponding to specific regions of BRAF, NRAS, HRAS, KRAS, PIK3CA, TP53, CTNNB1, PTEN, TSHR, AKT1, GNAS, RET, TERT, and EIF1AX, and translocations in one or more of RET, PPARγ, NTRK1, NTRK3, BRAF, MET, LTK, THADA, FGFR2 and ALK. One of the technical challenges that arose while developing the multiplex PCR method described herein was the optimal selection and concentration of over twenty primer pairs that simultaneously hybridize and amplify target nucleic acid sequences corresponding to specific regions of the thyroid cancer-related genes disclosed herein in a single reaction. Achieving the proper balance of primer pairs was a significant concern because differences in annealing efficiency of different primer pairs result in a strong bias in the amplification of the different amplicons, leading to insufficient coverage of some amplicons in a sample and strongly reducing the sensitivity of the assay. In order to maximize the sequencing capacity, the amplification levels should be similar among all amplicons. Furthermore the presence of a large number of different primers results in a strongly increased risk of primer dimer formation diminishing the possibility of reproducible amplifying small amounts of target nucleic acids. The optimal length of the different amplicons corresponding to specific regions of BRAF, NRAS, HRAS, KRAS, PIK3CA, TP53, CTNNB1, PTEN, TSHR, AKT1, GNAS, RET, TERT, and EIF1AX ranges between 100 bp-150 bp. The optimized set of PCR primer pairs useful in the methods of the present technology are disclosed in Tables 1 and 2. Further, as shown in FIG. 14, amplification of GC rich regions such as the TERT promoter also proved to be challenging. FIG. 14 shows that hot start DNA polymerases lacking 5'-3' exonuclease activity (e.g., ΔZ05-Gold polymerase or KAPA HiFi) were capable of consistently and successfully amplifying GC rich gene targets (e.g., the TERT promoter) unlike other DNA polymerases when tested under the same experimental conditions (0.6 ng/μL input DNA).

Example 2: Methods for Validating the Efficacy of the Thyroid Cancer Screening Assay of the Present Technology This Example demonstrates that the highly sensitive PCR-based NGS assay of the present technology is useful in methods for detecting mutations in the preselected set of thyroid cancer-related genes disclosed herein.

Methods. Total nucleic acids were harvested from FNA samples or FFPE samples using the Agencourt Formapure extraction kit. DNA quantification was performed using a Qubit DNA HS assay kit (Life Technologies, Carlsbad, Calif.). Samples with at least 1 ng of DNA were selected for NGS analysis. Samples having a DNA concentration >30 ng/μL were diluted down to 5-10 ng/μL with Low TE.

DNA Library.

A PCR amplicon library was generated from the extracted genomic DNA of each sample. Targeted regions within the 14 genes were amplified (using the primer pairs listed in Table 1) via PCR. Each reaction contained 2 μL of sample DNA (minimum DNA input requirement is 0.2 ng/μL); forward and reverse primers listed in Table 1 excluding the TERT promoter-specific primers (final concentrations of individual primer pairs are shown in FIG. 2A); 10 mM dNTPs; ΔZ05 Master Mix (Celera); and ΔZ05 Gold Polymerase (Celera). PCR amplification was carried out under the following conditions:

| Temperature | Time | #Cycles |
|---|---|---|
| 95° C. | 12 min | 1 |
| 95° C. | 15 sec | 30 |
| 62° C. | 4 min | |
| 62° C. | 7 min | 1 |
| 99° C. | 10 min | |
| 10° C. | | |

The GC-rich region of the TERT promoter was amplified using the following set up:

| Reagent | 1 Rxn (μL) |
| --- | --- |
| 2X PCR Master Mix with AZ05 Gold | 5 |
| TERT_02 TAG Fwd/Rev | 1 |
| (final concentration = 250 nM) | |
| Nuclease-free water | 2 |
| Sample | 2 |
| Total | 10 |

PCR amplification of the TERT promoter was carried out under the following conditions:

| Temperature | Time | #Cycles |
| --- | --- | --- |
| 95° C. | 10 min | 1 |
| 95° C. | 15 sec | 45 |
| 65° C. | 1 min | |
| 65° C. | 10 min | 1 |
| 4° C. | | |

RNA Library.

Extracted RNA (2-4 ng) was reverse transcribed into cDNA using the SuperScript III first-strand Synthesis Super-Mix kit (Life Technologies) under the following conditions:

| Temperature | Time |
| --- | --- |
| 25° C. | 10 min |
| 50° C. | 30 min |
| 85° C. | 5 min |
| 4° C. | Hold |

A PCR amplicon library was generated from the synthesized cDNA from each sample. Targeted regions within RET, PPARγ, NTRK1, NTRK3, BRAF, MET, LTK, THADA, FGFR2 and ALK were amplified using the primers listed in Table 2 via PCR. Each reaction contained 5 μL of sample cDNA; forward and reverse primers listed in Table 2 (final concentrations of individual primer pairs are shown in FIG. 2B); and 2× AmpliTaq Gold® 360 PCR master mix (Life Technologies). PCR amplification was carried out under the following conditions:

| Temperature | Time | #Cycles |
| --- | --- | --- |
| 95° C. | 10 min | 1 |
| 95° C. | 15 sec | 35 |
| 60° C. | 1 min | |
| 72° C. | 7 min | 1 |
| 4° C. | | |

The PCR amplicon DNA and RNA libraries underwent two rounds of purification using the Apollo Ampure 1.8× protocol (Agencourt). DNA quantification was performed using a Qubit DNA HS assay kit (Life Technologies, Carlsbad, Calif.). P5 and P7 adaptor sequences (along with index sequences) were incorporated on to the ends of the amplicons via a second PCR reaction (see FIG. 1) under the following conditions:

| Temperature | Time | #Cycles |
| --- | --- | --- |
| 98° C. | 2 min | 1 |
| 98° C. | 30 sec | 15 |
| 65° C. | 30 sec | |
| 72° C. | 1 min | |
| 72° C. | 4 min | 1 |
| 10° C. | | |

Amplicons of the second PCR reaction were purified using the Apollo Ampure 1.8× protocol (Agencourt). DNA was quantified using a Qubit DNA HS assay kit. Libraries were pooled by diluting multiple samples. Each library pool contained a positive control DNA sample, harboring multiple variants with known frequencies (Horizon Diagnostics, Waterbeach, Cambridge, UK). Each library pool was sequenced using the MiSeq platform (Illumina) according to the manufacturer's protocol. Specifically, the immobilized templates were clonally amplified to generate millions of molecular clusters each containing ~1,000 copies of the same template. The clustered templates were then sequenced using Illumina's sequencing-by-synthesis technology. A single NGS run may generate sequence data of up to 1.2 GB on a Micro Flow cell (2×150 cycles) or 4.5 GB on a Flow cell (2×150 cycles).

Data for the completed runs was made available in the IDBS web portal (sjcls0134.us.qdx.com:15100/portal/) for QC review. Each batch was reviewed for meeting minimum coverage depth (300), as well as the performance of the positive and negative QC samples.

Results. As shown in FIG. 3, all known mutations (including SNVs and INDELs) of the positive control DNA sample (Horizon mutation mix) were detected at approximately the expected frequency. Among the 14 clinical samples tested, 5 had known mutations (SJC-A05, A08, A09, D05, R-9955), all of which were detected by the thyroid cancer screening methods disclosed herein. Further, additional mutations were detected in 3 out of 5 mutation positive samples. For example, a known hotspot TERT promoter mutation (-146 C>T) along with a BRAF V600E mutation was detected in sample SJC-A08 (FIG. 3).

Moreover, mutations were also detected in 1 out of 8 clinical samples that were previously classified as mutation negative. For instance, KRAS G12V (2%), BRAF V600E (3%), and AKT1 E17K (3%) mutations were detected in R-10536, which tested negative for BRAF and RAS via BRAF ASO and RAS pyrosequencing. Reevaluation of the RAS pyrosequencing results revealed that a KRAS G12V mutation was indeed present in R-10536, whereas the V600E BRAF mutation remained undetectable when assayed via BRAF ASO.

Accordingly, these results demonstrate that the thyroid cancer screening assay of the present technology is useful in methods for detecting at least one mutation in the plurality of thyroid cancer-related genes disclosed herein in a subject at risk for or suspected of having thyroid cancer.

Example 3: Evaluation of Precision and Analytical Sensitivity of the Thyroid Cancer Screening Assay of the Present Technology Eight specimens with known variants (single nucleotide variant (SNV), insertions/deletions (INDEL), and gene fusions) were assayed three times within a single run, as well as four times between runs. In addition, both FFPE and FNA specimens were included in the precision studies (see table below).

| Sample ID | Specimen type | Known variant(s) |
|---|---|---|
| QC1 | Extracted DNA | AKT1 E17K, BRAF V600E, CTNNB1 S33Y; S45del KRAS G13D, NRAS Q61R PIK3CA E545K, H1047R |
| QC2 | FFPE | EML4-ALK |
| QC3 | FNA | Not Detected |
| QC4 | FNA | NRAS Q61R |
| QC5 | FNA | BRAF V600E |
| QC6 | FFPE | BRAF V600E, TERT-228 |
| QC7 | FFPE | Not Detected |
| QC8 | FNA | RET-PTC1 |

Intra-Assay Precision.

All known variants (SNVs, INDELs, gene fusion products) were detected in all three Intra-assay replicates. With respect to mutations, the SD of variant frequency in samples QC1 and QC4-6 ranged from 0.1-5.8% (FIG. 4). Fusion products were detected in samples QC2 (EML4-ALK) and QC8 (RET-PTC1) (FIG. 5).

Inter-Assay Precision.

All known variants (SNVs, INDELs, gene fusion products) were detected in all four Inter-assay replicates. With respect to mutations, the SD of variant frequency in samples QC1 and QC4-6 ranged from 0.4-5.4% (FIG. 6). Fusion products were detected in samples QC2 (EML4-ALK) and QC8 (RET-PTC1) (FIG. 7).

Analytical Sensitivity.

To determine the analytic sensitivity of the methods of the present technology, mixing studies were performed using 4 clinical samples (2 FFPE and 2 FNA samples; 2 of which are mutation positive and 2 translocation positive) serially mixed with either normal thyroid FFPE or mutation/translocation negative FNA samples. With respect to detecting mutations, the BRAF V600E and KRAS G12D SNVs and the TP53 12-nucleotide deletion were detectable when were present at frequencies as low as 1%. The TERT-228 SNV (-124 C>T) was detected when present at frequencies as low as 2% (FIG. 8). Accordingly, the methods disclosed herein are capable of detecting both SNVs and INDELs at frequencies as low as 2%.

With respect to detecting gene fusion products, the EML4-ALK translocation was detected in a 1:32 mixed FFPE sample (at 276 reads), while the RET-PTC1 translocation was detected in the 1:32 mixed FNA sample (at 64 reads, FIG. 9). Accordingly, the methods disclosed herein are capable of detecting gene fusion products consistently at ≥50 reads.

Detection Limit Studies.

To determine the minimal sample requirement of the disclosed methods, dilution series studies were performed using four clinical samples (2 FFPE and 2 FNA samples; 2 mutation positive and 2 translocation positive as shown in FIGS. 10 and 11) serially diluted with low TE. With respect to detecting mutations, the methods of the present technology were able to detect all three SNVs (NRAS Q61R, TERT-250 (-146 C>T), BRAF V600E) at the lowest DNA input tested (0.1 ng/μL, FIG. 10). However, the detected frequency for TERT-250 deviated from the expected frequency at levels below 0.3 ng/μL.

With respect to detecting translocations, the methods of the present technology were able to detect the PAX8-PPARG translocation at the lowest RNA input tested (0.1 ng/μL at 21322 reads, FIG. 11). In contrast, the RET-PTC1 translocation was detectable at 0.3 ng/μL or higher (at 2812 reads, FIG. 11).

Accuracy Studies.

The Horizon reference mixture (i.e., the QC1 sample) was tested in multiple setups to assess the recovery of known variants. The expected variant frequency, based on mixing calculations, and the observed variant frequency are shown in FIG. 12 (A). All known variants were detected by the methods of the present technology with variant frequency SD values ranging from 1.28-3.45%. See FIG. 12 (A). The acceptable frequency range (%) of known variants is provided in FIG. 12 (B). As shown in FIG. 12 (B), the low end of the acceptable frequency range for the AKT1 E17K variant is 2.5%. Thus, 1 out of 10 validation runs (Run ID: MS-1, FIG. 12 (A)) failed to detect the AKT1 E17K SNV in the QC1 sample, indicating a 98.75% (79/80) concordance recovery of known mutation variants.

Twenty-six synthetic double-stranded gBlock DNA fragments containing select RET, PPARγ, NTRK1, NTRK3, BRAF, MET, LTK, and ALK translocations were designed and assayed using the methods of the present technology to assess the recovery of these fusion variants. FIG. 15(A) demonstrates that all 26 of the synthetic fusion variants were detected by the methods of the present technology at assay input copies ranging from 100-2000. Seven synthetic double-stranded gBlock DNA fragments containing THADA and FGFR2 translocations (at 400 input copies) were designed and assayed using the methods of the present technology to assess the recovery of these fusion variants. FIG. 15(B) shows that all 7 of the synthetic fusion variants were detected by the methods of the present technology, when present at 400 copies.

Improved Diagnostic Performance.

A total of 34 FNA thyroid specimens and 14 FFPE specimens (6 thyroid, 8 others) that were previously tested by either the 7-gene thyroid panel (BRAF by allele-specific PCR, RAS by pyrosequencing, PAX8-PPARG and RET-PTC1/3 by RT-PCR) or other alternative methods were assayed using the NGS-based thyroid cancer screening methods of the present technology.

Among the 40 assayed thyroid specimens that generated a valid NGS result, 15 variants (10 SNVs, 5 fusion products) were detected in 15 samples via the 7-gene assay. In contrast, 24 variants (18 SNVs, 6 fusions) were detected in 20 samples using the methods of the present technology (see FIG. 13 (A), summarized in FIG. 13 (B)). Further, 12.5% (5 out of 40) of the thyroid specimens had actionable variants that were detected using the NGS-based thyroid cancer screening methods of the present technology, but not the conventional 7-gene thyroid panel. Identification of these actionable variants may be useful in informing disease management decisions in thyroid cancer subjects (e.g., selecting a subject for diagnostic surgery, e.g., a lobectomy).

Table 4 demonstrates that the methods of the present technology show enhanced sensitivity in detecting mutations in samples with inconclusive FNA cytology compared to the traditional 7-gene thyroid panel.

TABLE 4

Detection of Mutations in Samples with Inconclusive FNA Cytology

| Specimen | # tested | # Positive by 7-gene panel | # Positive by 2-step PCR method of the present technology* | Mutation | Translocation |
|---|---|---|---|---|---|
| Normal | 13 | 0 | 0 | | |
| Benign | 11 | 0 | 2 | TSHR (n = 2), M453T at 11%; F631L at 10% | |
| AUS/FLUS | 18 | 2 | 4 | KRAS (n = 2), G12V at 7%; G13D at 14% TSHR (n = 2), F631L at 5%; T632I at 23% | |
| FN/SFN | 5 | 1 | 3 | GNAS (n = 1), R201H at 24% RET (n = 1), H745R at 15% | PAX8-PPARG (n = 1) |
| SUSP | 4 | 2 | 3 | BRAF (n = 2), V600E at 24%; V600E at 2% | NTRK3 (n = 1) |
| Malignant | 8 | 6 | 8 | BRAF (n = 3), V600E at 33%; V600E at 15%; V600E at 41% BRAF + TERT (n = 1), V600E at 25%; TERT-228 at 14%) RET (n = 1), M918T at 33% | RET-PTC (n = 1), ALK (n = 1), RET-PTC + TERT (n = 1), TERT-228 at 21% |
| Total | 59 | 11 | 20 | | |

*The 2-step PCR method screens for mutations in BRAF, NRAS, HRAS, KRAS, PIK3CA, TP53, CTNNB1, PTEN, TSHR, AKT1, GNAS, RET, TERT, and EIF1AX, and translocations in RET, PPARγ, NTRK1, NTRK3, BRAF, MET, LTK, and ALK.

According to Table 4, the NGS PCR-based thyroid cancer screening methods of the present technology detected actionable variants in 15% more samples with abnormal FNA cytology results compared to the 7-gene thyroid panel. As shown in Table 4, the NGS-based methods of the present technology detected actionable variants in twice as many samples having inconclusive FNA cytology (AUS/FLUS, FN/SFN, SUSP) compared to the 7-gene thyroid panel (i.e., 10 samples vs. 5 samples). Moreover, unlike the 7-gene thyroid panel, the methods of the present technology detected TSHR activating mutations in 2 samples having 'benign' FNA cytology. These diagnostic results are significant because the M453T and F631L mutations of TSHR have been previously implicated in thyroid carcinoma and hyperfunctioning thyroid adenoma/toxic multinodular goiter respectively (Iosco & Rhoden, *Atlas of Genetics and Cytogenetics in Oncology and Haematology* (2009), atlasgeneticsoncology.org/Genes/TSHRID290ch14q31.html). Further, the NGS-based methods of the present technology detected actionable variants in 100% of the samples that exhibited malignant FNA cytology. In contrast, the 7-gene thyroid panel detected actionable variants in only 75% of the samples with malignant FNA cytology. Thus, the methods disclosed herein are useful in predicting the risk of malignancy in a subject with inconclusive thyroid FNA cytology results, and guiding treatment decisions (e.g., diagnostic surgery) in such subjects.

These results demonstrate that the NGS-based thyroid cancer screening methods of the present technology have improved breadth of coverage and sensitivity over the conventional 7-gene thyroid panel. Accordingly, the methods of the present technology are useful for predicting the risk of malignancy in a subject with inconclusive thyroid FNA cytology results. The methods disclosed herein are also useful for selecting a subject having thyroid nodules with indeterminate cytology for diagnostic surgery.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. A method for detecting at least one mutation in a plurality of thyroid cancer-related genes in a subject comprising
   (a) extracting DNA from a FFPE thyroid sample or a FNA thyroid sample obtained from the subject;
   (b) generating a DNA library of a first plurality of amplicons using a hot start DNA polymerase that substantially lacks 5'-3' exonuclease activity, wherein at least one amplicon corresponds to each of the plurality of thyroid cancer-related genes, said plurality of thyroid cancer-related genes comprising BRAF, NRAS, HRAS, KRAS, PIK3CA, TP53, CTNNB1, PTEN, TSHR, AKT1, GNAS, RET, EIF1AX, and TERT promoter;
   (c) incorporating an adapter sequence on to the ends of the first plurality of amplicons via polymerase chain reaction; and
   (d) detecting at least one mutation in at least one of the first plurality of amplicons using high throughput massive parallel sequencing.

2. The method of claim 1, wherein the first plurality of amplicons is generated using at least two primer pairs selected from the group consisting of SEQ ID NOs: 1-118.

3. The method of claim 1, wherein the first plurality of amplicons is generated using no more than 1 ng of extracted DNA from the FFPE thyroid sample or the FNA thyroid sample.

4. The method of claim 1, wherein the first plurality of amplicons is generated using 1-25 ng of extracted DNA from the FFPE thyroid sample or the FNA thyroid sample.

5. The method of claim 1, wherein the first plurality of amplicons further comprises a unique index sequence.

6. The method of claim 1, wherein the hot start DNA polymerase that substantially lacks 5'-3' exonuclease activity is ΔZ05-Gold polymerase.

7. The method of claim 1, further comprising detecting a gene fusion product in one or more of RET, PPARγ, NTRK1, NTRK3, BRAF, MET, LTK, THADA, FGFR2 and ALK in the subject comprising
   (a) extracting RNA from the FFPE thyroid sample or the FNA thyroid sample obtained from the subject;
   (b) reverse-transcribing the extracted RNA into cDNA;
   (c) generating a cDNA library of a second plurality of amplicons using a hot start DNA polymerase with 5'-3' exonuclease activity, wherein at least one amplicon corresponds to each of RET, PPARγ, NTRK1, NTRK3, BRAF, MET, LTK, THADA, FGFR2 and ALK;
   (d) incorporating an adapter sequence on to the ends of the second plurality of amplicons via polymerase chain reaction; and
   (e) detecting at least one gene fusion product in at least one of the second plurality of amplicons using high throughput massive parallel sequencing.

8. The method of claim 7, wherein the second plurality of amplicons is generated using at least two or more primers selected from the group consisting of SEQ ID NOs: 119-193.

9. The method of claim 7, wherein the second plurality of amplicons further comprises a unique index sequence.

10. The method of claim 7, wherein the hot start DNA polymerase with 5'-3' exonuclease activity is AmpliTaq Gold polymerase.

11. The method of claim 7, wherein the at least one gene fusion product detected is selected from the group consisting of CCDC6 (PTC1) Exon 1/RET Exon 12, PRKAR1A Exon 8/RET Exon 12, NCOA4 Exon 10/RET Exon 12, NCOA4 Exon 9/RET Exon 12, GOLGA5 Exon 7/RET Exon 12, TRIM24 Exon 9/RET Exon 12, TRIM33 (PTC1) Exon 16/RET Exon 12, ERC1 (ELKS) Exon 11/RET Exon 12, KTN1 Exon 30/RET Exon 12, PCM1 Exon 29/RET Exon 12, TRIM27 Exon 3/RET Exon 12, HOOK3 Exon 11/RET Exon 12, CREB3L2 Exon 2/PPARγ Exon 5, PAX8 Exon 7/PPARγ Exon 5, PAX8 Exon 8/PPARγ Exon 5, PAX8 Exon 9/PPARγ Exon 5, PAX8 Exon 10/PPARγ Exon 5, ETV6 Exon 4/NTRK3 Exon 14, BRAF Exon 8/MACF1 Exon 15, AKAP9 Exon 8/BRAF Exon 9, AGK Exon 2/BRAF Exon 8, TFG Exon 5/NTRK1 Exon 12, TPM3 Exon 10/NTRK1 Exon 12, TPR Exon 21/NTRK1 Exon 12, ETV6 Exon 5/NTRK3 Exon 14, STRN Exon 3/ALK Exon 20, EML4 Exon 13/ALK Exon 20, EML4 Exon 20/ALK Exon 20, EML4 Exon 6/ALK Exon 20, TFG Exon 5/MET Exon 15, UACA Exon 17/LTK Exon 10, AGGF1 Exon 5/RAF1 Exon 8, MACF1 Exon 60/BRAF Exon 9, THADA Exon 27/PPARG Intron 2a, THADA Exon 27/PPARG Intron 2b, THADA Exon 27/Chr 7p non-coding (FUS7p), THADA Exon 28/IGF2BP3 Exon 4, TRA2A Exon 7/THADA Exon 37, FGFR2 Exon 16-OFD1 Exon 3, VCL Exon 1/FGFR2 Exon 18, and SND1 Exon 10/BRAF Exon 9.

12. The method of claim 1, wherein the FNA thyroid sample has been diagnosed as AUS/FLUS, FN/SFN or SUSP.

13. A method for selecting a subject having thyroid nodules with indeterminate cytology for diagnostic surgery comprising:
   (a) extracting DNA from a FNA thyroid sample obtained from the subject;

(b) generating a DNA library of a first plurality of amplicons using a hot start DNA polymerase that substantially lacks 5'-3' exonuclease activity, wherein at least one amplicon corresponds to each of a plurality of thyroid cancer-related genes, said plurality of thyroid cancer-related genes comprising BRAF, NRAS, HRAS, KRAS, PIK3CA, TP53, CTNNB1, PTEN, TSHR, AKT1, GNAS, RET, EIF1AX, and TERT promoter;

(c) incorporating an adapter sequence on to the ends of the first plurality of amplicons via polymerase chain reaction; and (d) selecting the subject for diagnostic surgery, if a mutation in at least one of the first plurality of amplicons corresponding to BRAF, NRAS, HRAS, KRAS, PIK3CA, TP53, CTNNB1, PTEN, TSHR, AKT1, RET, EIF1AX, and TERT promoter is detected.

14. The method of claim 13, wherein the first plurality of amplicons is generated using at least two primer pairs selected from the group consisting of SEQ ID NOs: 1-118 disclosed in Table 1.

15. The method of claim 13, wherein the at least one mutation detected is selected from the group consisting of AKT1 E17K, BRAF V600E, BRAF K601E, KRAS G13D, KRAS G12V, KRAS Q61R, KRAS G12D, NRAS Q61R, NRAS Q61K, PIK3CA E545K, PIK3CA H1047R, PIK3CA G914R, HRAS Q61R, RET M918T, TSHR R274W, TSHR A581S, TERT-124 C>T and TERT-146 C>T.

16. The method of claim 13, wherein the first plurality of amplicons is generated using no more than 1 ng of extracted DNA from the FNA thyroid sample.

17. The method of claim 13, wherein the first plurality of amplicons is generated using 1-25 ng of extracted DNA from the FNA thyroid sample.

18. The method of claim 13, wherein the first plurality of amplicons further comprises a unique index sequence.

19. The method of claim 13, wherein the hot start DNA polymerase that substantially lacks 5'-3' exonuclease activity is ΔZ05-Gold polymerase.

20. The method of claim 13, further comprising detecting a gene fusion product in one or more of RET, PPARγ, NTRK1, NTRK3, BRAF, MET, LTK, THADA, FGFR2 and ALK in the subject comprising (a) extracting RNA from the FNA thyroid sample obtained from the subject;

(b) reverse-transcribing the extracted RNA into cDNA;

(c) generating a cDNA library of a second plurality of amplicons using a hot start DNA polymerase with 5'-3' exonuclease activity, wherein at least one amplicon corresponds to each of RET, PPARγ, NTRK1, NTRK3, BRAF, MET, LTK, THADA, FGFR2 and ALK;

(d) incorporating an adapter sequence on to the ends of the second plurality of amplicons via polymerase chain reaction; and (e) selecting the subject for diagnostic surgery, if a gene fusion product in at least one of the second plurality of amplicons corresponding to RET, PPARγ, NTRK1, NTRK3, BRAF, MET, LTK, THADA, FGFR2 and ALK is detected.

21. The method of claim 20, wherein the second plurality of amplicons is generated using at least two primers selected from the group consisting of SEQ ID NOs: 119-193.

22. The method of claim 20, wherein the gene fusion product detected is selected from the group consisting of CCDC6 (PTC1) Exon 1/RET Exon 12, PRKAR1A Exon 8/RET Exon 12, NCOA4 Exon 10/RET Exon 12, NCOA4 Exon 9/RET Exon 12, GOLGA5 Exon 7/RET Exon 12, TRIM24 Exon 9/RET Exon 12, TRIM33 (PTC1) Exon 16/RET Exon 12, ERC1 (ELKS) Exon 11/RET Exon 12, KTN1 Exon 30/RET Exon 12, PCM1 Exon 29/RET Exon 12, TRIM27 Exon 3/RET Exon 12, HOOK3 Exon 11/RET Exon 12, CREB3L2 Exon 2/PPARγ Exon 5, PAX8 Exon 7/PPARγ Exon 5, PAX8 Exon 8/PPARγ Exon 5, PAX8 Exon 9/PPARγ Exon 5, PAX8 Exon 10/PPARγ Exon 5, ETV6 Exon 4/NTRK3 Exon 14, BRAF Exon 8/MACF1 Exon 15, AKAP9 Exon 8/BRAF Exon 9, AGK Exon 2/BRAF Exon 8, TFG Exon 5/NTRK1 Exon 12, TPM3 Exon 10/NTRK1 Exon 12, TPR Exon 21/NTRK1 Exon 12, ETV6 Exon 5/NTRK3 Exon 14, STRN Exon 3/ALK Exon 20, EML4 Exon 13/ALK Exon 20, EML4 Exon 20/ALK Exon 20, EML4 Exon 6/ALK Exon 20, TFG Exon 5/MET Exon 15, UACA Exon 17/LTK Exon 10, AGGF1 Exon 5/RAF1 Exon 8, MACF1 Exon 60/BRAF Exon 9, THADA Exon 27/PPARG Intron 2a, THADA Exon 27/PPARG Intron 2b, THADA Exon 27/Chr 7p non-coding (FUS7p), THADA Exon 28/IGF2BP3 Exon 4, TRA2A Exon 7/THADA Exon 37, FGFR2 Exon 16/OFD1 Exon 3, VCL Exon 1/FGFR2 Exon 18, and SND1 Exon 10/BRAF Exon 9.

23. The method of claim 20, wherein the second plurality of amplicons further comprises a unique index sequence.

24. The method of claim 20, wherein the hot start DNA polymerase with 5'-3' exonuclease activity is AmpliTaq Gold polymerase.

25. The method of claim 13, wherein the FNA thyroid sample has been diagnosed as AUS/FLUS, FN/SFN or SUSP.

26. The method of claim 13, wherein the diagnostic surgery is lobectomy.

27. A method for predicting the risk of malignancy in a subject with inconclusive thyroid FNA cytology results comprising:

(a) extracting DNA from a FNA thyroid sample obtained from the subject;

(b) generating a DNA library of a first plurality of amplicons using a hot start DNA polymerase that substantially lacks 5'-3' exonuclease activity, wherein at least one amplicon corresponds to each of a plurality of thyroid cancer-related genes, said plurality of thyroid cancer-related genes comprising BRAF, NRAS, HRAS, KRAS, PIK3CA, TP53, CTNNB1, PTEN, TSHR, AKT1, GNAS, RET, EIF1AX, and TERT promoter;

(c) incorporating an adapter sequence on to the ends of the first plurality of amplicons via polymerase chain reaction; and (d) identifying the subject as having a high risk of malignancy when a mutation in at least one of the first plurality of amplicons corresponding to BRAF, NRAS, HRAS, KRAS, PIK3CA, TP53, CTNNB1, PTEN, TSHR, AKT1, RET, EIF1AX, and TERT promoter is detected.

28. The method of claim 27, wherein the first plurality of amplicons is generated using at least two primer pairs selected from the group consisting of SEQ ID NOs: 1-118.

29. The method of claim 27, further comprising detecting a gene fusion product in one or more of RET, PPARγ, NTRK1, NTRK3, BRAF, MET, LTK, THADA, FGFR2 and ALK in the subject comprising (a) extracting RNA from a FNA thyroid sample obtained from the subject;

(b) reverse-transcribing the extracted RNA into cDNA;

(c) generating a cDNA library of a second plurality of amplicons using a hot start DNA polymerase with 5'-3' exonuclease activity, wherein at least one amplicon corresponds to each of RET, PPARγ, NTRK1, NTRK3, BRAF, MET, LTK, THADA, FGFR2 and ALK;

(d) incorporating an adapter sequence on to the ends of the second plurality of amplicons via polymerase chain reaction; and (e) identifying the subject as having a high risk of malignancy when a gene fusion product in at least one of the second plurality of amplicons corresponding to RET, PPARγ, NTRK1, NTRK3, BRAF, MET, LTK, THADA, FGFR2 and ALK is detected.

30. The method of claim 29, wherein the second plurality of amplicons is generated using at least two primers selected from the group consisting of SEQ ID NOs: 119-193.

* * * * *

UNITED STATES PATENT AND TRADEMARK OFFICE
CERTIFICATE OF CORRECTION

| | |
|---|---|
| PATENT NO. | : 11,053,542 B2 |
| APPLICATION NO. | : 16/067189 |
| DATED | : July 6, 2021 |
| INVENTOR(S) | : Cheng et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 281 days.

Signed and Sealed this
Thirty-first Day of January, 2023

Katherine Kelly Vidal
*Director of the United States Patent and Trademark Office*